United States Patent
Cha et al.

(10) Patent No.: US 10,822,330 B2
(45) Date of Patent: Nov. 3, 2020

(54) HETEROCYCLIC COMPOUND AND ORGANIC LIGHT EMITTING DIODE CONTAINING SAME

(71) Applicant: LG Chem, Ltd., Seoul (KR)

(72) Inventors: Yongbum Cha, Daejeon (KR); Seongmi Cho, Daejeon (KR); Jungbum Kim, Daejeon (KR); Sung Kil Hong, Daejeon (KR); Jiwon Kwak, Daejeon (KR)

(73) Assignee: LG Chem, Ltd. (KR)

( * ) Notice: Subject to any disclaimer, the term of this patent is extended or adjusted under 35 U.S.C. 154(b) by 311 days.

(21) Appl. No.: 15/757,809

(22) PCT Filed: Feb. 24, 2017

(86) PCT No.: PCT/KR2017/002062
§ 371 (c)(1),
(2) Date: Mar. 6, 2018

(87) PCT Pub. No.: WO2017/146522
PCT Pub. Date: Aug. 31, 2017

(65) Prior Publication Data
US 2020/0123138 A1    Apr. 23, 2020

(30) Foreign Application Priority Data
Feb. 25, 2016    (KR) .................. 10-2016-0022653

(51) Int. Cl.
| | | |
|---|---|---|
| C07D 409/14 | (2006.01) | |
| H01L 51/42 | (2006.01) | |
| H01L 51/50 | (2006.01) | |
| C07D 407/04 | (2006.01) | |
| C07D 407/14 | (2006.01) | |

(Continued)

(52) U.S. Cl.
CPC ........ *C07D 409/14* (2013.01); *C07D 407/04* (2013.01); *C07D 407/14* (2013.01); *C07D 409/04* (2013.01); *H01L 51/0052* (2013.01); *H01L 51/0072* (2013.01); *H01L 51/0073* (2013.01); *H01L 51/0074* (2013.01);
(Continued)

(58) Field of Classification Search
CPC .................................................. C07D 409/14
See application file for complete search history.

(56) References Cited

U.S. PATENT DOCUMENTS

| | | |
|---|---|---|
| 7,087,798 B2 | 8/2006 | Shiigi et al. |
| 2004/0251816 A1 | 12/2004 | Leo et al. |

(Continued)

FOREIGN PATENT DOCUMENTS

| | | | |
|---|---|---|---|
| JP | 2009283786 A | * | 12/2009 |
| KR | 20110002156 A | | 1/2011 |

(Continued)

OTHER PUBLICATIONS

Search report from International Application No. PCT/KR2017/002062, dated May 31, 2017.

(Continued)

*Primary Examiner* — Moazzam Hossain
(74) *Attorney, Agent, or Firm* — Lerner, David, Littenberg, Krumholz & Mentlik, LLP

(57) ABSTRACT

The present specification relates to a hetero-cyclic compound and an organic light emitting device including the same.

11 Claims, 1 Drawing Sheet

(51) Int. Cl.
*C07D 409/04* (2006.01)
*H01L 51/00* (2006.01)

(52) U.S. Cl.
CPC ...... *H01L 51/4273* (2013.01); *H01L 51/5056* (2013.01); *H01L 51/5072* (2013.01)

(56) References Cited

U.S. PATENT DOCUMENTS

| | | | |
|---|---|---|---|
| 2010/0227956 A1* | 9/2010 | Brown | H01L 51/0074 |
| | | | 524/84 |
| 2010/0244000 A1* | 9/2010 | Tanaka | H01L 51/0562 |
| | | | 257/40 |
| 2013/0327995 A1* | 12/2013 | Maunoury | C07C 13/72 |
| | | | 252/519.21 |
| 2016/0190466 A1 | 6/2016 | Pfister et al. | |
| 2016/0233430 A1 | 8/2016 | Heo et al. | |
| 2016/0308147 A1* | 10/2016 | Parham | C07D 405/04 |
| 2017/0012219 A1 | 1/2017 | Parham et al. | |
| 2017/0207396 A1 | 7/2017 | Park et al. | |

FOREIGN PATENT DOCUMENTS

| | | |
|---|---|---|
| KR | 20160011582 A | 2/2016 |
| TW | 201527292 A | 7/2015 |
| TW | 201527296 A | 7/2015 |
| WO | 2015022051 A1 | 2/2015 |
| WO | 2015090504 A2 | 6/2015 |
| WO | 2015128052 A1 | 9/2015 |

OTHER PUBLICATIONS

Taiwanese Search Report for TW Application No. 106106296, dated Mar. 12, 2018.

* cited by examiner

[Figure 1]
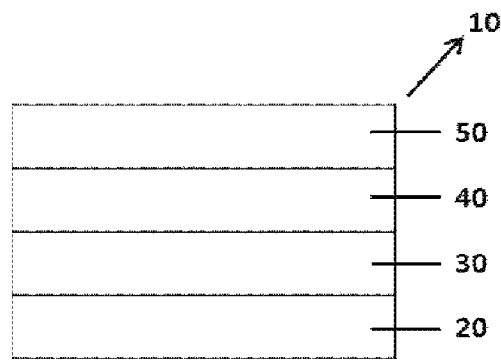
[Figure 2]
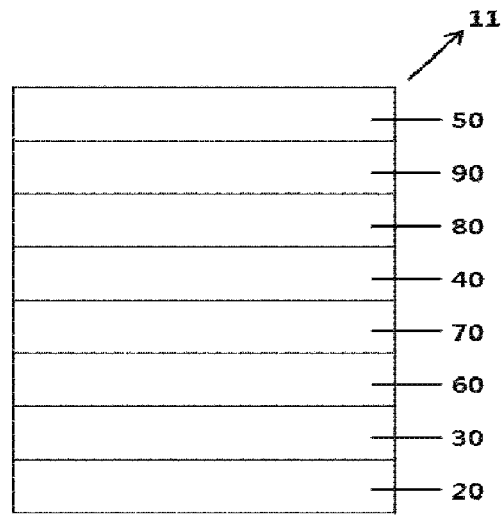

HETEROCYCLIC COMPOUND AND ORGANIC LIGHT EMITTING DIODE CONTAINING SAME

CROSS-REFERENCE TO RELATED APPLICATIONS

The present invention is a national phase entry under 35 U.S.C. § 371 of International Application No. PCT/KR2017/002062, filed Feb. 24, 2017, which claims priority from Korean Patent Application No. 10-2016-0022653 filed in the Korean Intellectual Property Office on Feb. 25, 2016, the entire contents of which are incorporated herein by reference.

TECHNICAL FIELD

The present specification relates to a hetero-cyclic compound and an organic light emitting device including the same.

BACKGROUND ART

In general, an organic light emitting phenomenon refers to a phenomenon in which electric energy is converted into light energy by using an organic material. An organic light emitting device using the organic light emitting phenomenon usually has a structure including a positive electrode, a negative electrode, and an organic material layer interposed therebetween. Here, the organic material layer may have in many cases a multi-layered structure composed of different materials in order to improve the efficiency and stability of an organic light emitting device, and for example, may be composed of a hole injection layer, a hole transporting layer, a light emitting layer, an electron transporting layer, an electron injection layer, and the like. In the structure of the organic light emitting device, if a voltage is applied between two electrodes, holes are injected from a positive electrode into the organic material layer and electrons are injected from a negative electrode into the organic material layer, and when the injected holes and electrons meet each other, an exciton is formed, and light is emitted when the exciton falls down again to a ground state.

There is a continuous need for developing a new material for the aforementioned organic light emitting device.

CITATION LIST

Patent Document

US Patent Publication No. 2004-0251816

DETAILED DESCRIPTION OF THE INVENTION

Technical Problem

The present specification provides a hetero-cyclic compound and an organic light emitting device including the same.

Technical Solution

An exemplary embodiment of the present specification provides a hetero-cyclic compound represented by the following Chemical Formula 1.

[Chemical Formula 1]

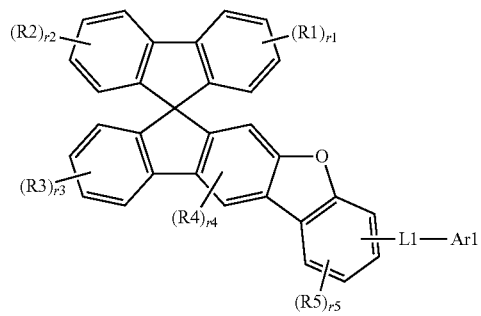

In Chemical Formula 1,

R1 to R5 are the same as or different from each other, and are each independently hydrogen; deuterium; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group, L1 is a direct bond; a substituted or unsubstituted arylene group; or a substituted or unsubstituted heteroarylene group, Ar1 is a substituted or unsubstituted phosphine oxide group; a substituted or unsubstituted aryl group; a substituted or unsubstituted quinolinyl group; a substituted or unsubstituted quinazolinyl group; or a substituted or unsubstituted tricyclic or more heteroaryl group, r1 and r2 are each an integer from 1 to 4, r3 is an integer from 1 to 4, r4 is 1 or 2, r5 is an integer from 1 to 3, and when r1 to r5 are each present in a plural number, a plurality of structures in the parenthesis is the same as or different from each other.

Further, an exemplary embodiment of the present specification provides an organic light emitting device including: a first electrode; a second electrode disposed to face the first electrode; and an organic material layer having one or more layers disposed between the first electrode and the second electrode, in which one or more layers of the organic material layer include the hetero-cyclic compound represented by Chemical Formula 1.

Advantageous Effects

The hetero-cyclic compound according to an exemplary embodiment of the present specification may be used as a material for an organic material layer of an organic light emitting device, and it is possible to improve efficiency, achieve low driving voltage, and/or improve service life characteristics in the organic light emitting device by using the same.

BRIEF DESCRIPTION OF DRAWINGS

FIG. 1 illustrates an organic light emitting device 10 according to an exemplary embodiment of the present specification.

FIG. 2 illustrates an organic light emitting device 11 according to another exemplary embodiment of the present specification.

EXPLANATION OF REFERENCE NUMERALS AND SYMBOLS 10, 11: Organic light emitting device
20: Substrate
30: First electrode
40: Light emitting layer
50: Second electrode
60: Hole injection layer
70: Hole transporting layer
80: Electron transporting layer
90: Electron injection layer

BEST MODE

Hereinafter, the present specification will be described in more detail.

The present specification provides the hetero-cyclic compound represented by Chemical Formula 1.

When one part "includes" one constituent element in the present specification, unless otherwise specifically described, this does not mean that another constituent element is excluded, but means that another constituent element may be further included.

When one member is disposed "on" another member in the present specification, this includes not only a case where the one member is brought into contact with another member, but also a case where still another member is present between the two members.

Examples of the substituents in the present specification will be described below, but are not limited thereto.

The term "substitution" means that a hydrogen atom bonded to a carbon atom of a compound is changed into another substituent, and a position to be substituted is not limited as long as the position is a position at which the hydrogen atom is substituted, that is, a position at which the substituent may be substituted, and when two or more are substituted, the two or more substituents may be the same as or different from each other.

In the present specification, the term "substituted or unsubstituted" means being substituted with one or two or more substituents selected from the group consisting of deuterium; a halogen group; a nitrile group; a nitro group; an imide group; an amide group; a carbonyl group; an ester group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; and a substituted or unsubstituted hetero-cyclic group or being substituted with a substituent to which two or more substituents are linked among the substituents exemplified above, or having no substituent. For example, "the substituent to which two or more substituents are linked" may be a biphenyl group. That is, the biphenyl group may also be an aryl group, and may be interpreted as a substituent to which two phenyl groups are linked.

In the present specification,

means a moiety bonded to another substituent or a bonding portion.

In the present specification, a halogen group may be fluorine, chlorine, bromine, or iodine.

In the present specification, the number of carbon atoms of an imide group is not particularly limited, but is preferably 1 to 30. Specifically, the imide group may be a compound having the following structures, but is not limited thereto.

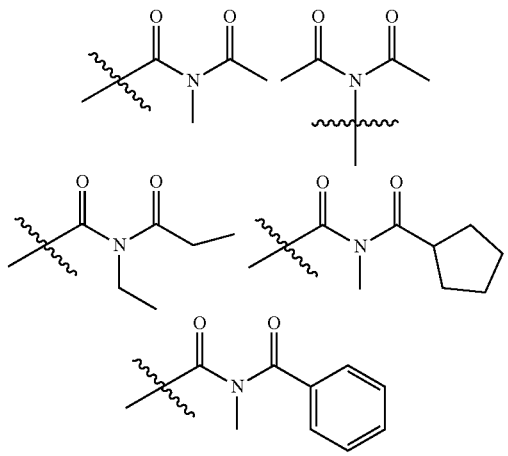

In the present specification, for an amide group, the nitrogen of the amide group may be substituted with hydrogen, a straight, branched, or cyclic alkyl group having 1 to 30 carbon atoms, or an aryl group having 6 to 30 carbon atoms. Specifically, the amide group may be a compound having the following structural formulae, but is not limited thereto.

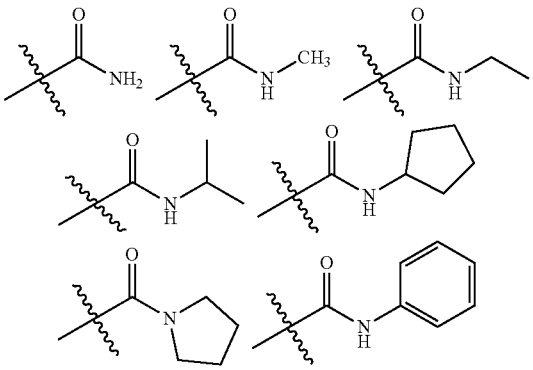

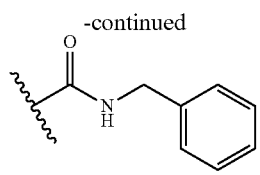

In the present specification, the number of carbon atoms of a carbonyl group is not particularly limited, but is preferably 1 to 30. Specifically, the carbonyl group may be a compound having the following structures, but is not limited thereto.

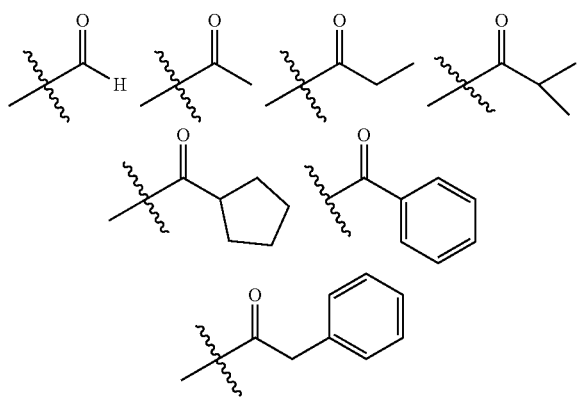

In the present specification, for an ester group, the oxygen of the ester group may be substituted with a straight, branched, or cyclic alkyl group having 1 to 25 carbon atoms, or an aryl group having 6 to 30 carbon atoms. Specifically, the ester group may be a compound having the following structural formulae, but is not limited thereto.

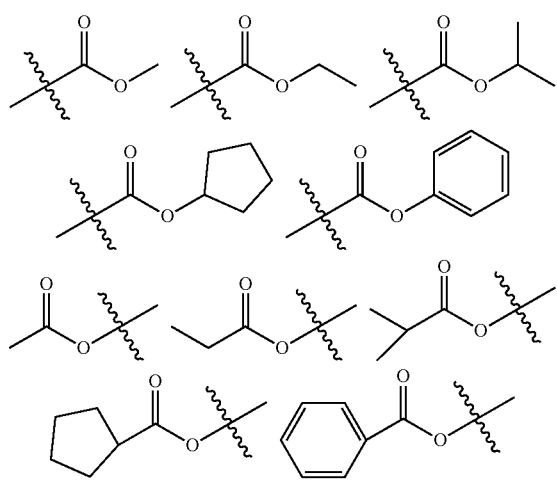

In the present specification, the alkyl group may be straight or branched, and the number of carbon atoms thereof is not particularly limited, but is preferably 1 to 30. Specific examples thereof include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present specification, a cycloalkyl group is not particularly limited, but has preferably 3 to 30 carbon atoms, and specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, the alkoxy group may be straight, branched, or cyclic. The number of carbon atoms of the alkoxy group is not particularly limited, but is preferably 1 to 30. Specific examples thereof include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy, and the like, but are not limited thereto.

In the present specification, an amine group may be selected from the group consisting of $—NH_2$; an alkylamine group; an N-alkylarylamine group; an arylamine group; an N-arylheteroarylamine group; an N-alkylheteroarylamine group; and a heteroarylamine group, and the number of carbon atoms thereof is not particularly limited, but is preferably 1 to 30. Specific examples of the amine group include a methylamine group; a dimethylamine group; an ethylamine group; a diethylamine group; a phenylamine group; a naphthylamine group; a biphenylamine group; an anthracenylamine group; a 9-methyl-anthracenylamine group; a diphenylamine group; an N-phenylnaphthylamine group; a ditolylamine group; an N-phenyltolylamine group; a triphenylamine group; an N-phenylbiphenylamine group; an N-phenylnaphthylamine group; an N-biphenylnaphthylamine group; an N-naphthylfluorenylamine group; an N-phenylphenanthrenylamine group; an N-biphenylphenanthrenylamine group; an N-phenylfluorenylamine group; an N-phenyl terphenylamine group; an N-phenanthrenylfluorenylamine group; an N-biphenylfluorenylamine group, and the like, but are not limited thereto.

In the present specification, an N-alkylarylamine group means an amine group in which an alkyl group and an aryl group are substituted with N of the amine group. In the present specification, an N-arylheteroarylamine group means an amine group in which an aryl group and a heteroaryl group are substituted with N of the amine group.

In the present specification, an N-alkylheteroarylamine group means an amine group in which an alkyl group and a heteroaryl group are substituted with N of the amine group.

In the present specification, the alkyl group in the alkylamine group, the N-arylalkylamine group, the alkylthioxy group, the alkylsulfoxy group, and the N-alkylheteroarylamine group is the same as the above-described examples of the alkyl group. Specifically, examples of the alkylthioxy group include a methylthioxy group, an ethylthioxy group, a tert-butylthioxy group, a hexylthioxy group, an octylthioxy group, and the like, and examples of the alkylsulfoxy group include mesyl, an ethylsulfoxy group, a propylsulfoxy group, a butylsulfoxy group, and the like, but the examples are not limited thereto.

In the present specification, the alkenyl group may be straight or branched, and the number of carbon atoms thereof is not particularly limited, but is preferably 2 to 30.

Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, specific examples of a silyl group include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but are not limited thereto.

In the present specification, a boron group may be $-BR_{100}R_{101}$, and $R_{100}$ and $R_{101}$ are the same as or different from each other, and may be each independently selected from the group consisting of hydrogen; deuterium; halogen; a nitrile group; a substituted or unsubstituted monocyclic or polycyclic cycloalkyl group having 3 to 30 carbon atoms; a substituted or unsubstituted straight or branched alkyl group having 1 to 30 carbon atoms; a substituted or unsubstituted monocyclic or polycyclic aryl group having 6 to 30 carbon atoms; and a substituted or unsubstituted monocyclic or polycyclic heteroaryl group having 2 to 30 carbon atoms.

In the present specification, specific examples of a phosphine oxide group include a diphenylphosphine oxide group, dinaphthylphosphine oxide group, and the like, but are not limited thereto.

In the present specification, an aryl group is not particularly limited, but has preferably 6 to 30 carbon atoms, and the aryl group may be monocyclic or polycyclic.

When the aryl group is a monocyclic aryl group, the number of carbon atoms thereof is not particularly limited, but is preferably 6 to 30. Specific examples of the monocyclic aryl group include a phenyl group, a biphenyl group, a terphenyl group, and the like, but are not limited thereto.

When the aryl group is a polycyclic aryl group, the number of carbon atoms thereof is not particularly limited, but is preferably 10 to 30. Specific examples of the polycyclic aryl group include a naphthyl group, an anthracenyl group, a phenanthryl group, a triphenyl group, a pyrenyl group, a phenalenyl group, a perylenyl group, a chrysenyl group, a fluorenyl group, and the like, but are not limited thereto.

In the present specification, the fluorenyl group may be substituted, and adjacent substituents may be bonded to each other to form a ring.

When the fluorenyl group is substituted, the fluorenyl group may be

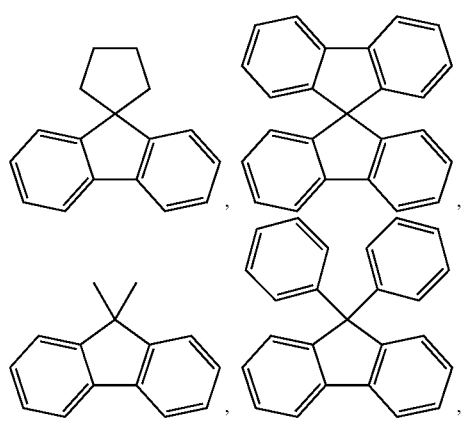

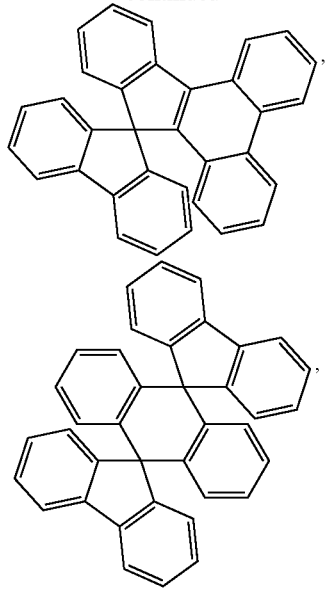

and the like. However, the fluorenyl group is not limited thereto.

In the present specification, the "adjacent" group may mean a substituent substituted with an atom directly linked to an atom in which the corresponding substituent is substituted, a substituent disposed sterically closest to the corresponding substituent, or another substituent substituted with an atom in which the corresponding substituent is substituted. For example, two substituents substituted at the ortho position in a benzene ring and two substituents substituted with the same carbon in an aliphatic ring may be interpreted as groups which are "adjacent" to each other.

In the present specification, the aryl group in the aryloxy group, the arylthioxy group, the arylsulfoxy group, the N-arylalkylamine group, the N-arylheteroarylamine group, and the arylphosphine group is the same as the above-described examples of the aryl group. Specifically, examples of the aryloxy group include a phenoxy group, a p-tolyloxy group, an m-tolyloxy group, a 3,5-dimethyl-phenoxy group, a 2,4,6-trimethylphenoxy group, a p-tert-butylphenoxy group, a 3-biphenyloxy group, a 4-biphenyloxy group, a 1-naphthyloxy group, a 2-naphthyloxy group, a 4-methyl-1-naphthyloxy group, a 5-methyl-2-naphthyloxy group, a 1-anthryloxy group, a 2-anthryloxy group, a 9-anthryloxy group, a 1-phenanthryloxy group, a 3-phenanthryloxy group, a 9-phenanthryloxy group, and the like, examples of the arylthioxy group include a phenylthioxy group, a 2-methylphenylthioxy group, a 4-tert-butylphenylthioxy group, and the like, and examples of the arylsulfoxy group include a benzenesulfoxy group, a p-toluenesulfoxy group, and the like, but the examples are not limited thereto.

In the present specification, examples of an arylamine group include a substituted or unsubstituted monoarylamine group, a substituted or unsubstituted diarylamine group, or a substituted or unsubstituted triarylamine group. The aryl group in the arylamine group may be a monocyclic aryl group or a polycyclic aryl group. The arylamine group including two or more aryl groups may include a monocyclic aryl group, a polycyclic aryl group, or both a monocyclic aryl group and a polycyclic aryl group. For example, the aryl group in the arylamine group may be selected from the above-described examples of the aryl group.

In the present specification, a heteroaryl group includes one or more atoms other than carbon, that is, one or more heteroatoms, and specifically, the heteroatom may include one or more atoms selected from the group consisting of O, N, Se, and S, and the like. The number of carbon atoms thereof is not particularly limited, but is preferably 2 to 30, and the heteroaryl group may be monocyclic or polycyclic. Examples of a hetero-cyclic group include a thiophene group, a furanyl group, a pyrrole group, an imidazolyl group, a thiazolyl group, an oxazolyl group, an oxadiazolyl group, a pyridyl group, a bipyridyl group, a pyrimidyl group, a triazinyl group, a triazolyl group, an acridyl group, a pyridazinyl group, a pyrazinyl group, a qinolinyl group, a quinazolinyl group, a quinoxalinyl group, a phthalazinyl group, a pyridopyrimidyl group, a pyridopyrazinyl group, a pyrazinopyrazinyl group, an isoquinolinyl group, an indolyl group, a carbazolyl group, a benzoxazolyl group, a benzimidazolyl group, a benzothiazolyl group, a benzocarbazolyl group, a benzothiophene group, a dibenzothiophene group, a benzofuranyl group, a phenanthrolinyl group (phenanthroline), an isoxazolyl group, a thiadiazolyl group, a phenothiazinyl group, a dibenzofuranyl group, and the like, but are not limited thereto.

In the present specification, examples of a heteroarylamine group include a substituted or unsubstituted monoheteroarylamine group, a substituted or unsubstituted diheteroarylamine group, or a substituted or unsubstituted triheteroarylamine group. The heteroarylamine group including two or more heteroaryl groups may include a monocyclic heteroaryl group, a polycyclic heteroaryl group, or both a monocyclic heteroaryl group and a polycyclic heteroaryl group. For example, the heteroaryl group in the heteroarylamine group may be selected from the above-described examples of the heteroaryl group.

In the present specification, examples of the heteroaryl group in the N-arylheteroarylamine group and the N-alkylheteroarylamine group are the same as the above-described examples of the heteroaryl group.

In the present specification, an arylene group means a group having two bonding positions in an aryl group, that is, a divalent group. The above-described description on the aryl group may be applied to the arylene group, except for a divalent arylene group.

In the present specification, a heteroarylene group means a group having two bonding positions in a heteroaryl group, that is, a divalent group. The above-described description on the heteroaryl group may be applied to the heteroarylene group, except for a divalent heteroarylene group.

According to an exemplary embodiment of the present specification, Chemical Formula 1 is represented by any one of the following Chemical Formulae 2 to 5.

[Chemical Formula 2]

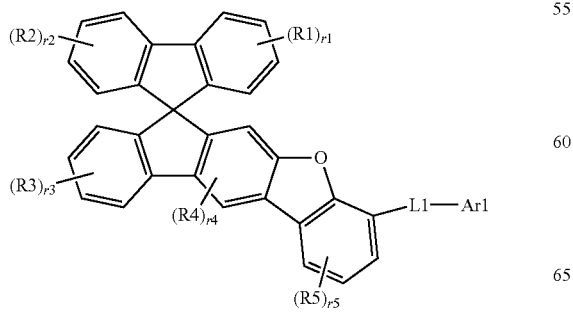

[Chemical Formula 3]

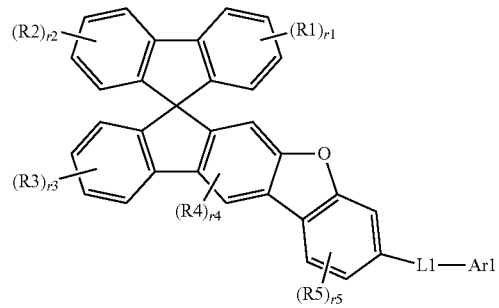

[Chemical Formula 4]

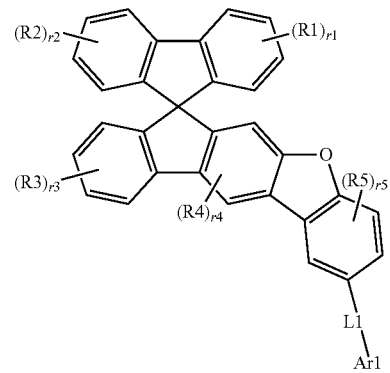

[Chemical Formula 5]

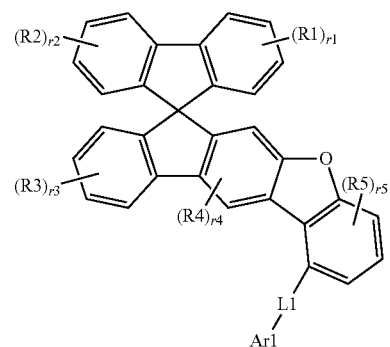

In Chemical Formulae 2 to 5,
the definitions of R1 to R5, r1 to r5, L1, and Ar1 are the same as those in Chemical Formula 1.

According to an exemplary embodiment of the present specification, Chemical Formula 1 is represented by the following Chemical Formula 6.

[Chemical Formula 6]

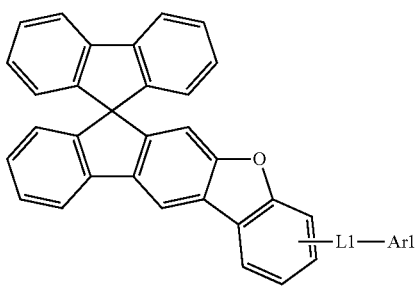

In Chemical Formula 6, the definitions of L1 and Ar1 are the same as those in Chemical Formula 1.

According to an exemplary embodiment of the present specification, Chemical Formula 1 is represented by any one of the following Chemical Formulae 7 to 10.

[Chemical Formula 7]

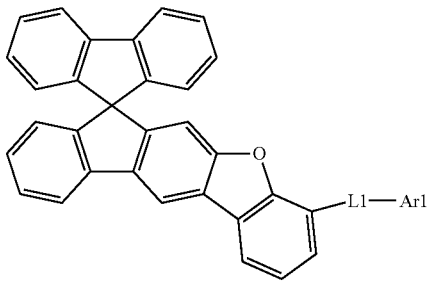

[Chemical Formula 8]

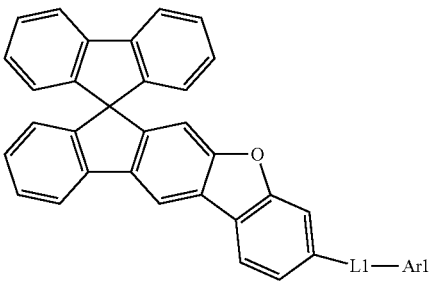

[Chemical Formula 9]

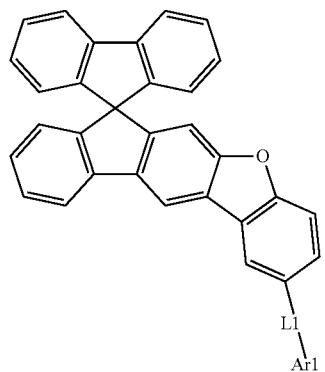

[Chemical Formula 10]

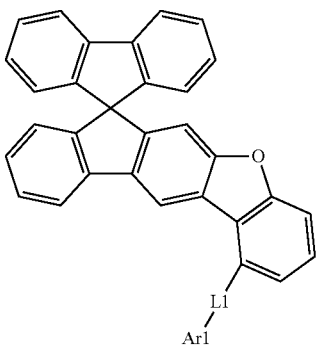

In Chemical Formulae 7 to 10, the definitions of L1 and Ar1 are the same as those in Chemical Formula 1.

According to an exemplary embodiment of the present specification, in Chemical Formula 1, L1 is a direct bond; an arylene group; or a heteroarylene group.

According to an exemplary embodiment of the present invention, in Chemical Formula 1, L1 is a direct bond; a substituted or unsubstituted phenylene group; a substituted or unsubstituted biphenylylene group; a substituted or unsubstituted naphthylene group; a substituted or unsubstituted terphenylene group; a substituted or unsubstituted quarterphenylene group; a substituted or unsubstituted anthracenylene group; a substituted or unsubstituted fluorenylene group; a substituted or unsubstituted phenanthrenylene group; a substituted or unsubstituted pyrenylene group; a substituted or unsubstituted triphenylenylene group; or a substituted or unsubstituted carbazolylene group.

According to an exemplary embodiment of the present specification, in Chemical Formula 1, L1 is a direct bond; a phenylene group; a biphenylylene group; a naphthylene group; a terphenylene group; a quarterphenylene group; an anthracenylene group; a fluorenylene group; a phenanthrenylene group; a pyrenylene group; a triphenylenylene group; or a carbazolylene group.

According to an exemplary embodiment of the present specification, in Chemical Formula 1, L1 may be any one of the following structures, but is not limited thereto.

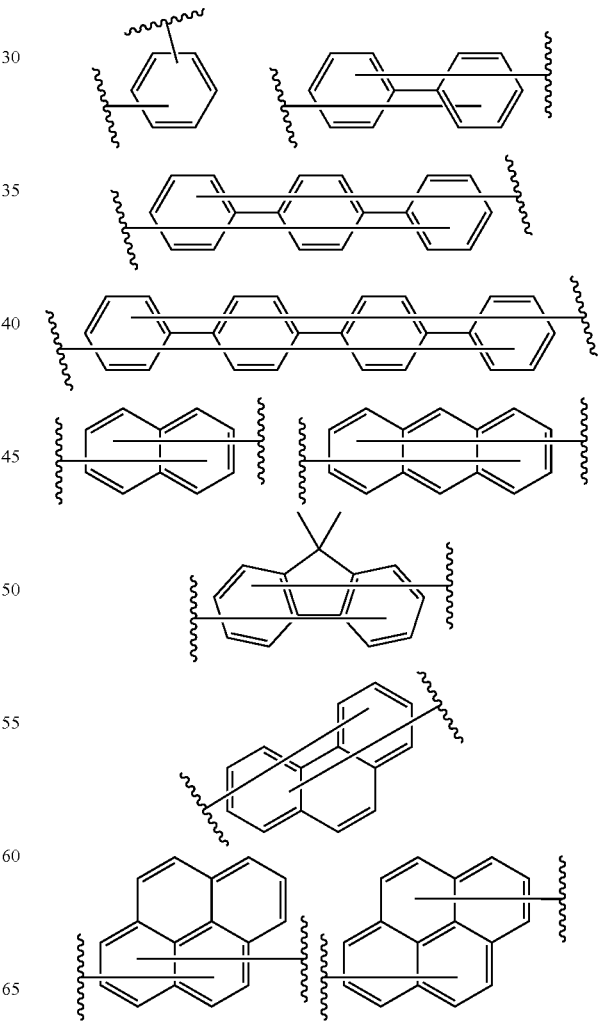

-continued

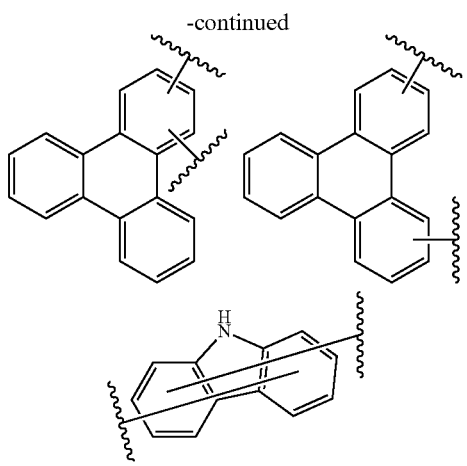

According to an exemplary embodiment of the present specification, in Chemical Formula 1, L1 is a direct bond; a phenylene group; an anthracenylene group; or a carbazolylene group.

According to an exemplary embodiment of the present specification, in Chemical Formula 1, Ar1 is selected from the group consisting of a substituted or unsubstituted silyl group; a substituted or unsubstituted phosphine oxide group; a substituted or unsubstituted aryl group; a substituted or unsubstituted quinolinyl group; a substituted or unsubstituted quinazolinyl group; a substituted or unsubstituted benzoxazolyl group; a substituted or unsubstituted quinoxalinyl group; a substituted or unsubstituted benzothiazolyl group; and a substituted or unsubstituted tricyclic or more heteroaryl group.

According to an exemplary embodiment of the present specification, in Chemical Formula 1, Ar1 is selected from the group consisting of a substituted or unsubstituted phenyl group; a substituted or unsubstituted biphenyl group; a substituted or unsubstituted phenanthrenyl group; a substituted or unsubstituted naphthyl group; a substituted or unsubstituted terphenyl group; a substituted or unsubstituted fluorenyl group; a substituted or unsubstituted anthracenyl group; a substituted or unsubstituted chrysenyl group; a substituted or unsubstituted quarterphenyl group; a substituted or unsubstituted spirobifluorenyl group; a substituted or unsubstituted pyrenyl group; a substituted or unsubstituted triphenylenyl group; a substituted or unsubstituted perylenyl group; a substituted or unsubstituted quinolinyl group; a substituted or unsubstituted quinazolinyl group; a substituted or unsubstituted benzoquinolinyl group; a substituted or unsubstituted phenanthrolinyl group; a substituted or unsubstituted quinoxalinyl group; a substituted or unsubstituted dibenzofuranyl group; a substituted or unsubstituted dibenzothiophene group; a substituted or unsubstituted benzonaphthofuranyl group; a substituted or unsubstituted benzonaphthothiophene group; a substituted or unsubstituted dimethylphosphine oxide group; a substituted or unsubstituted diphenylphosphine oxide group; a substituted or unsubstituted dinaphthylphosphine oxide group; a substituted or unsubstituted benzoxazolyl group; a substituted or unsubstituted benzothiazolyl group; a substituted or unsubstituted triphenylsilyl group; a substituted or unsubstituted phenothiazinyl group; a substituted or unsubstituted phenoxazinyl group; a substituted or unsubstituted thiophene group; a substituted or unsubstituted benzocarbazolyl group; a substituted or unsubstituted dibenzocarbazolyl group; a substituted or unsubstituted carbazolyl group; a substituted or unsubstituted

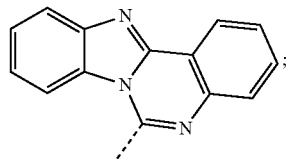

a substituted or unsubstituted

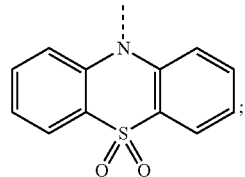

and a structure represented by the following Chemical Formula a, and

---- means a moiety bonded to Chemical Formula 1 via L1.

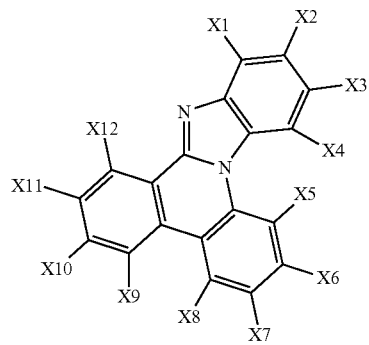

[Chemical Formula a]

In Chemical Formula a, any one of X1 to X12 is a moiety bonded to Chemical Formula 1 via L1, and the others are the same as or different from each other, and are each independently hydrogen; a substituted or unsubstituted alkyl group; a substituted or unsubstituted aryl group; or a substituted or unsubstituted heteroaryl group, or adjacent groups are linked to each other to form a substituted or unsubstituted ring.

According to an exemplary embodiment of the present specification, in Chemical Formula a, any one of X1 to X12 is a moiety bonded to Chemical Formula 1 via L1, and the others are hydrogen.

According to an exemplary embodiment of the present specification, in Chemical Formula a, X11 and X12 are linked to each other to form a substituted or unsubstituted monocyclic or polycyclic hydrocarbon ring having 6 to 20 carbon atoms.

According to an exemplary embodiment of the present specification, in Chemical Formula a, X11 and X12 are linked to each other to form a substituted or unsubstituted monocyclic or polycyclic hydrocarbon ring having 6 to 10 carbon atoms.

According to an exemplary embodiment of the present specification, in Chemical Formula a, X11 and X12 are linked to each other to form a substituted or unsubstituted benzene ring.

According to an exemplary embodiment of the present specification, in Chemical Formula a, X11 and X12 are linked to each other to form a benzene ring.

According to an exemplary embodiment of the present specification, in Chemical Formula 1, Ar1 is selected from the group consisting of a phenyl group; a biphenyl group; a phenanthrenyl group; a naphthyl group; a terphenyl group; a fluorenyl group; an anthracenyl group; a chrysenyl group; a quarterphenyl group; a spirobifluorenyl group; a pyrenyl group; a triphenylenyl group; a perylenyl group; a quinolinyl group; a quinazolinyl group; a benzoquinolinyl group; a phenanthrolinyl group; a quinoxalinyl group; a dibenzofuranyl group; a dibenzothiophene group; benzonaphthofuranyl group; a benzonaphthothiophene group; a dimethylphosphine oxide group; diphenylphosphine oxide group; dinaphthylphosphine oxide group; a benzoxazolyl group; a benzothiazolyl group; a triphenylsilyl group; a phenothiazinyl group; a phenoxazinyl group; a thiophene group; a benzocarbazolyl group; a dibenzocarbazolyl group; a carbazolyl group;

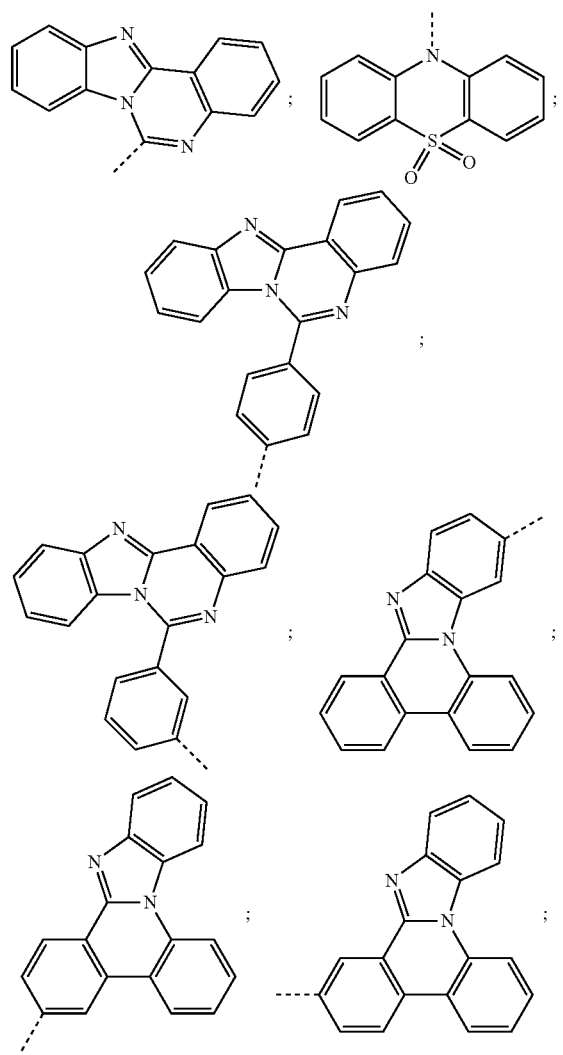

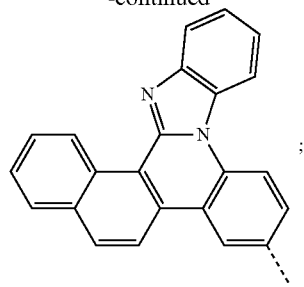

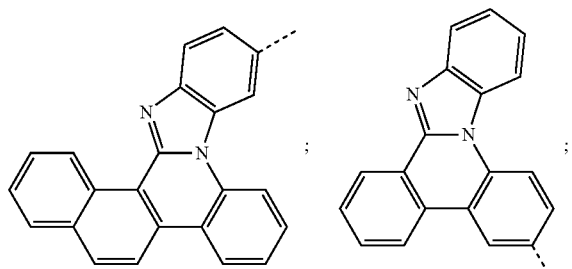

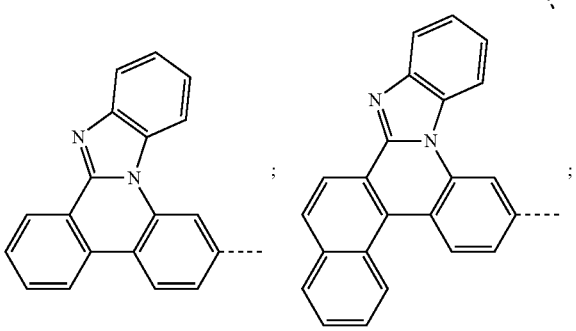

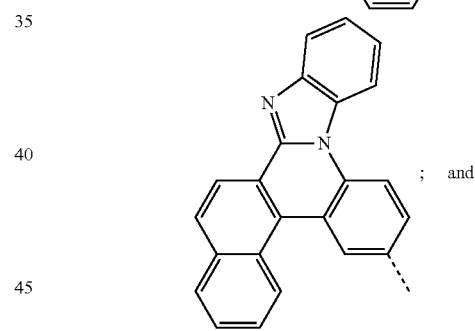

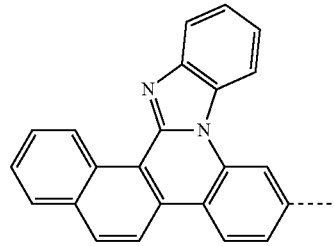

and

Ar1 may be unsubstituted or substituted with one or more selected from the group consisting of deuterium; a fluorine group; a nitrile group; a methyl group; a t-butyl group; a phenyl group; a biphenyl group; a naphthyl group; a fluorenyl group; a phenanthrenyl group; a carbazolyl group; a benzocarbazolyl group; a pyridyl group; a triazinyl group; a triphenylenyl group; a pyrimidyl group; a quinolinyl group; a dibenzofuranyl group; a dibenzothiophene group; a benzimidazolyl group; a benzothiazolyl group; a benzoxazolyl group; a thiophene group; a dimethylphosphine oxide group; a diphenylphosphine oxide group; a dinaphthylphosphine oxide group; a trimethylsilyl group; a triphenylsilyl group; and

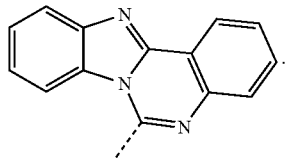

---- means a moiety bonded to Chemical Formula 1 via L1.

According to an exemplary embodiment of the present specification, in Chemical Formula 1, Ar1 is represented by any one of the following Structural Formulae [A-1] to [A-1].

[A-1]

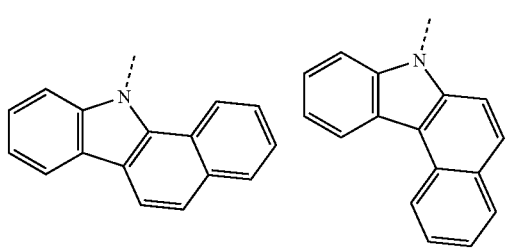

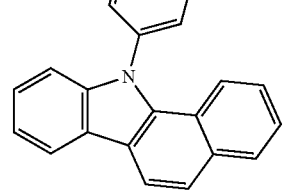

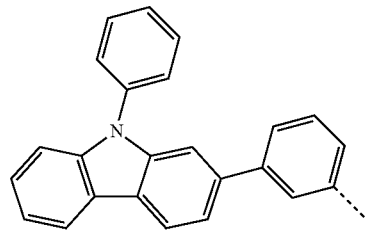

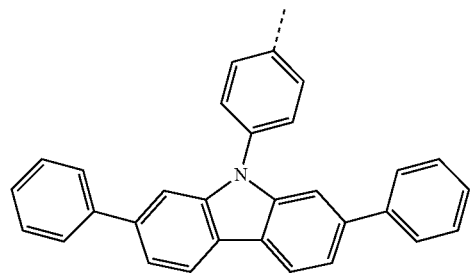

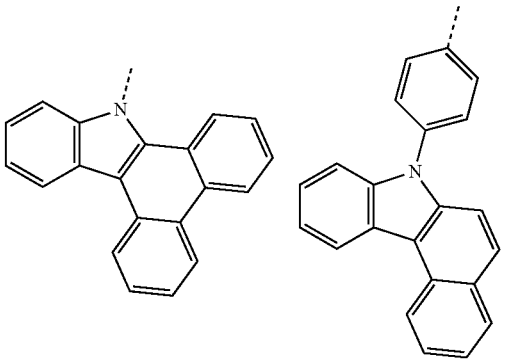

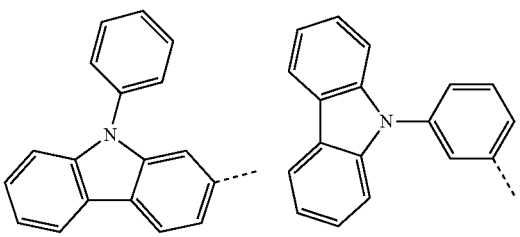

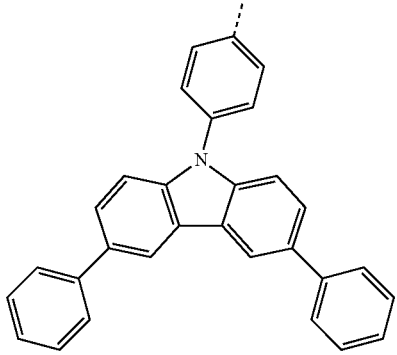

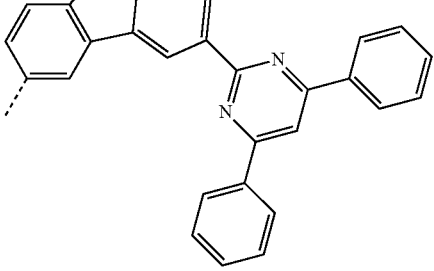

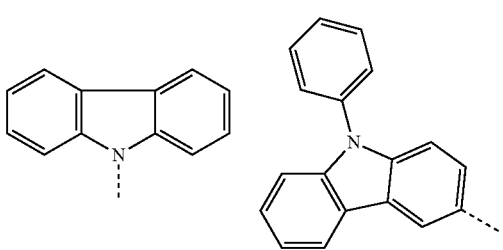

-continued
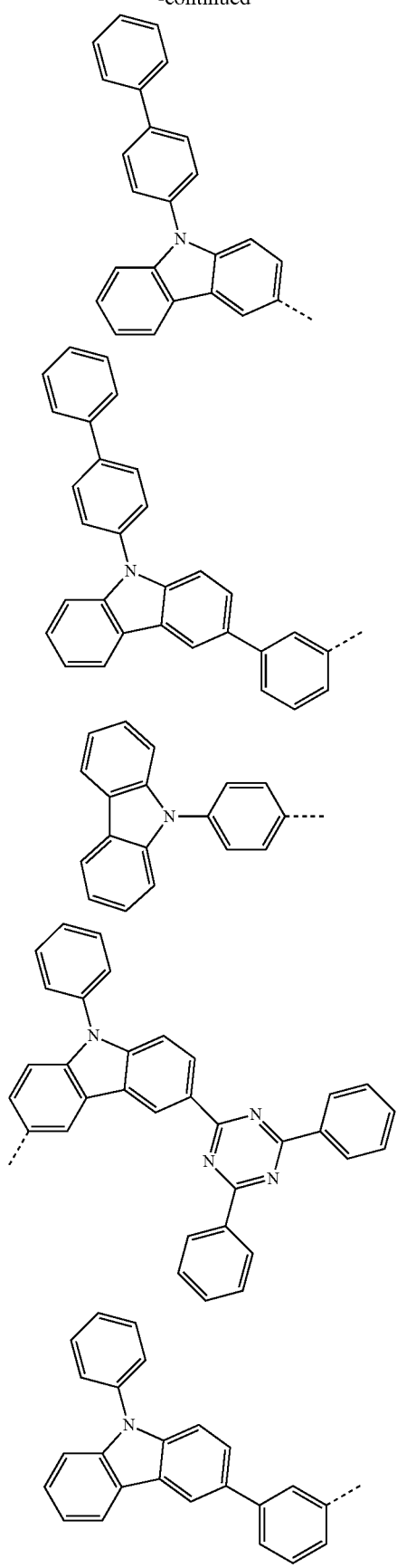
-continued
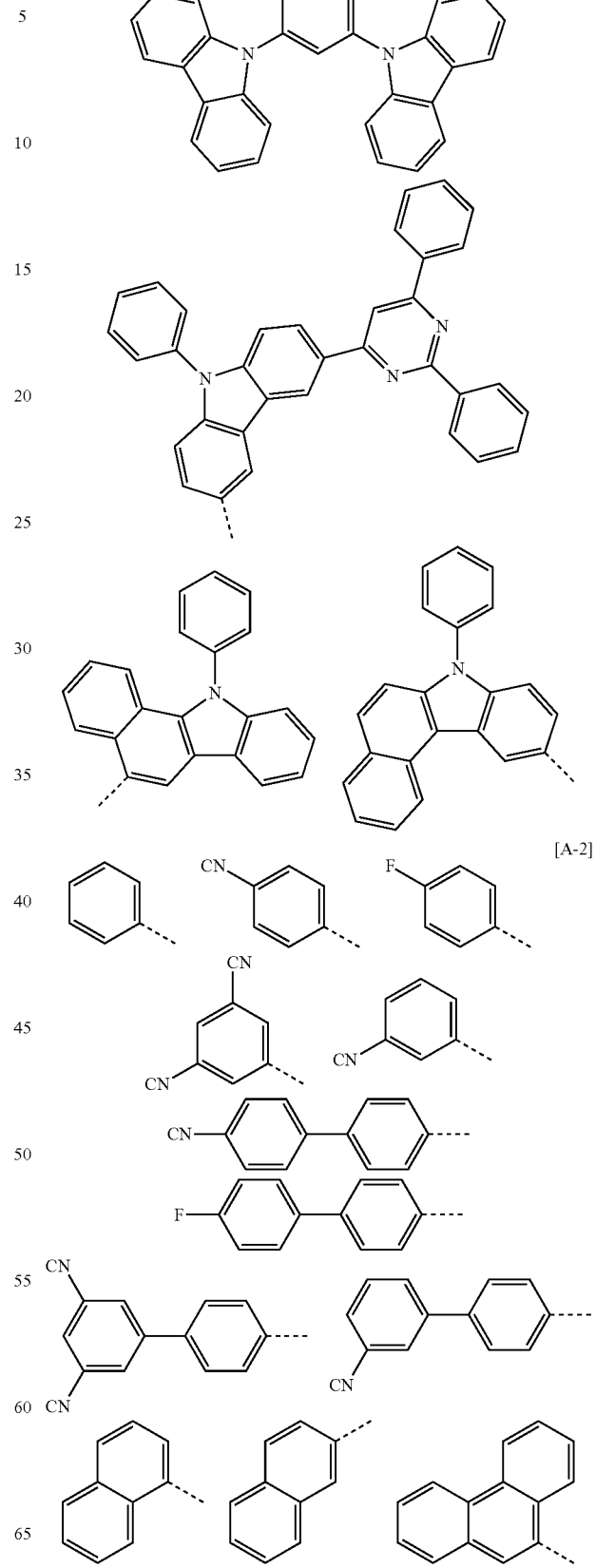

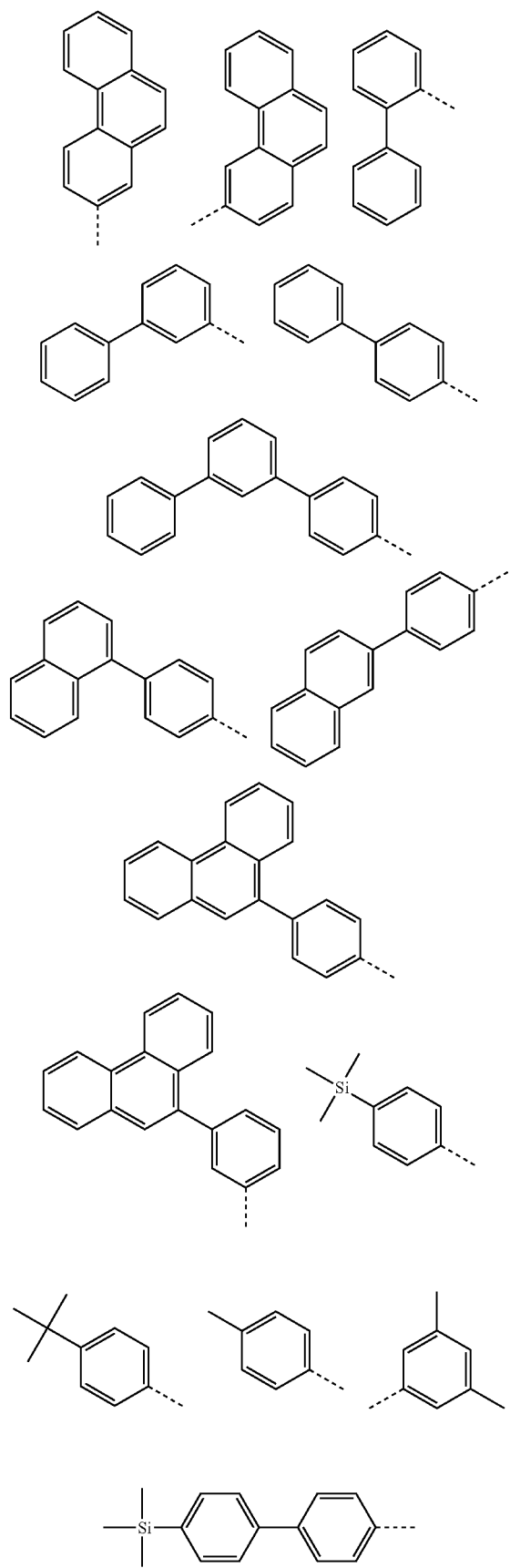
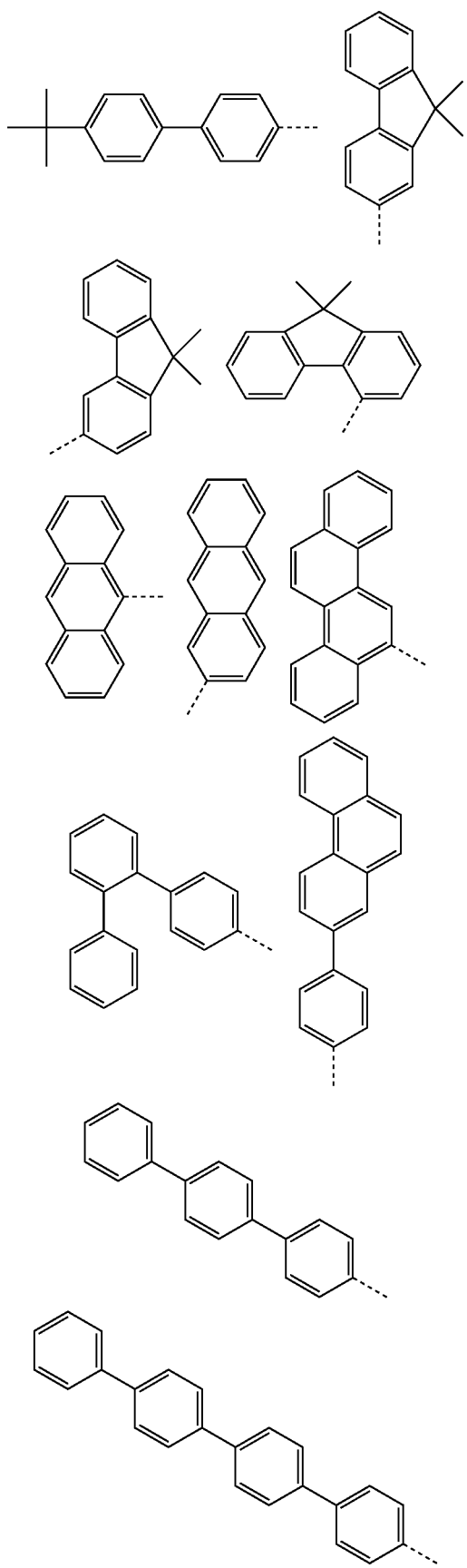

-continued
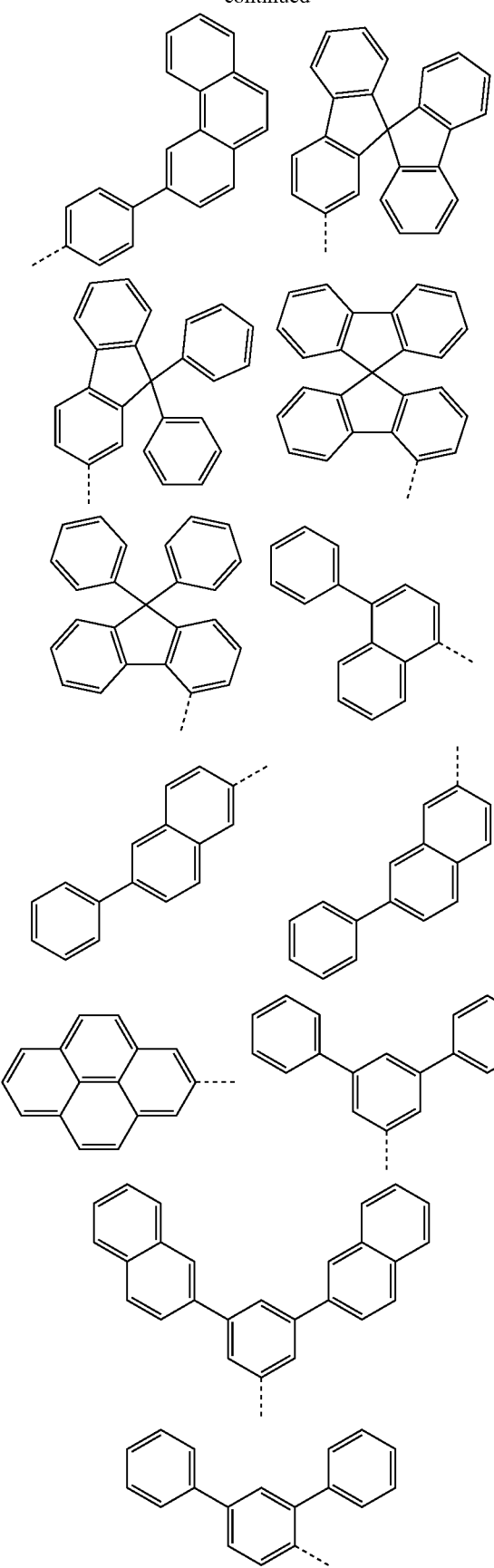
-continued
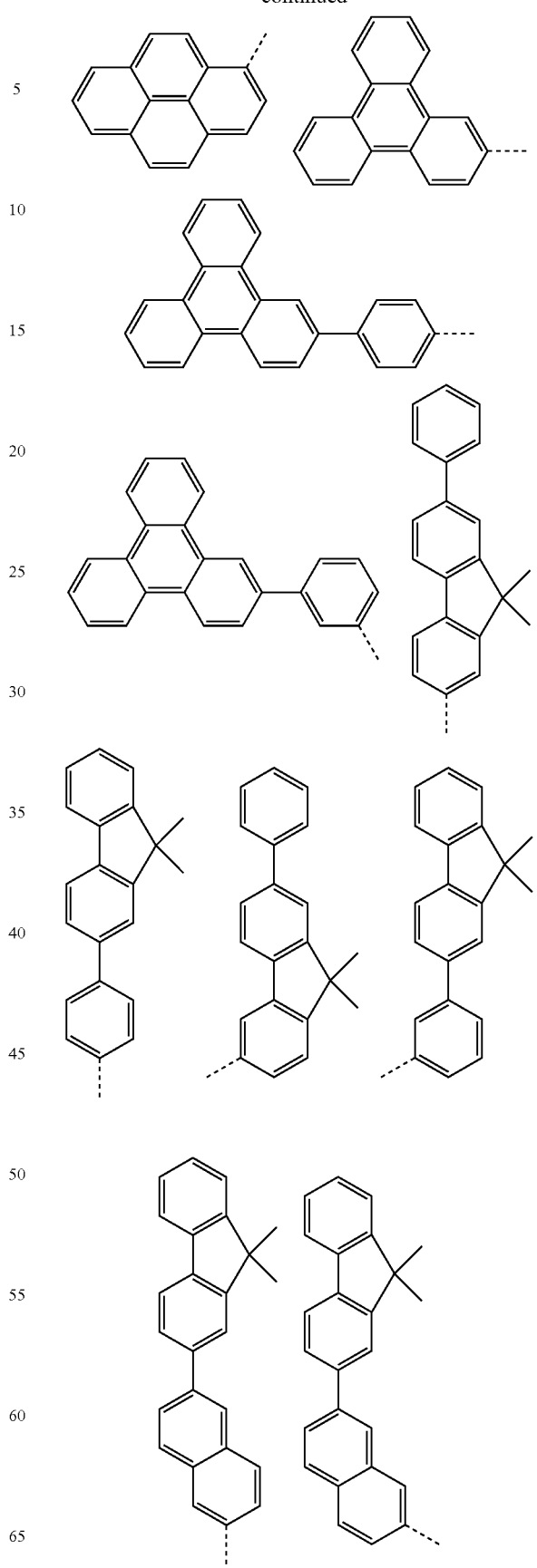

-continued
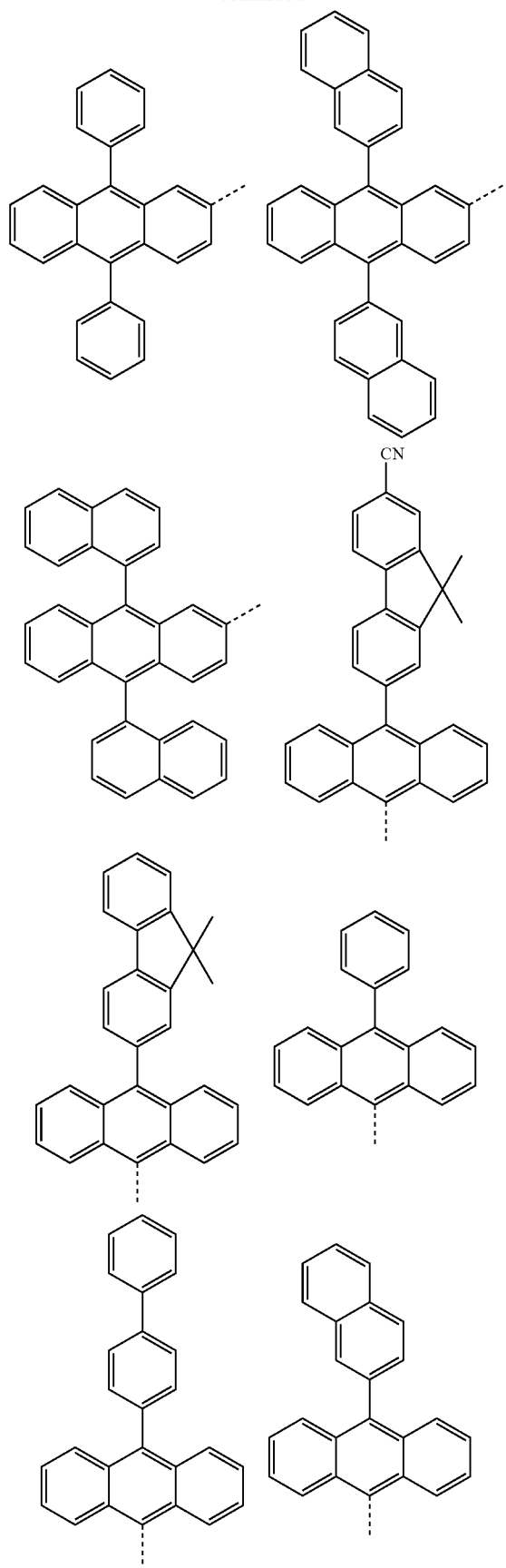
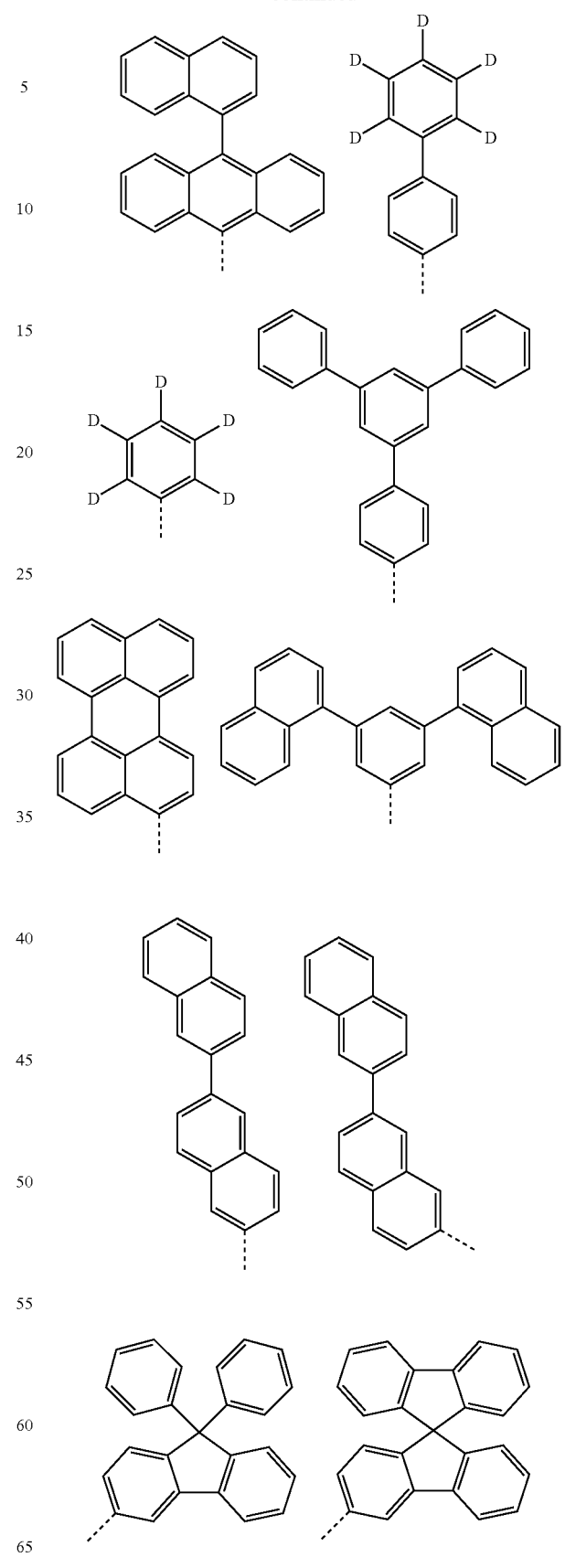

[A-3]
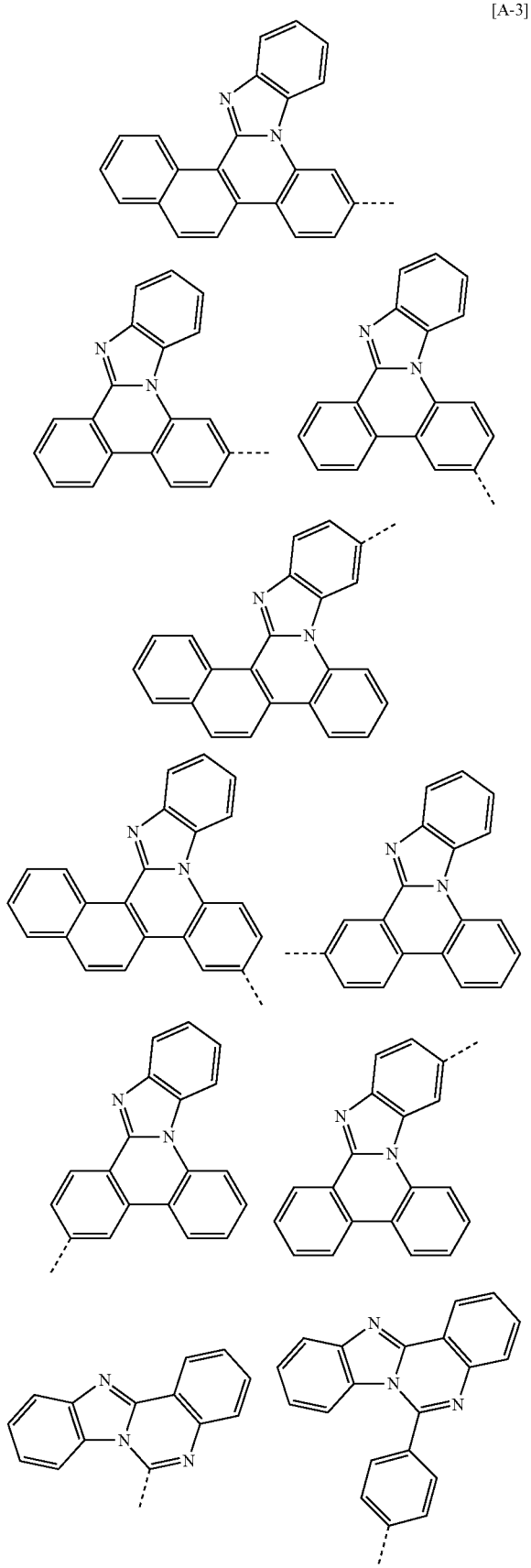
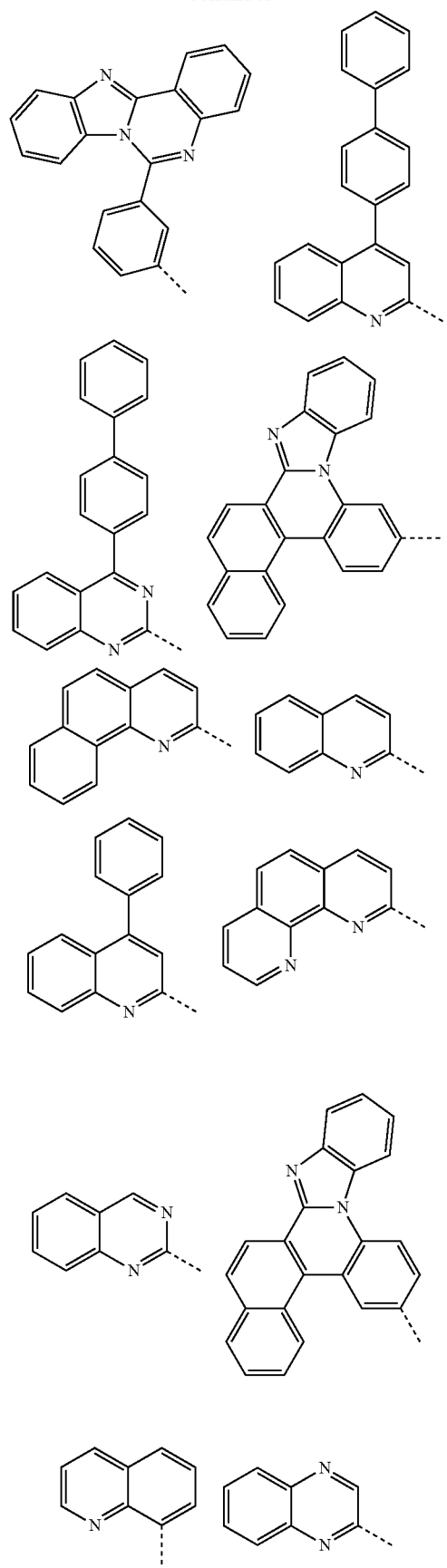

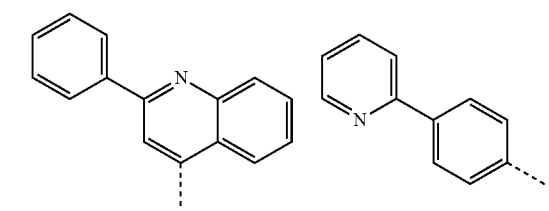
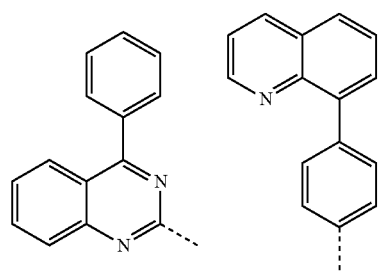
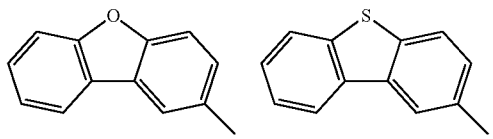
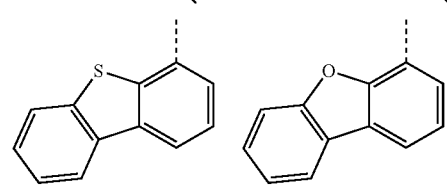
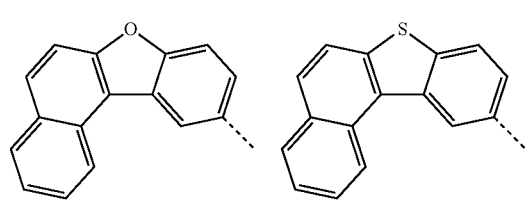
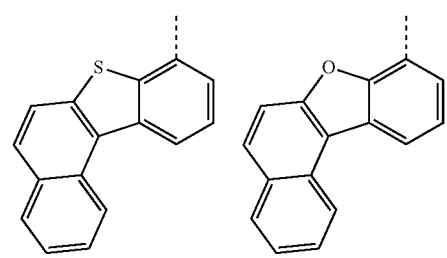
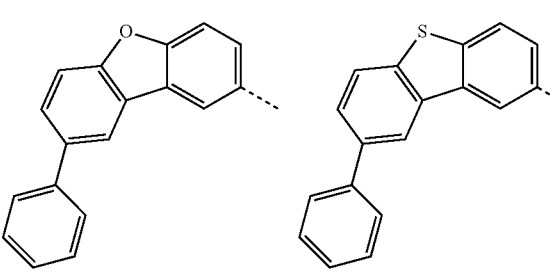
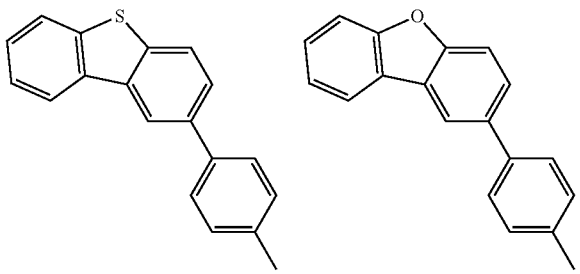
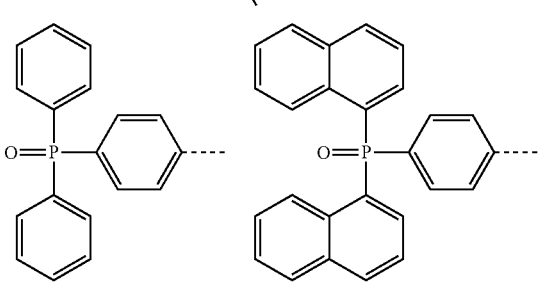
[A-4]
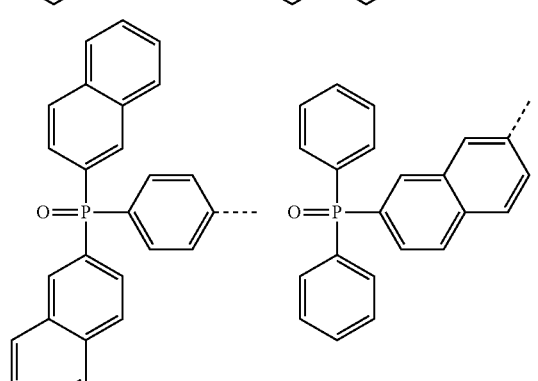
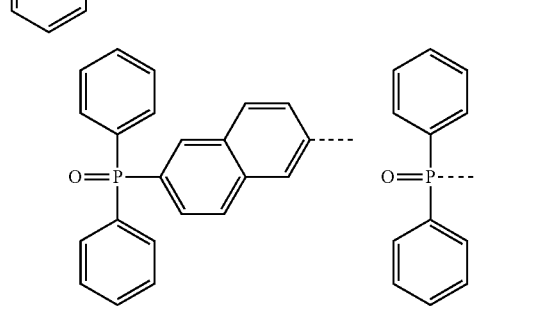
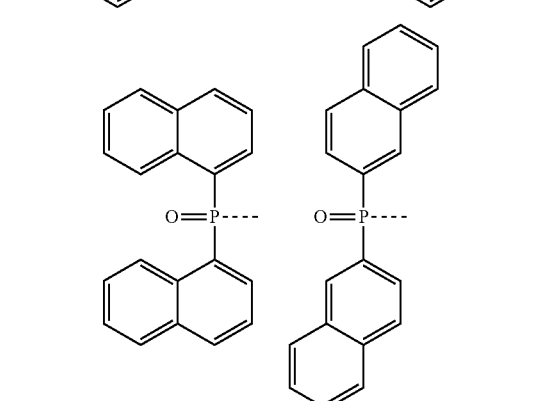
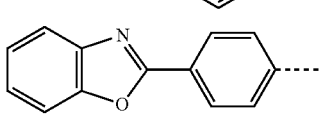

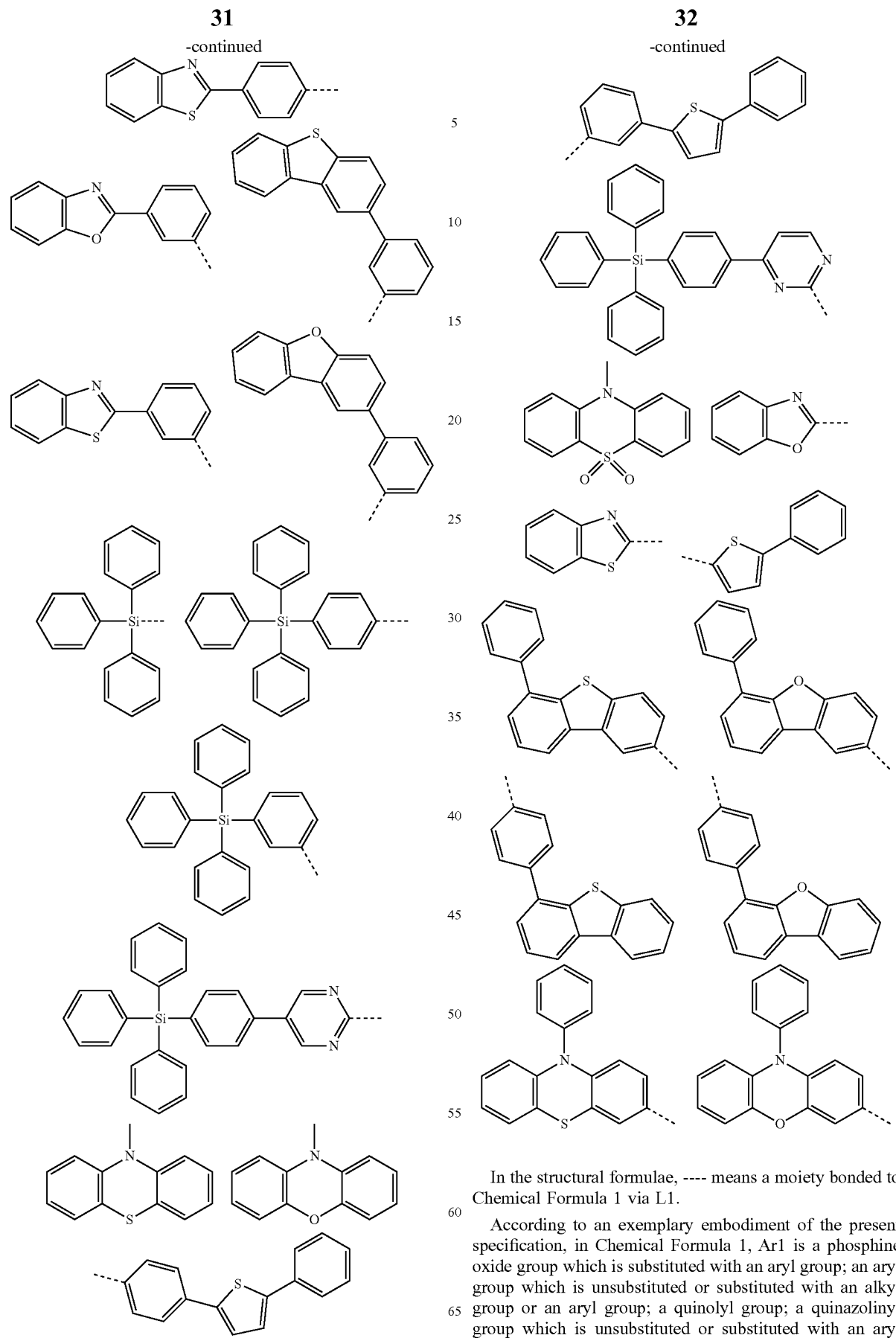

In the structural formulae, ---- means a moiety bonded to Chemical Formula 1 via L1.

According to an exemplary embodiment of the present specification, in Chemical Formula 1, Ar1 is a phosphine oxide group which is substituted with an aryl group; an aryl group which is unsubstituted or substituted with an alkyl group or an aryl group; a quinolyl group; a quinazolinyl group which is unsubstituted or substituted with an aryl group; or a tricyclic or more heteroaryl group which is unsubstituted or substituted with an aryl group or a heteroaryl group which is unsubstituted or substituted with an aryl group.

According to an exemplary embodiment of the present specification, in Chemical Formula 1, Ar1 is a phosphine oxide group which is substituted with an aryl group; a phenyl group; a biphenyl group; a naphthyl group; a terphenyl group; a fluorenyl group which is substituted with an alkyl group; a triphenylenyl group; a dibenzofuranyl group; a dibenzothiophene group; a quinazolinyl group which is unsubstituted or substituted with an aryl group; a quinolyl group; a benzocarbazolyl group; or a carbazolyl group which is unsubstituted or substituted with a heteroaryl group substituted with an aryl group.

According to an exemplary embodiment of the present specification, in Chemical Formula 1, Ar1 is a phosphine oxide group which is substituted with a phenyl group; a phenyl group; a biphenyl group; a naphthyl group; a terphenyl group; a fluorenyl group which is substituted with a methyl group; a triphenylenyl group; a pyridyl group which is unsubstituted or substituted with a phenyl group; a pyrimidyl group which is unsubstituted or substituted with a phenyl group; a triazinyl group which is unsubstituted or substituted with a phenyl group or a biphenyl group; a dibenzofuranyl group; a dibenzothiophene group; a quinazolyl group which is unsubstituted or substituted with a phenyl group, a biphenyl group, or a naphthyl group; a quinolyl group; a benzocarbazolyl group; or a carbazolyl group which is unsubstituted or substituted with a triazinyl group substituted with a phenyl group, a pyrimidyl group substituted with a phenyl group, a pyridyl group substituted with a phenyl group, or a quinazolinyl group substituted with a phenyl group.

According to an exemplary embodiment of the present specification, in Chemical Formula 1, Ar1 is a phosphine oxide group which is substituted with a phenyl group; a phenyl group; a biphenyl group; a naphthyl group; a fluorenyl group which is substituted with a methyl group; a triphenylenyl group; a pyridyl group which is unsubstituted or substituted with a phenyl group; a pyrimidyl group which is unsubstituted or substituted with a phenyl group; a triazinyl group which is unsubstituted or substituted with a phenyl group or a biphenyl group; a dibenzofuranyl group; a dibenzothiophene group; a quinazolyl group which is unsubstituted or substituted with a phenyl group, a biphenyl group, or a naphthyl group; a quinolyl group; a benzocarbazolyl group; or a carbazolyl group which is unsubstituted or substituted with a triazinyl group substituted with a phenyl group, a pyrimidyl group substituted with a phenyl group, or a pyridyl group substituted with a phenyl group.

According to an exemplary embodiment of the present specification, Chemical Formula 1 is any one selected from the following compounds.

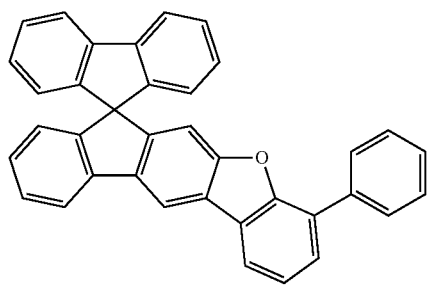

-continued

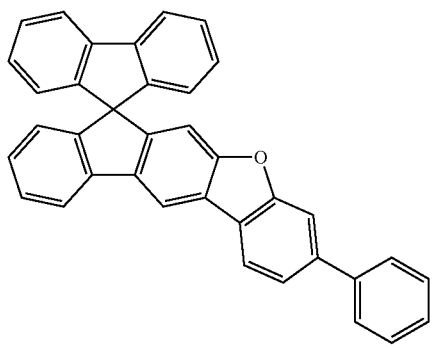

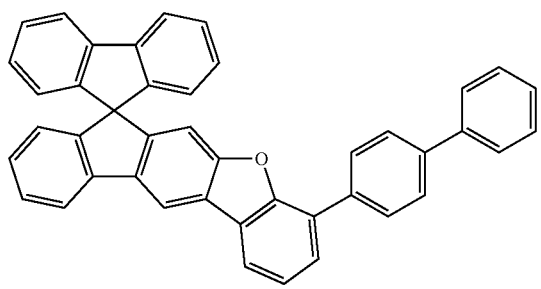

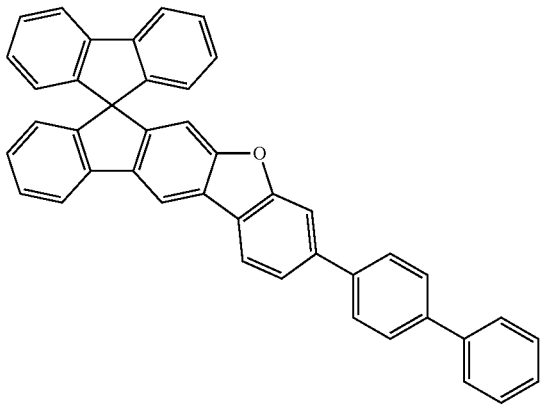

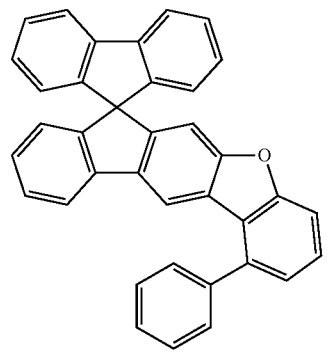

35
-continued
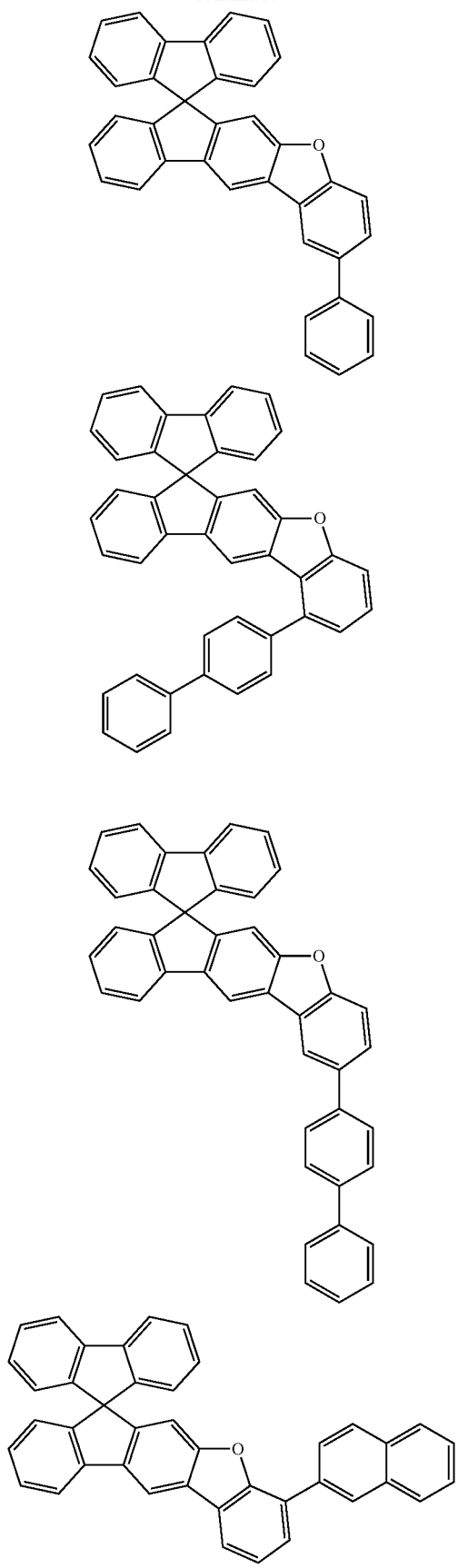
36
-continued
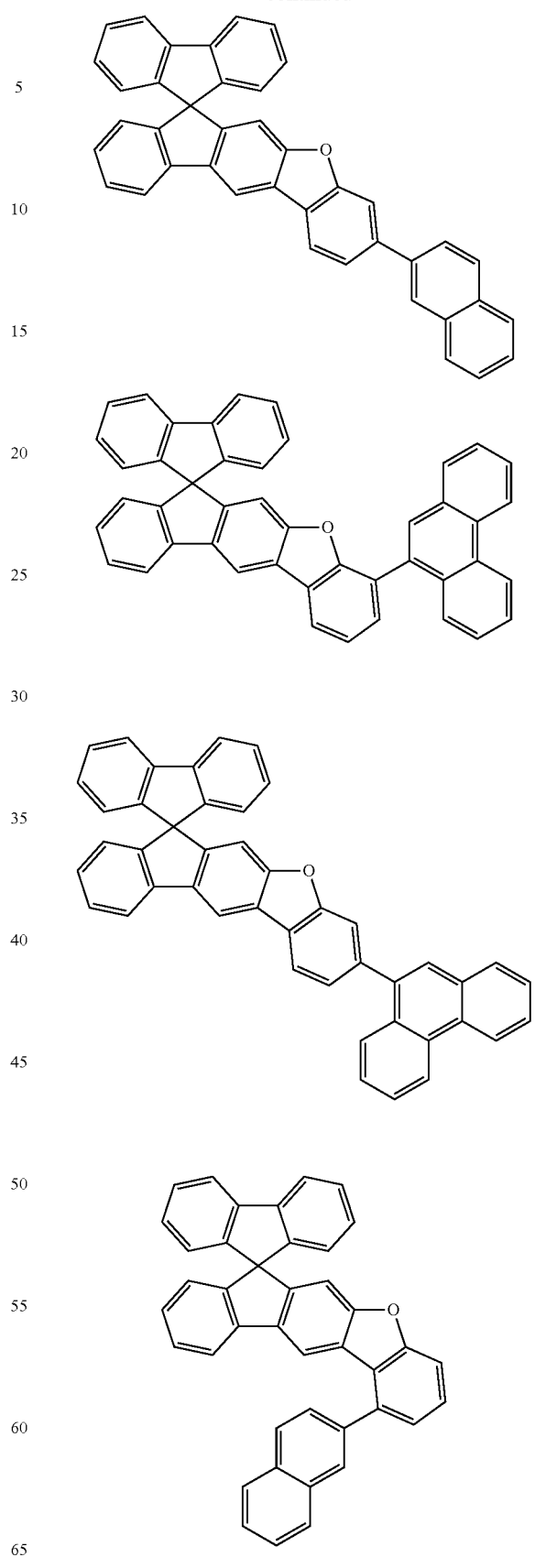

37
-continued
38
-continued
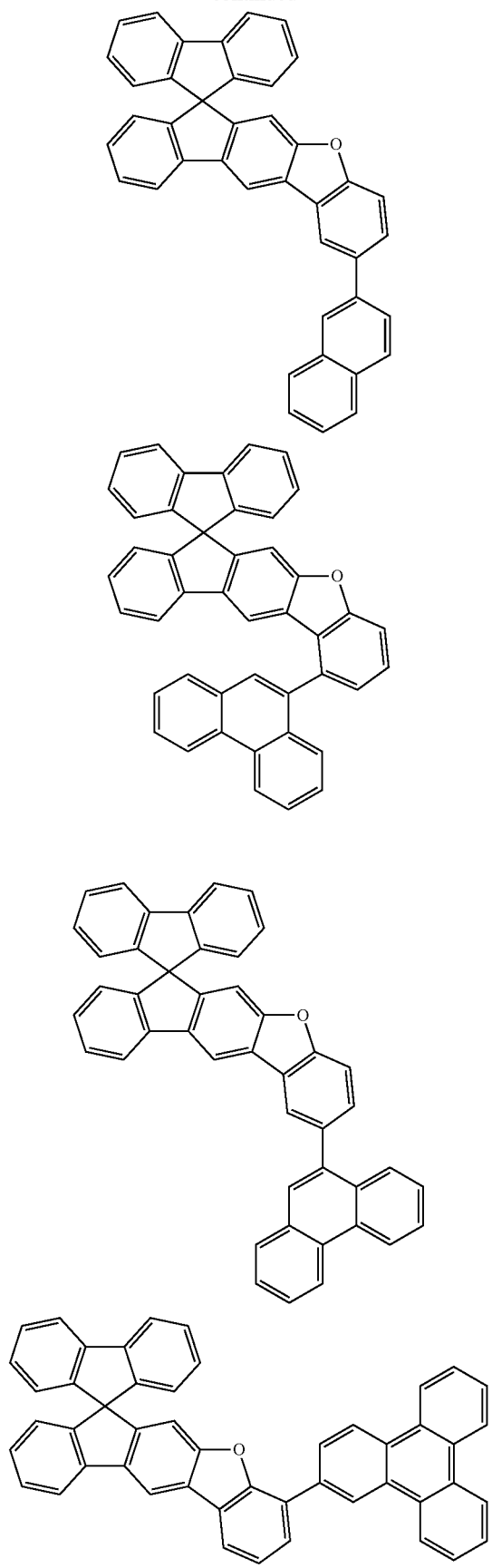
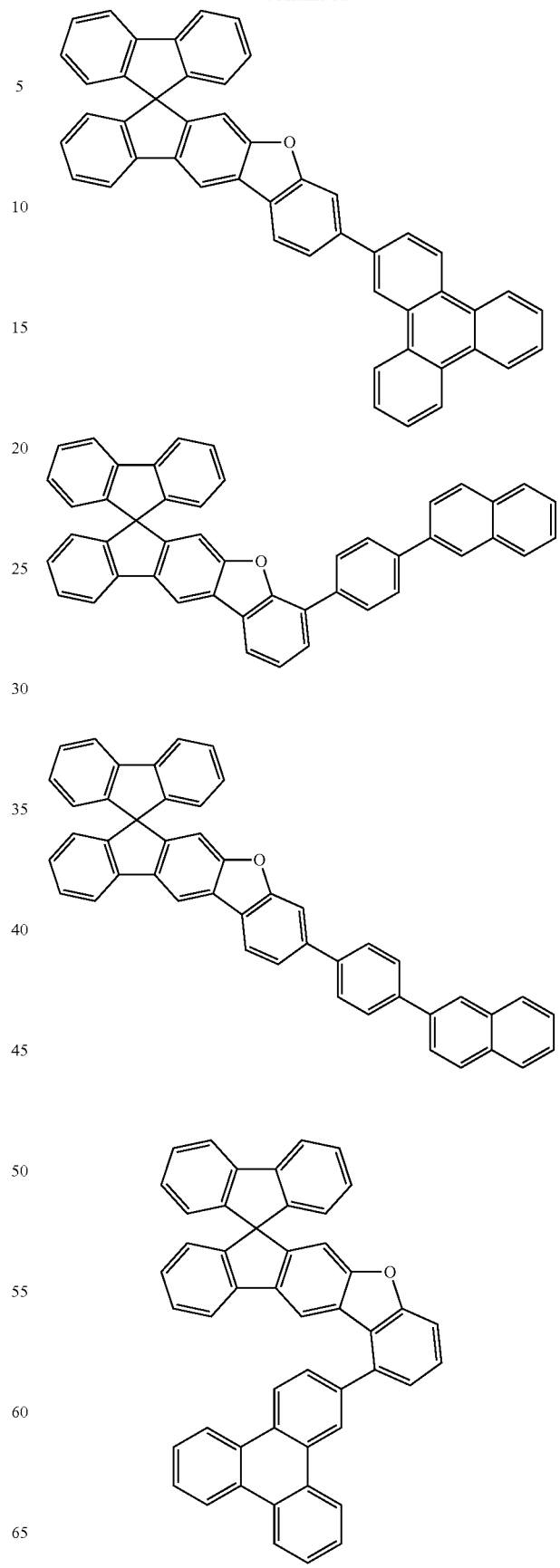

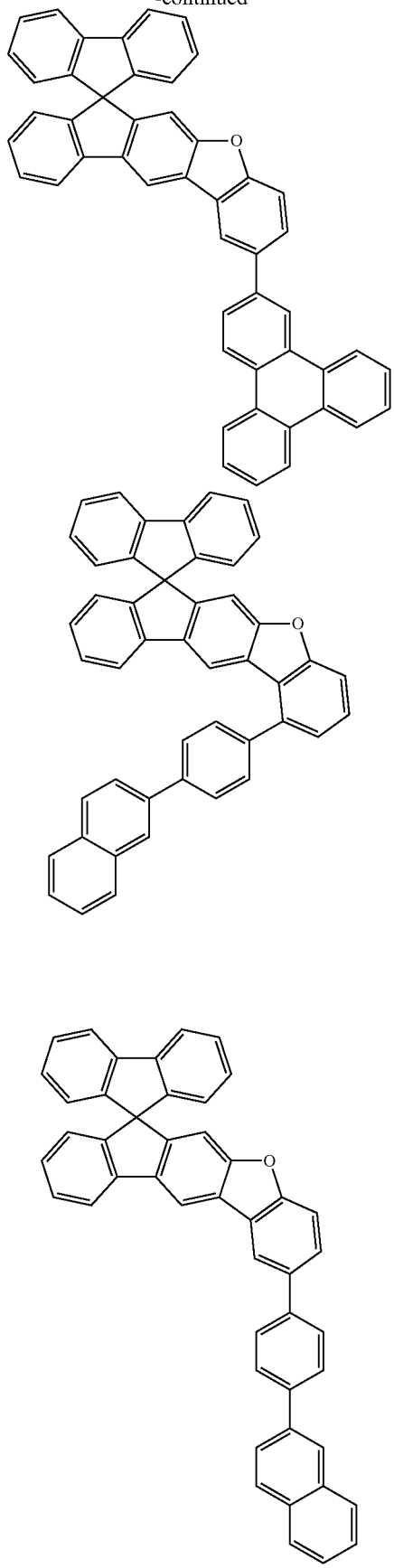
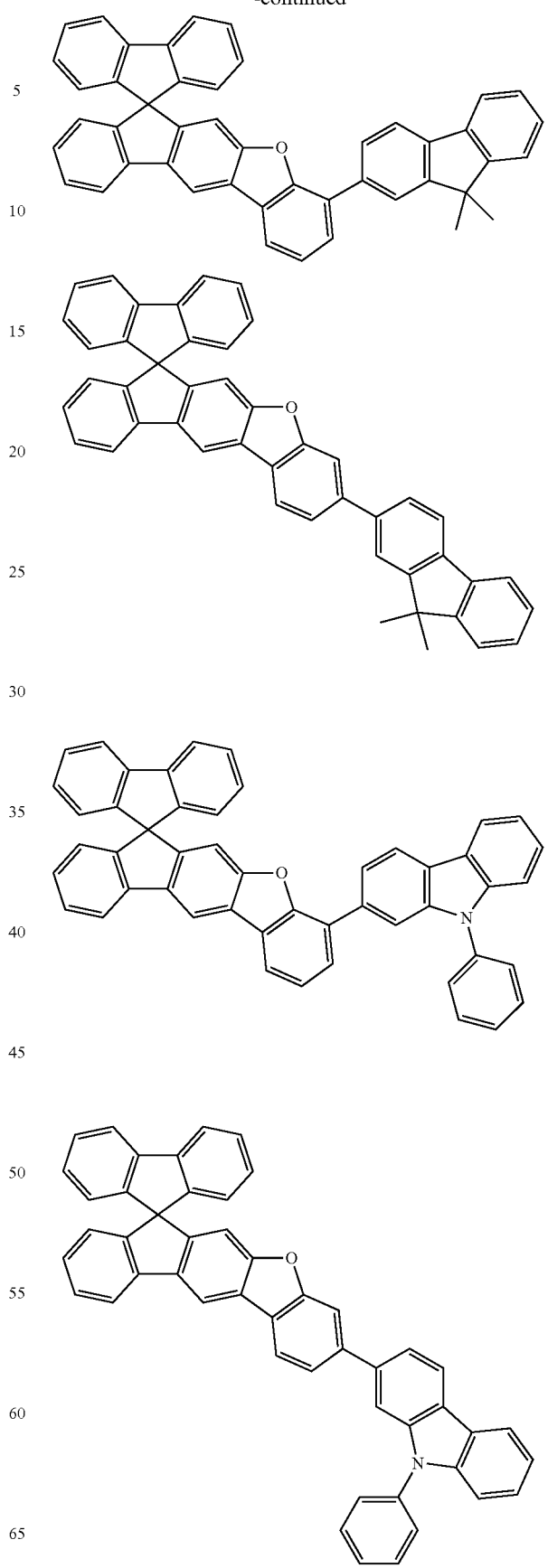

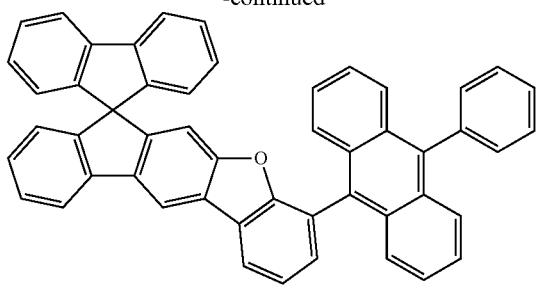
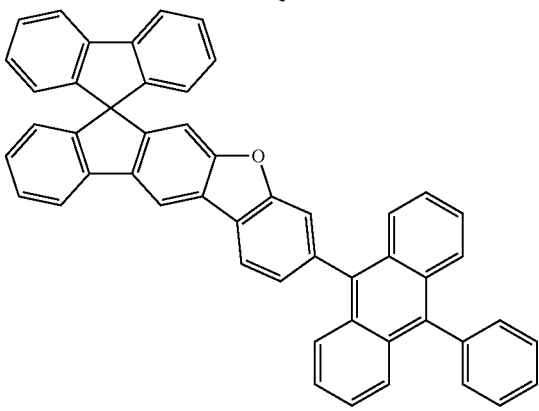
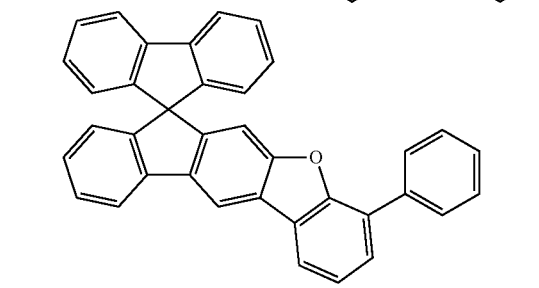
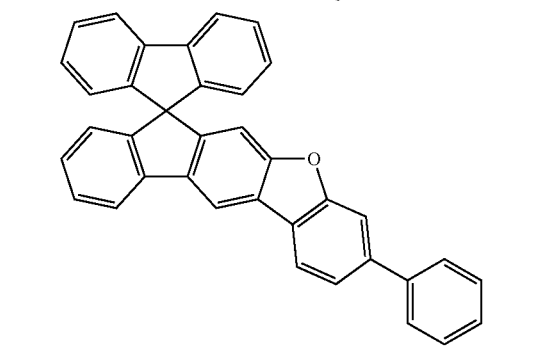
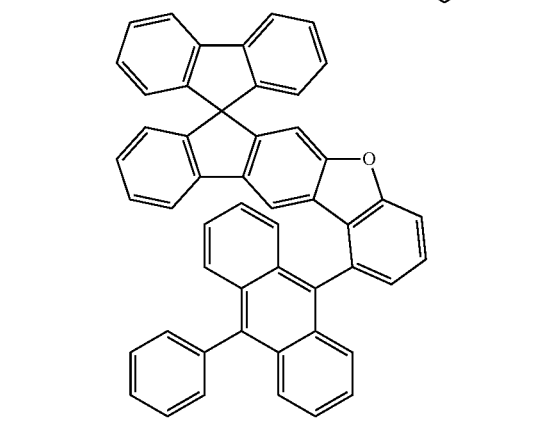
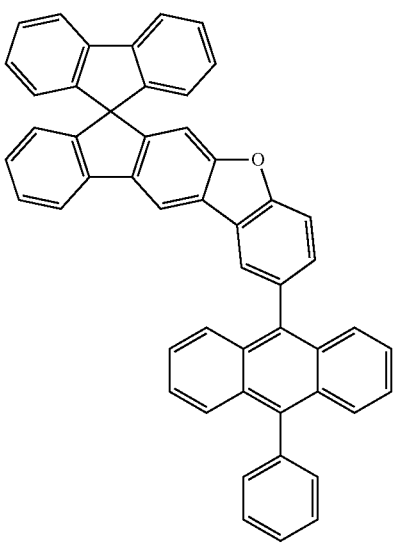
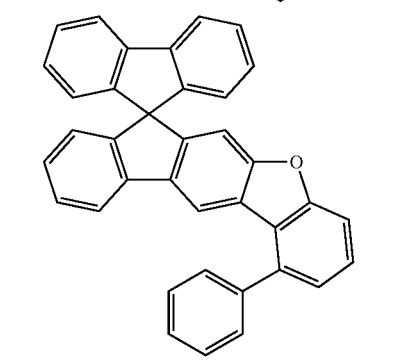
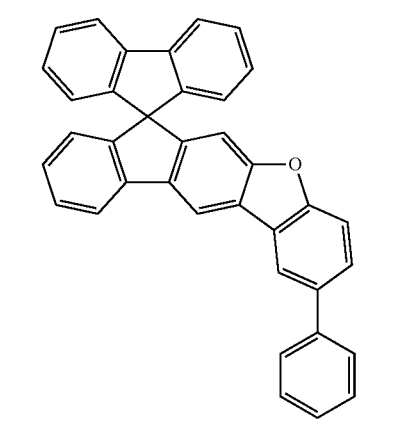
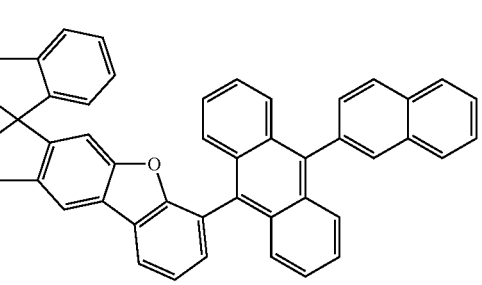

-continued
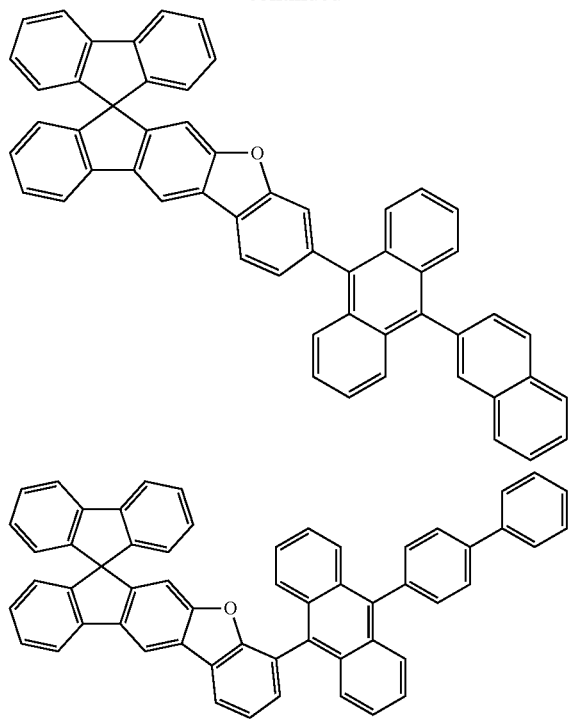
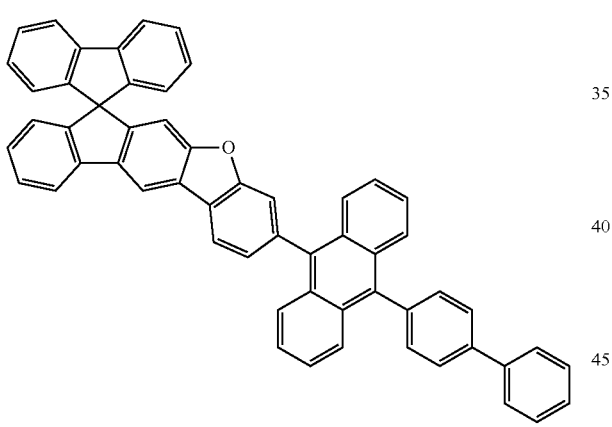
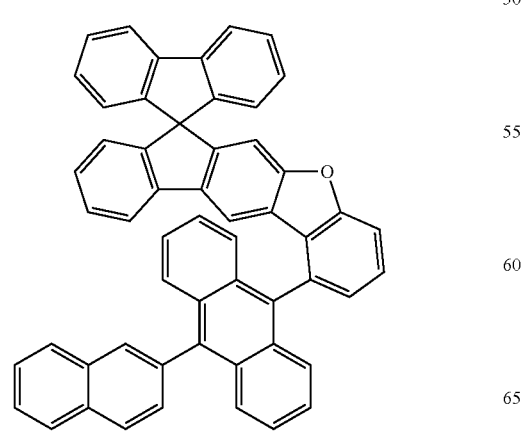
-continued
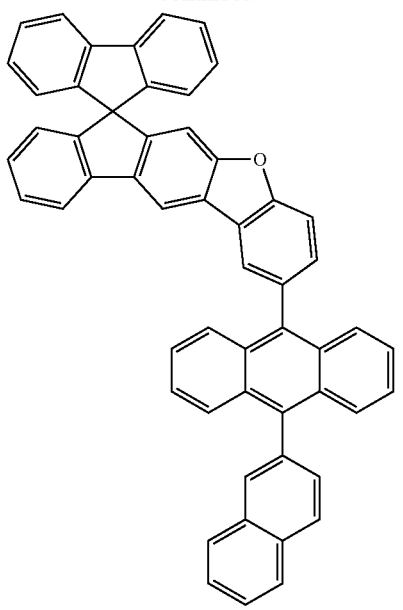
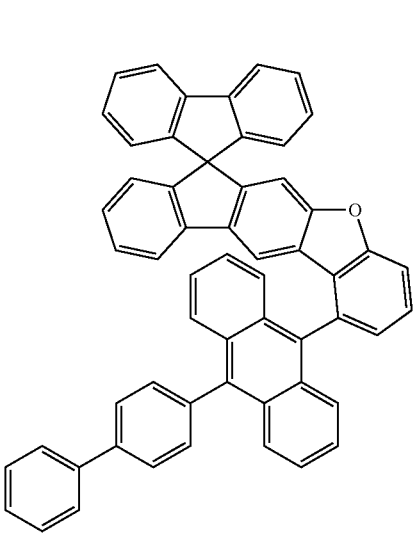

45
-continued
46
-continued
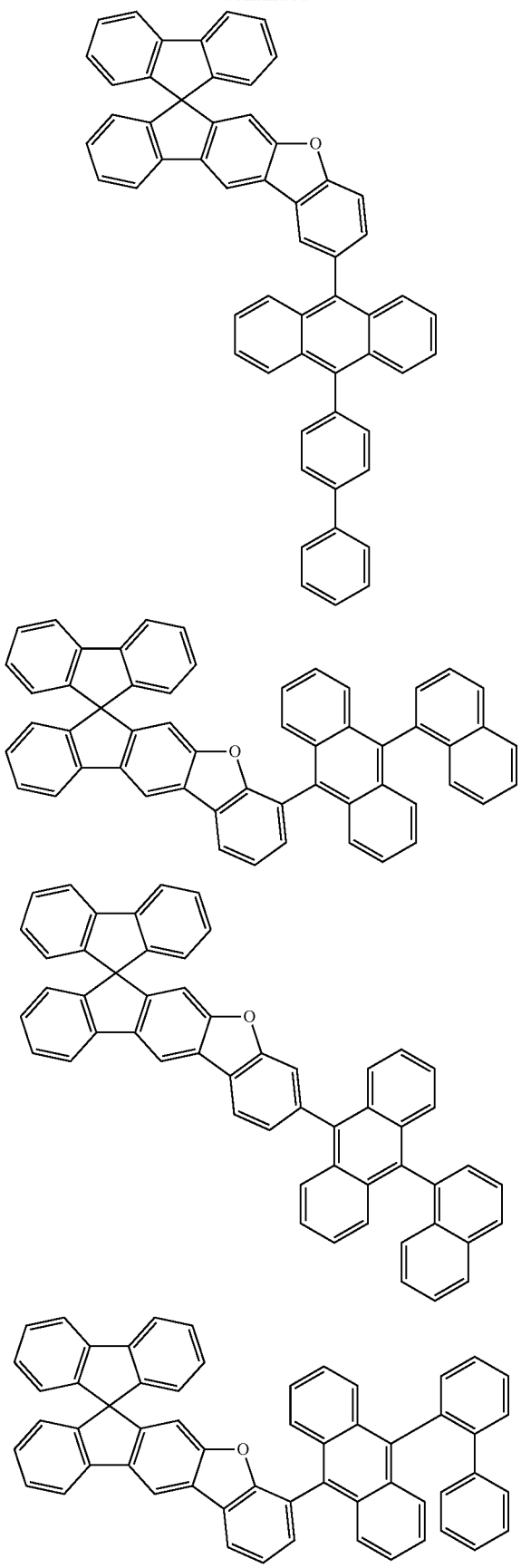
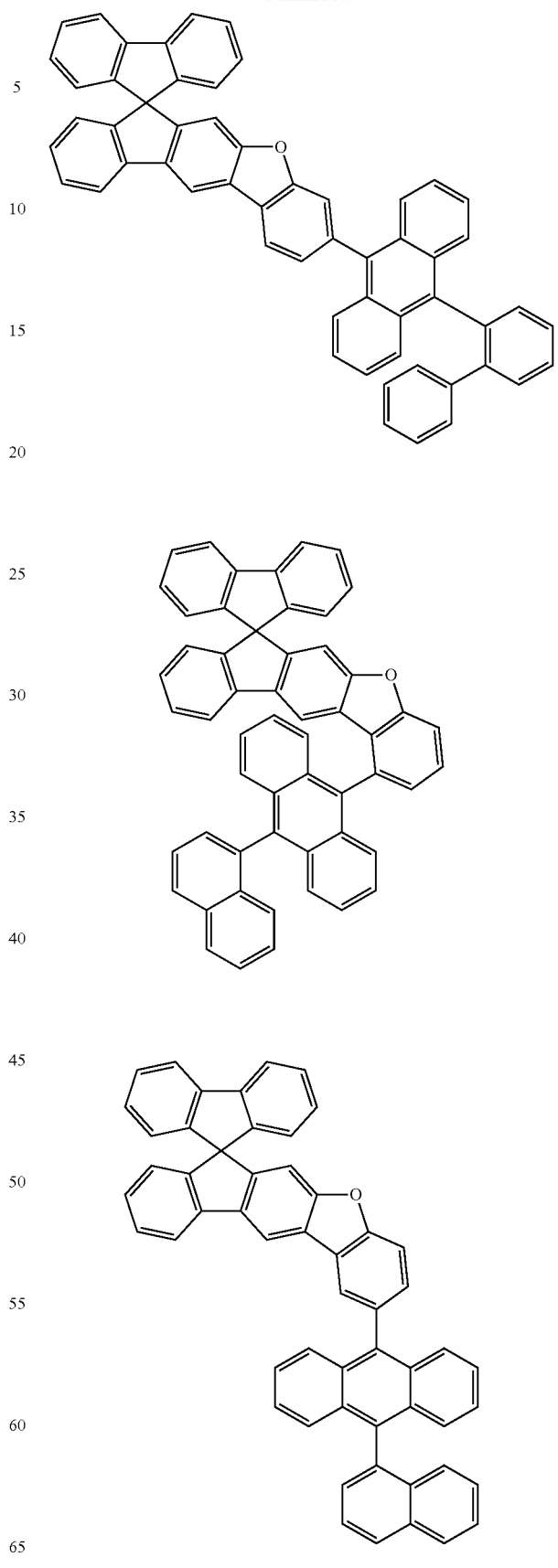

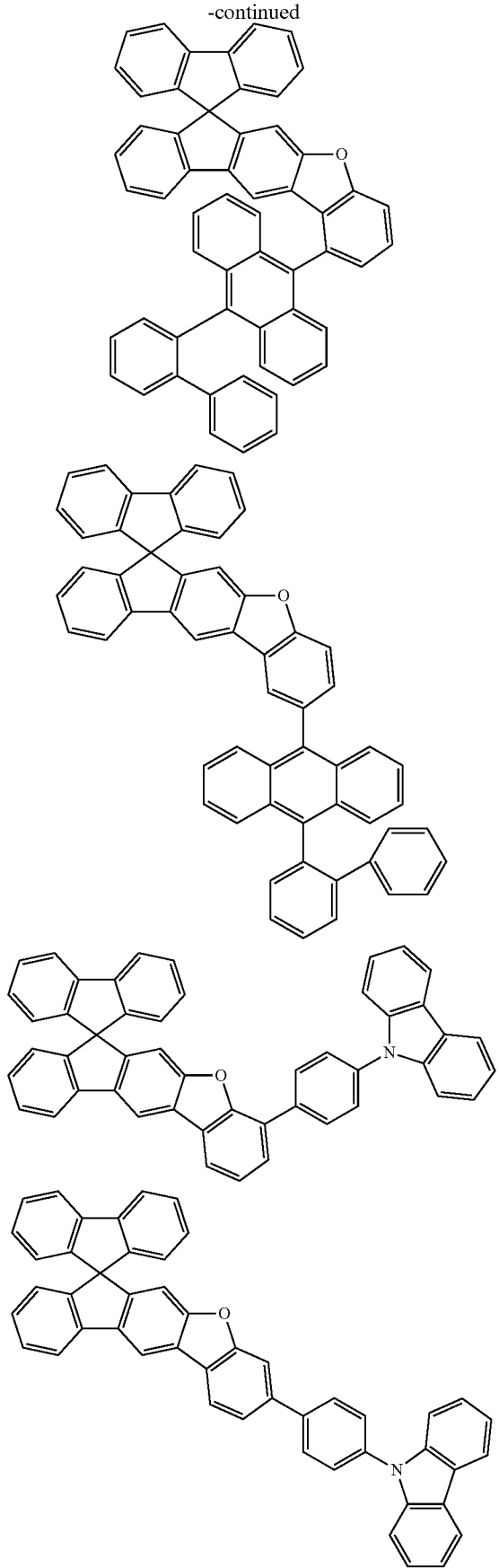
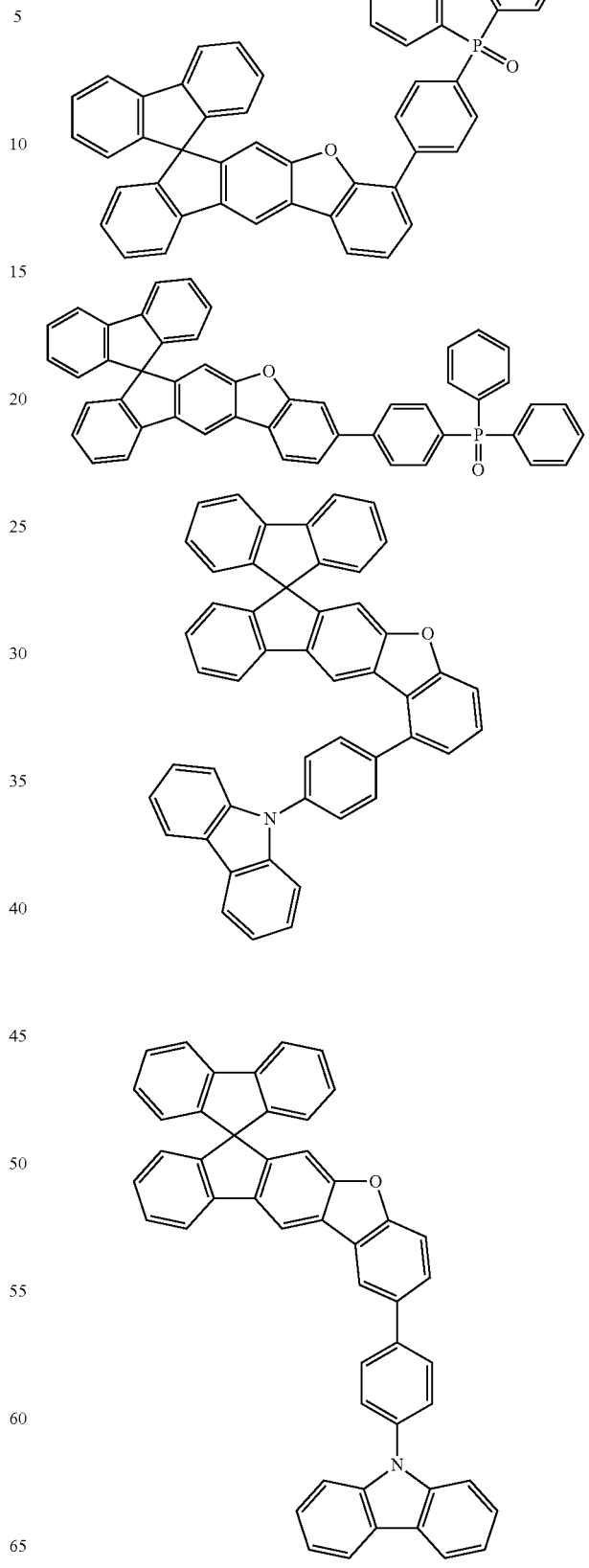

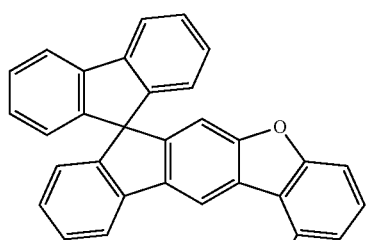
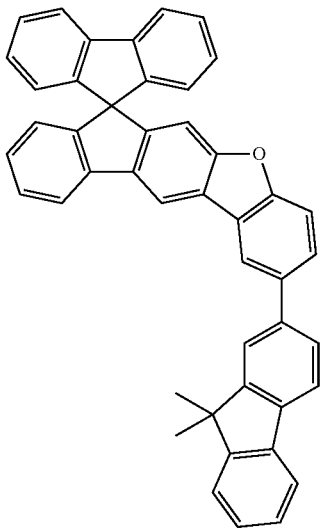
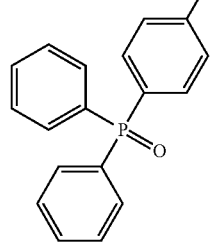
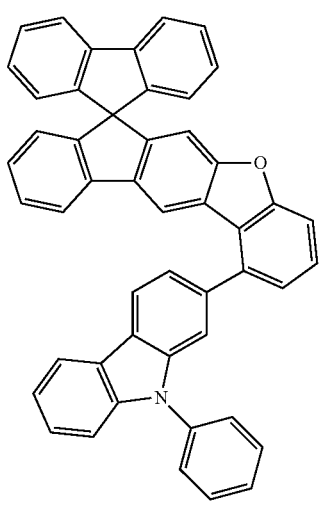
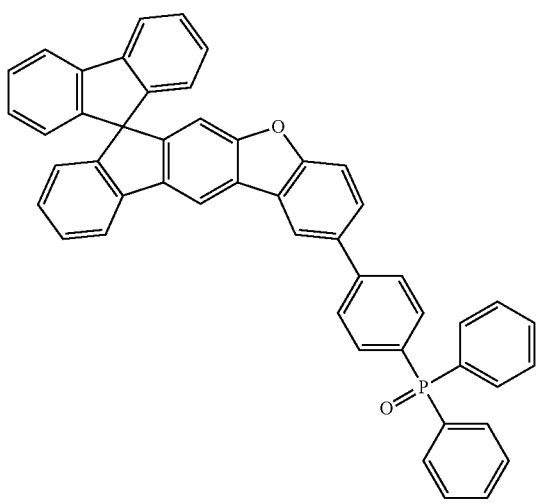
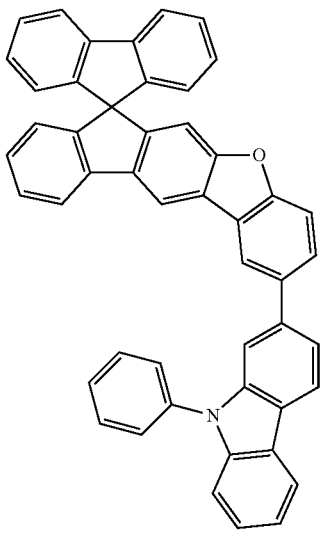

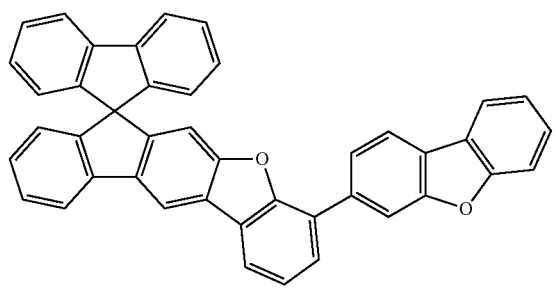
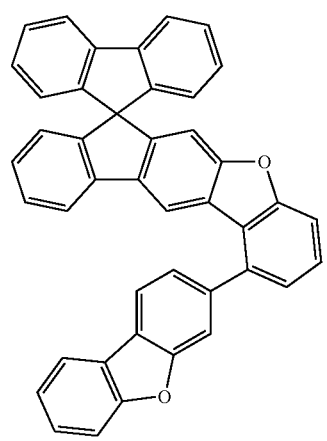
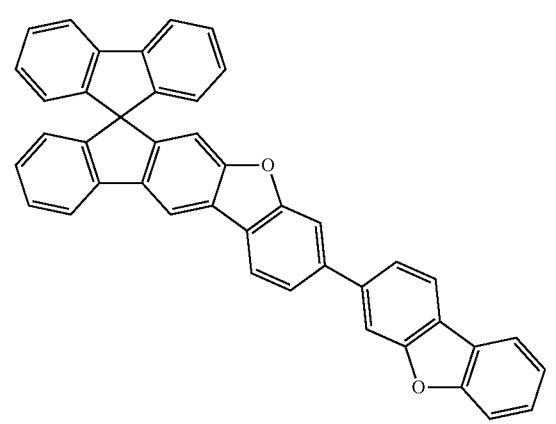
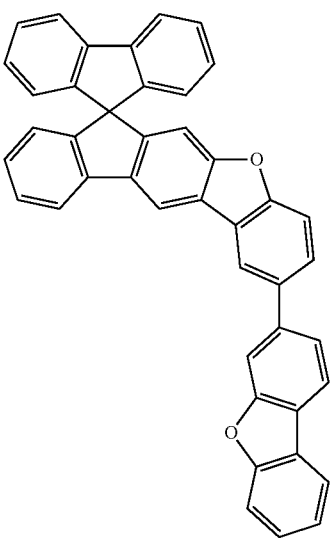
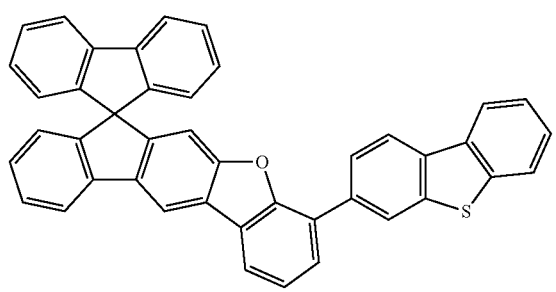
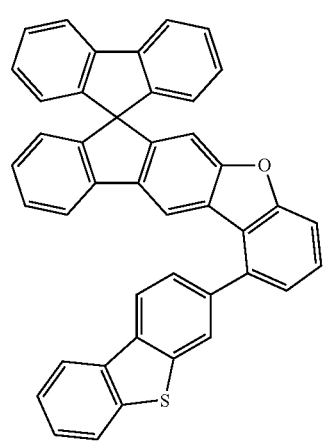

-continued
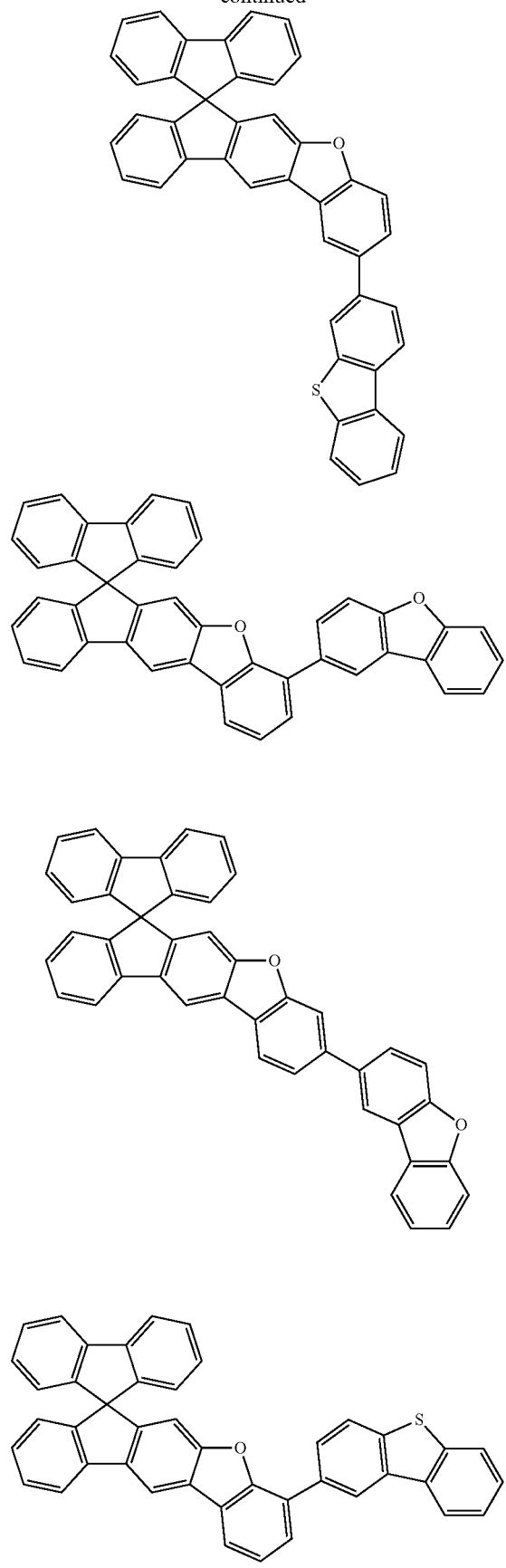
-continued
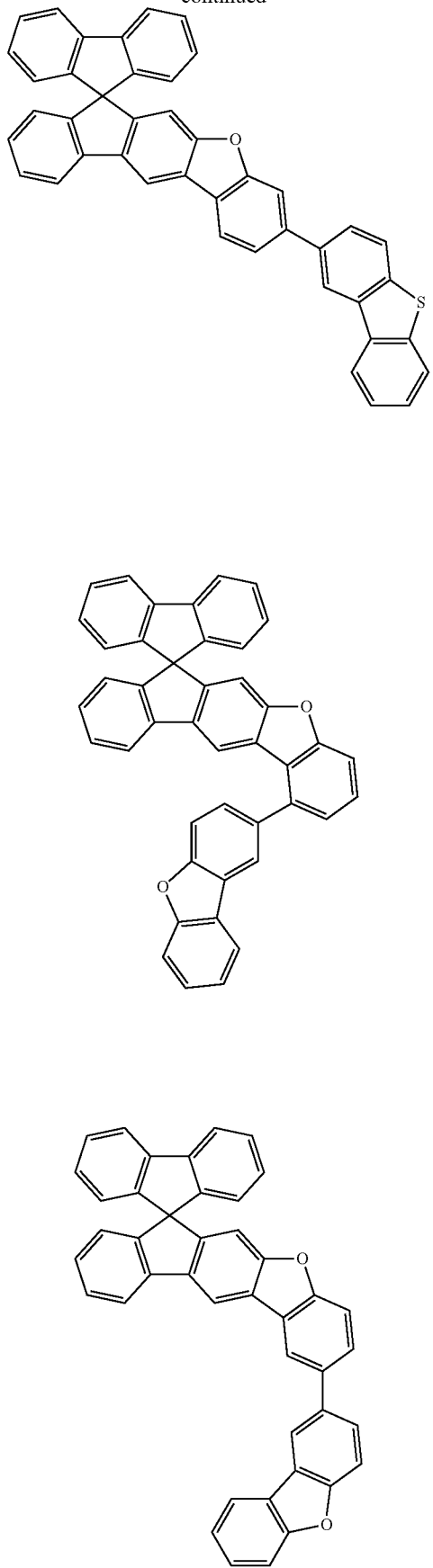

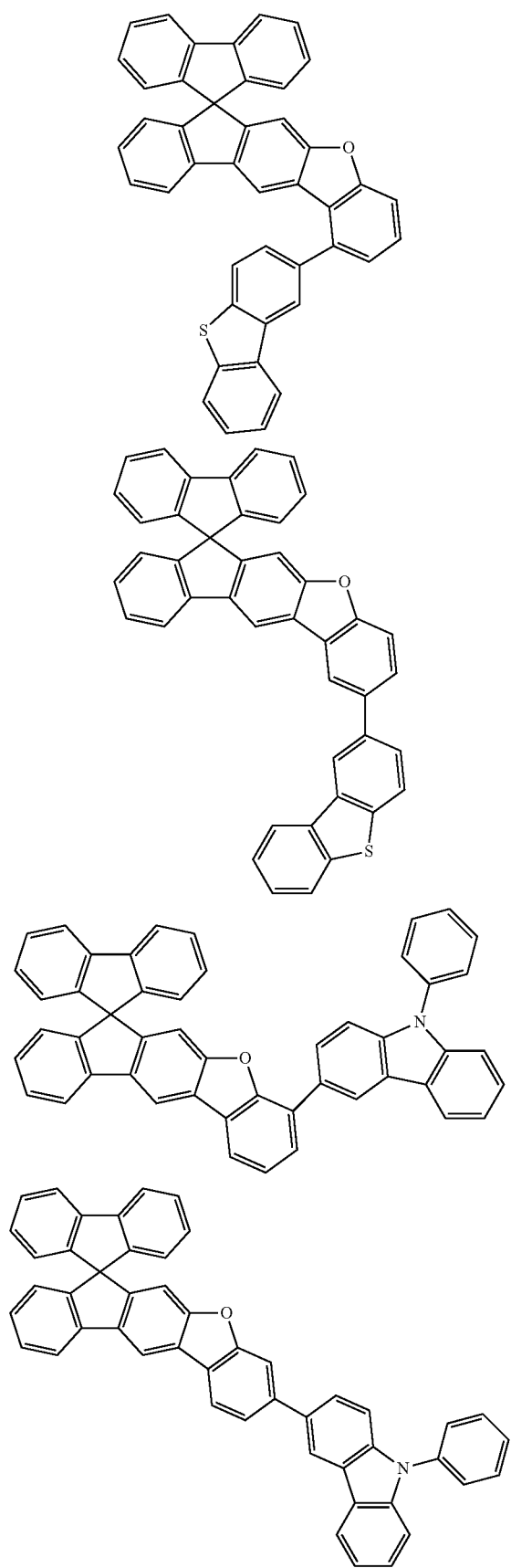
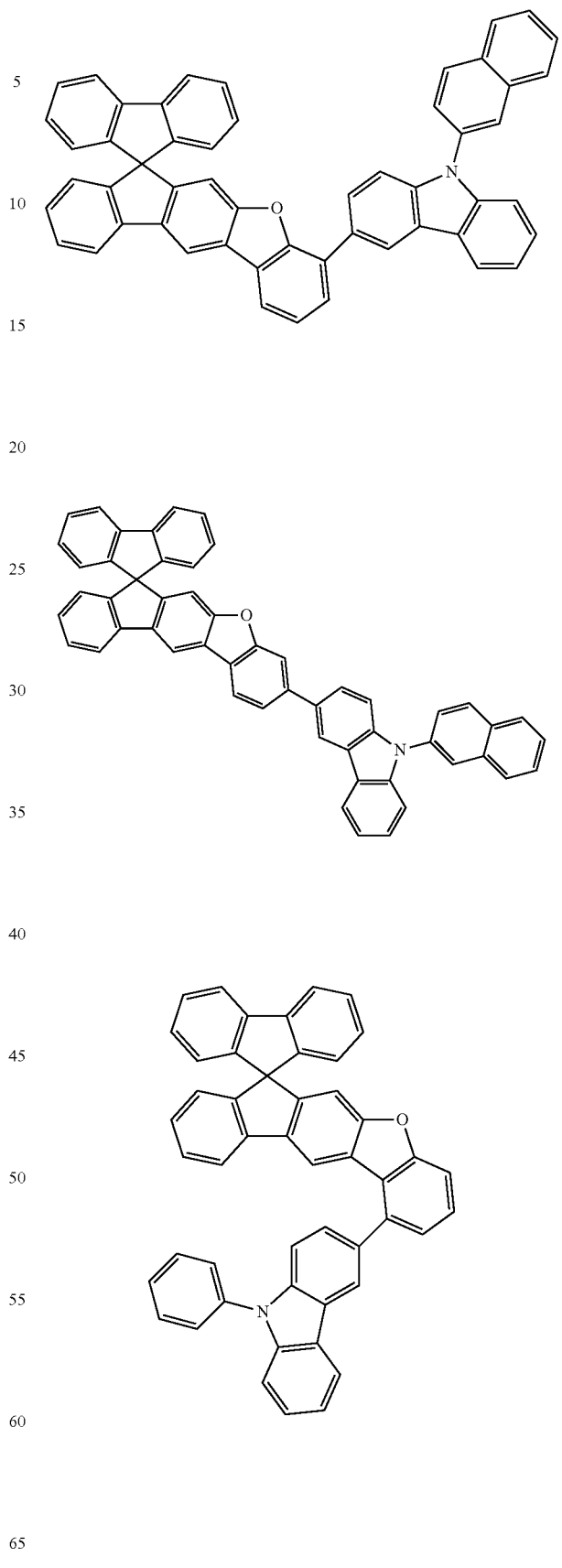

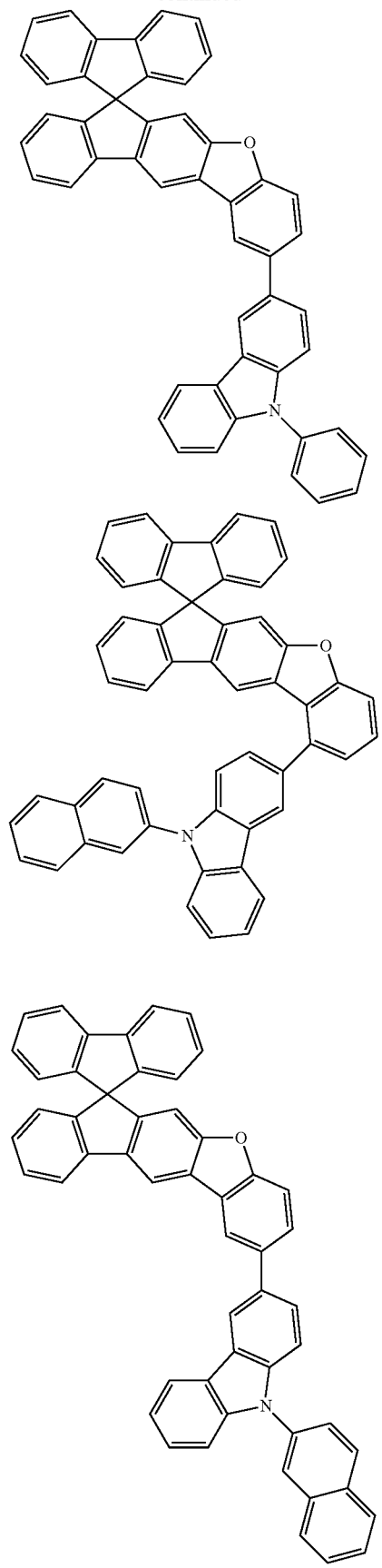 [SMILES: c1ccc(-n2c3ccccc3c3cc(-c4ccc5oc6cc7c(cc6c5c4)-c4ccccc4C74c5ccccc5-c5ccccc54)ccc32)cc1 ; c1ccc2c(c1)-c1ccccc1C21c2ccccc2-c2cc3c(cc21)oc1cccc(-c2ccc4c(c2)c2ccccc2n4-c2ccc4ccccc4c2)c13 ; c1ccc2c(c1)-c1ccccc1C21c2ccccc2-c2cc3c(cc21)oc1ccc(-c2ccc4c(c2)c2ccccc2n4-c2ccc4ccccc4c2)cc13]
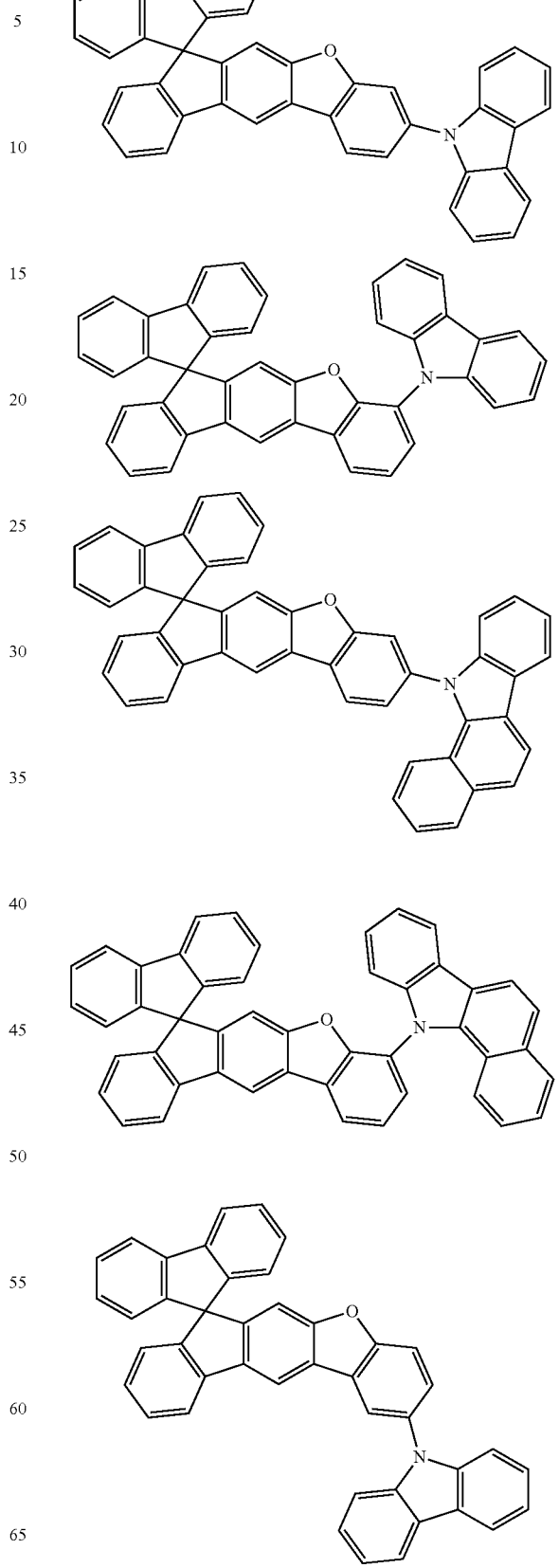

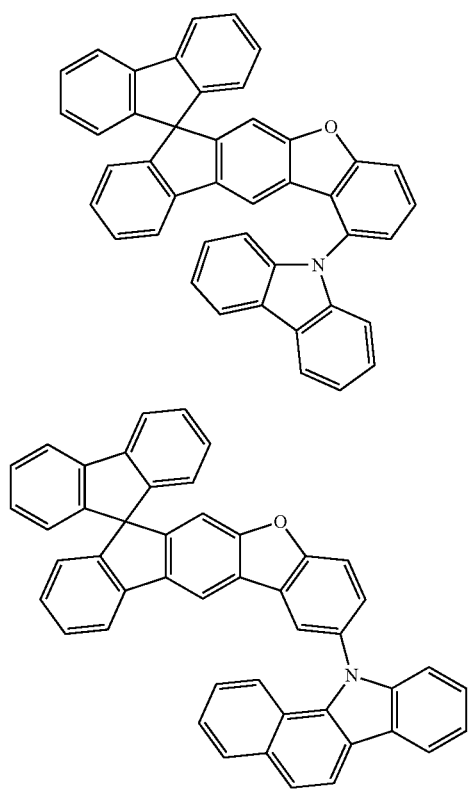
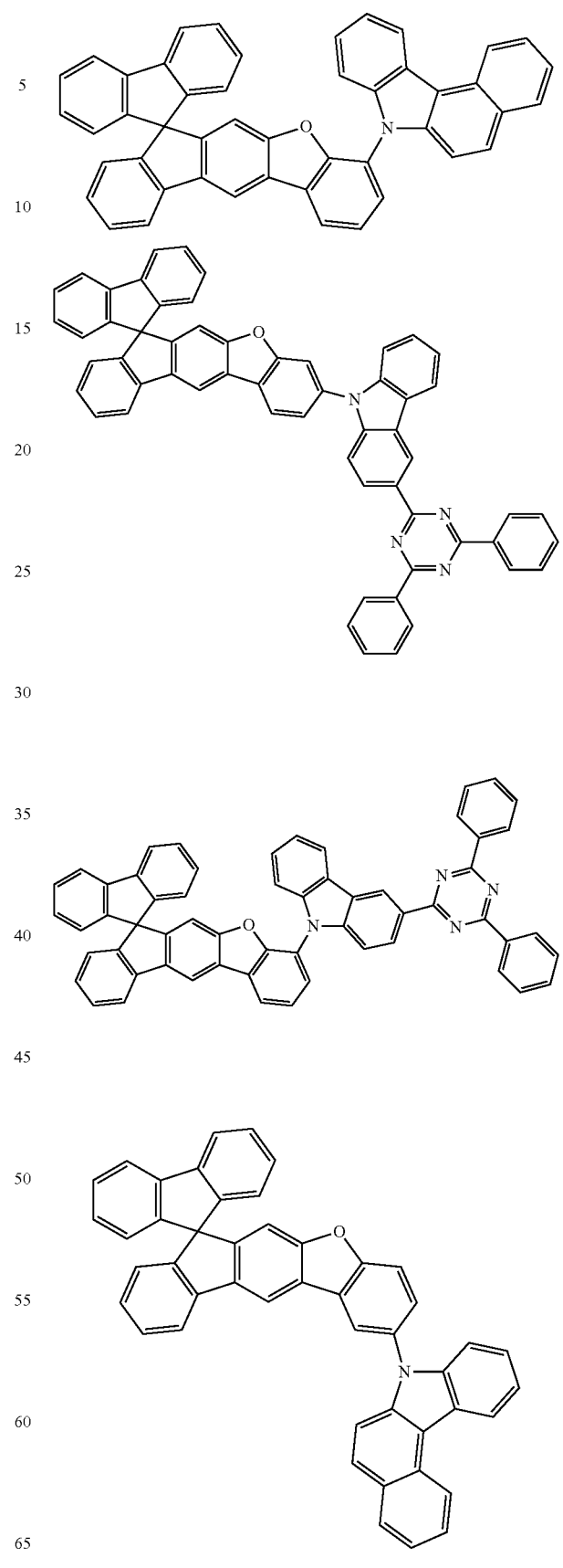

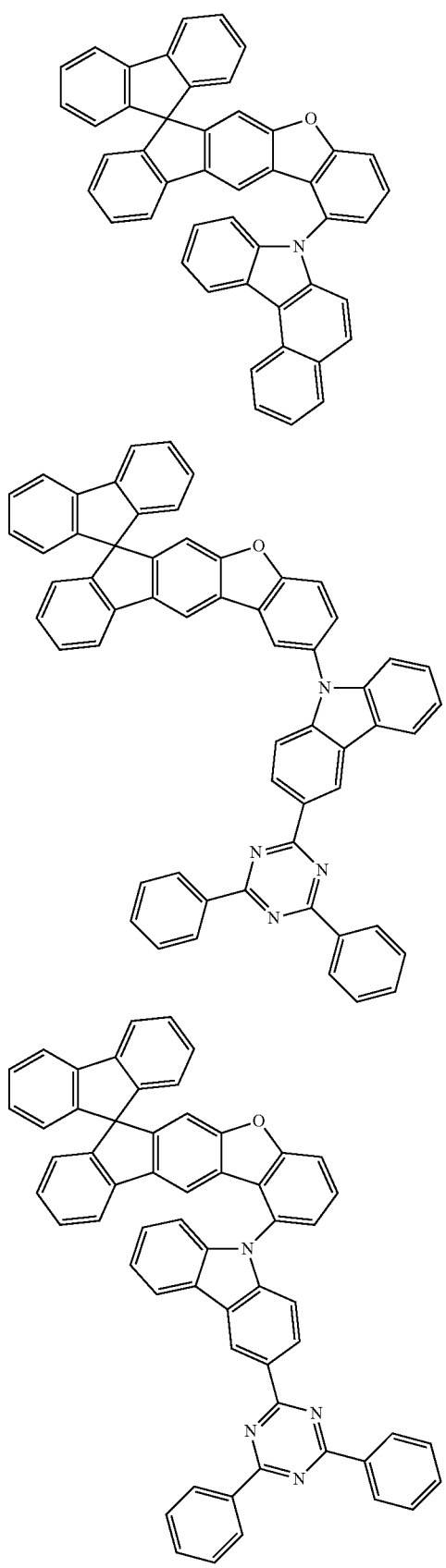 [SMILES: c1ccc2c(c1)-c1ccccc1C21c2ccccc2-c2cc3c(cc21)oc1cccc(-n2c4ccccc4c4c5ccccc5ccc42)c13 ; c1ccc(-c2nc(-c3ccccc3)nc(-c3ccc4c(c3)c3ccccc3n4-c3ccc4oc5cc6c(cc5c4c3)-c3ccccc3C63c4ccccc4-c4ccccc43)n2)cc1 ; c1ccc(-c2nc(-c3ccccc3)nc(-c3ccc4c(c3)c3ccccc3n4-c3cccc4oc5cc6c(cc5c34)-c3ccccc3C63c4ccccc4-c4ccccc43)n2)cc1]
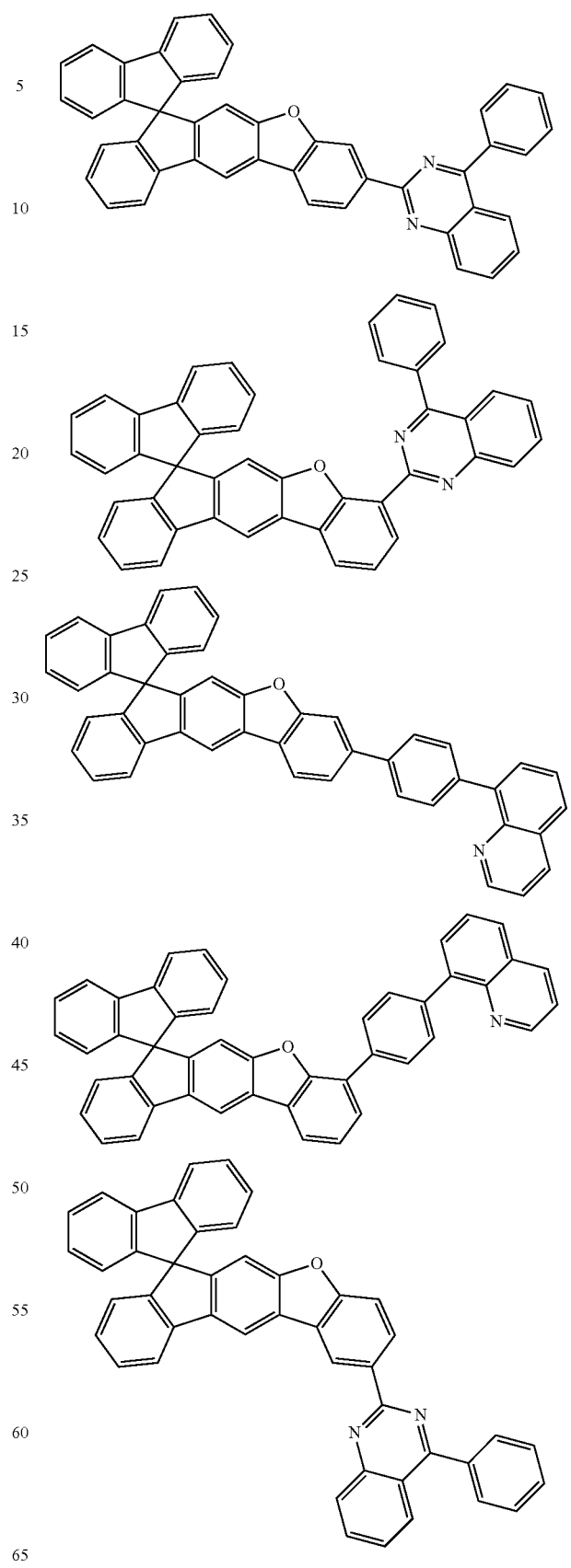

-continued
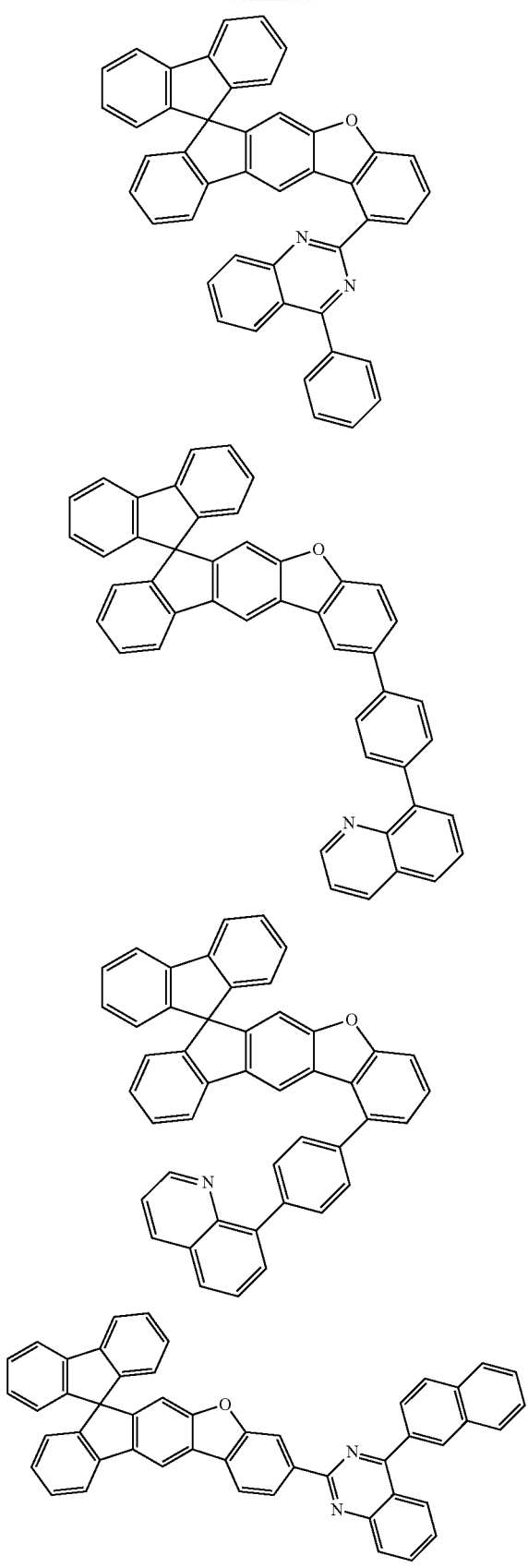
-continued
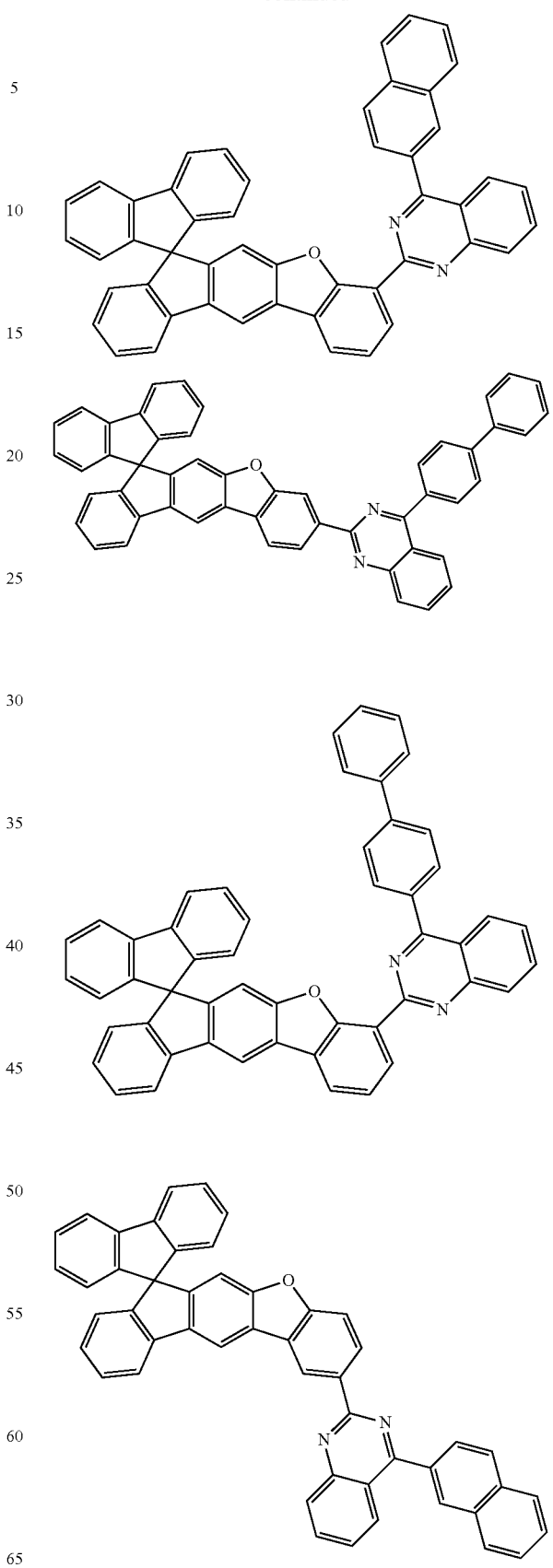

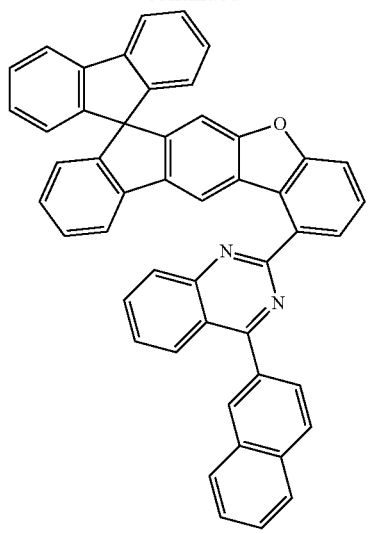
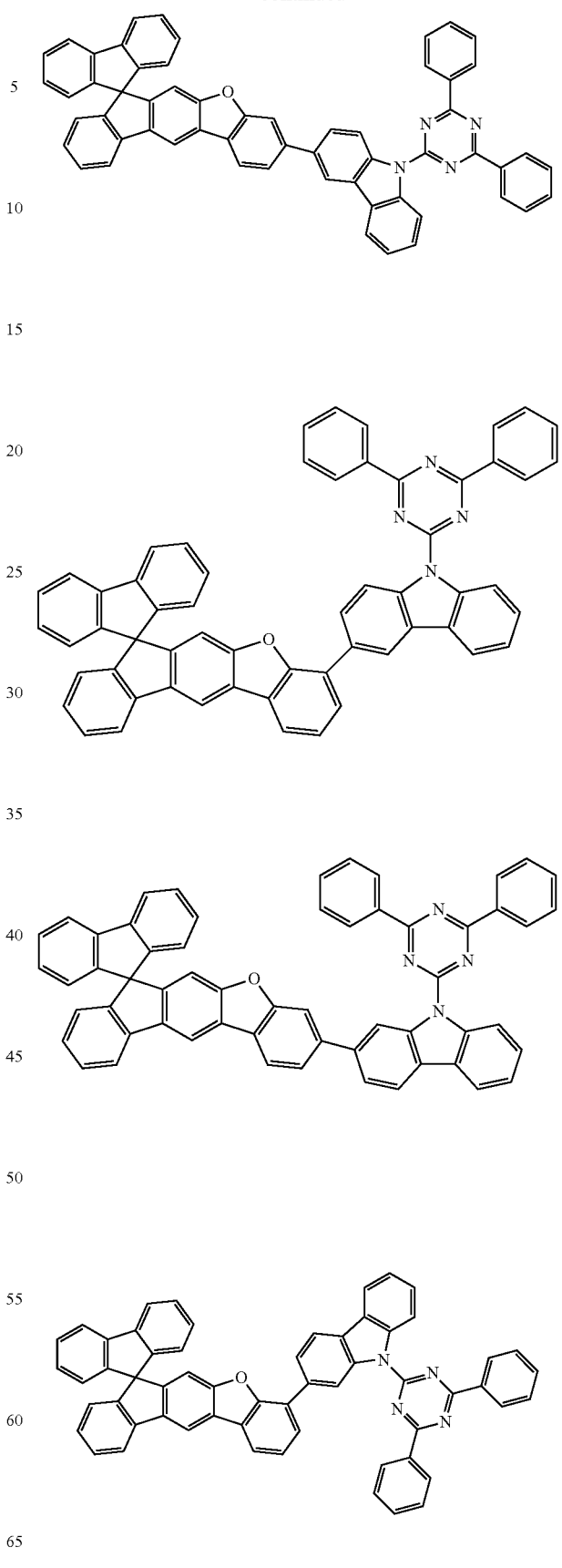

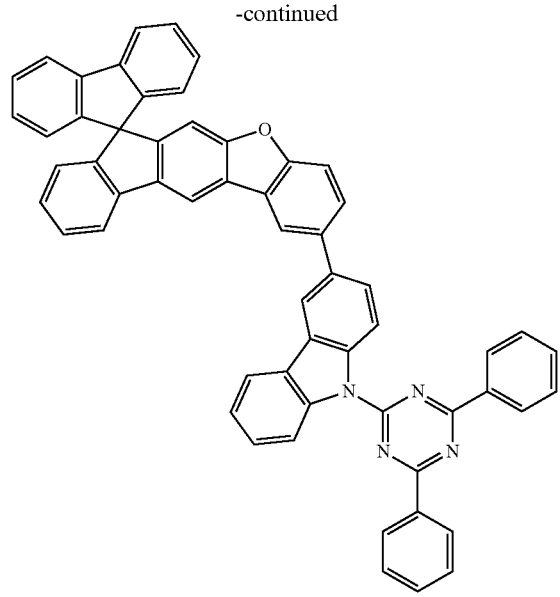
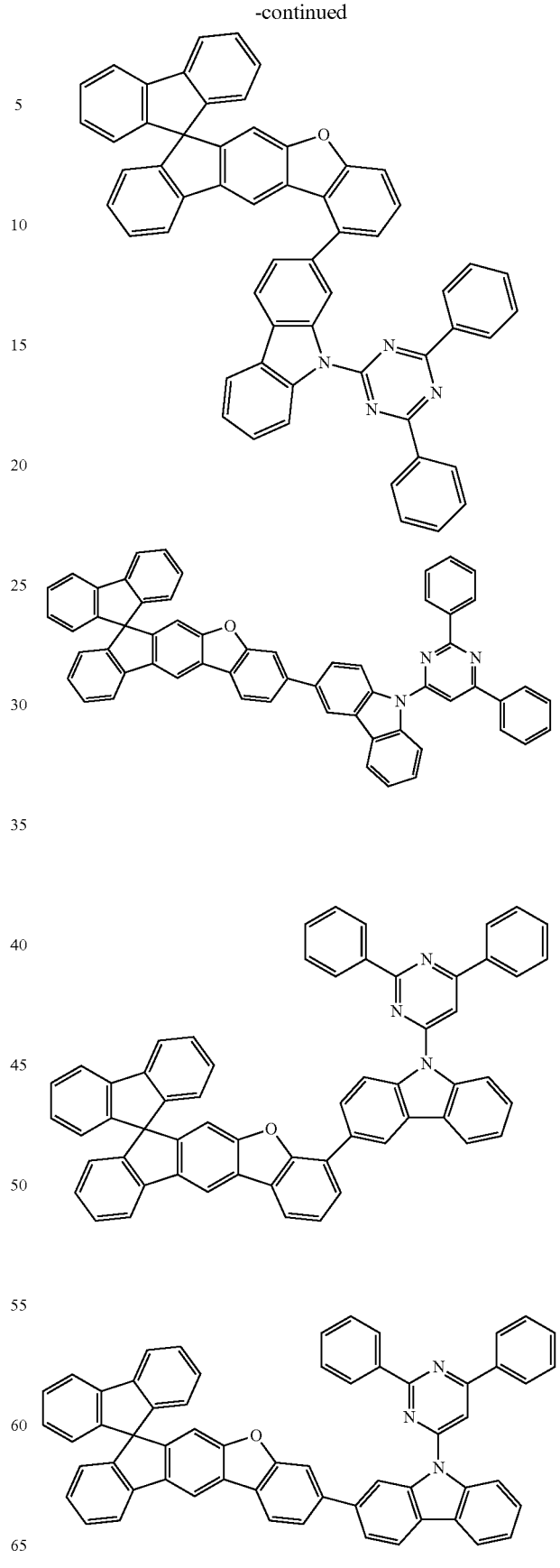

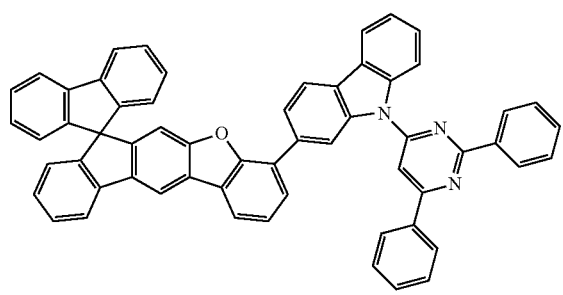
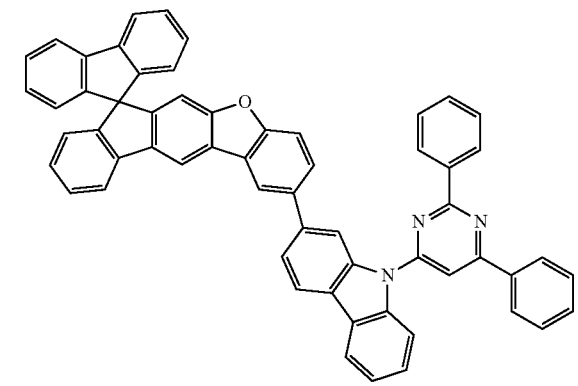
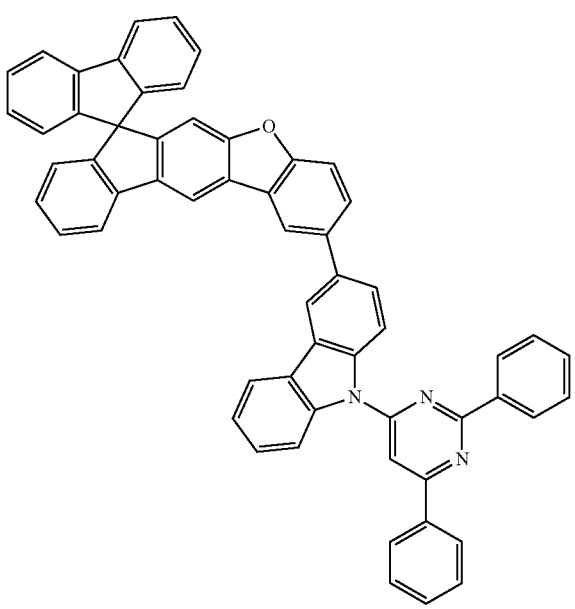
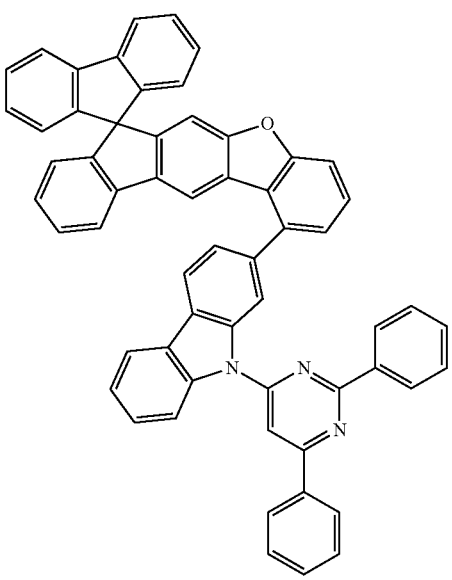
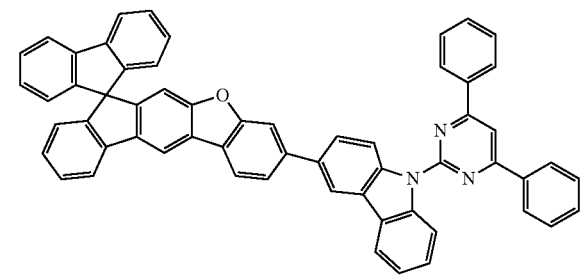
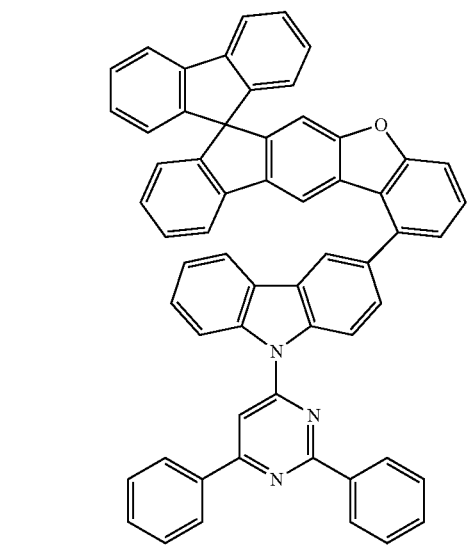
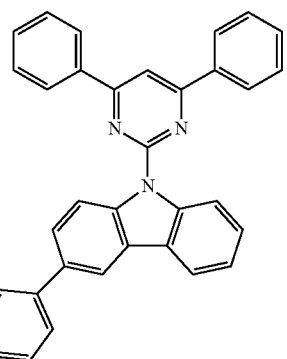

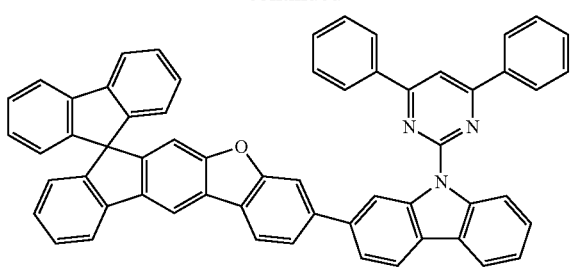
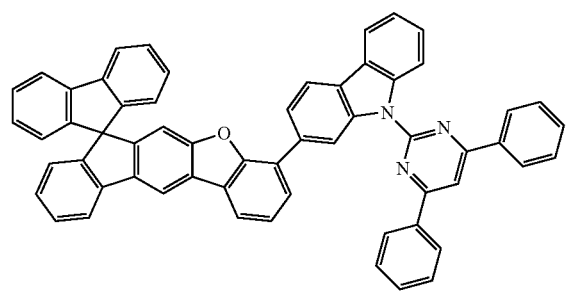
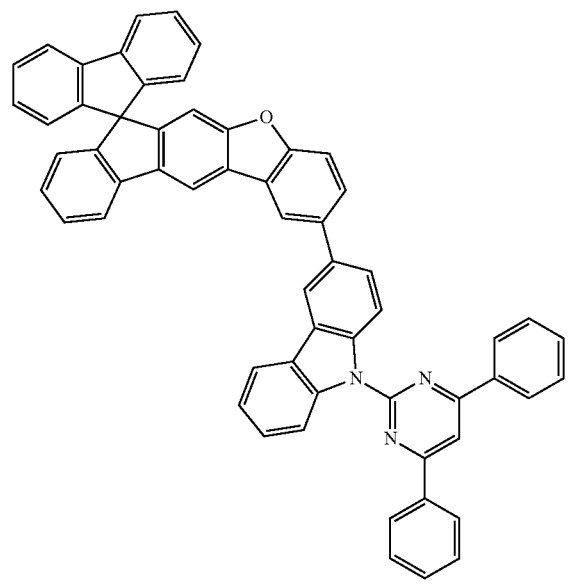
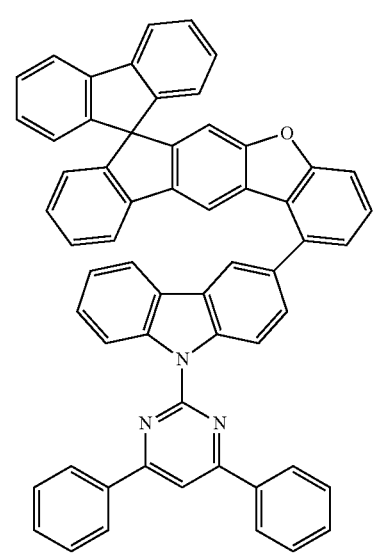
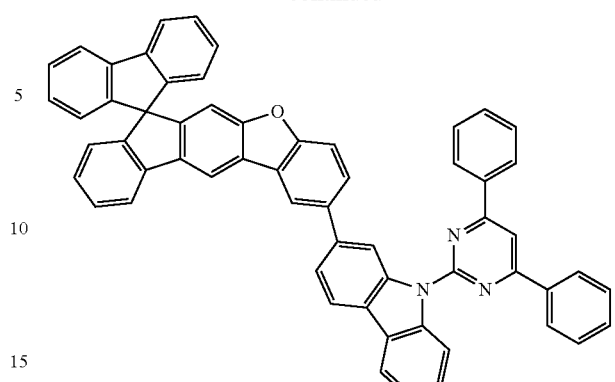
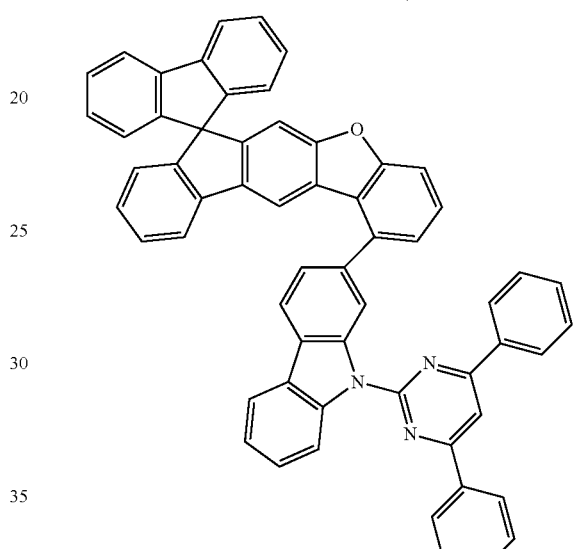
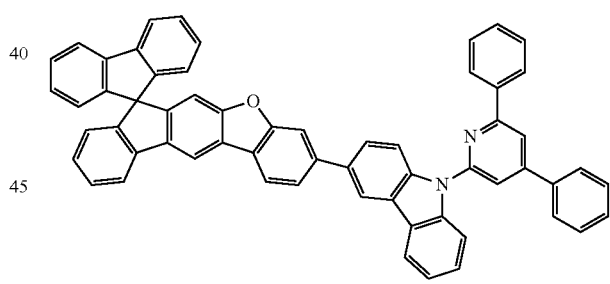
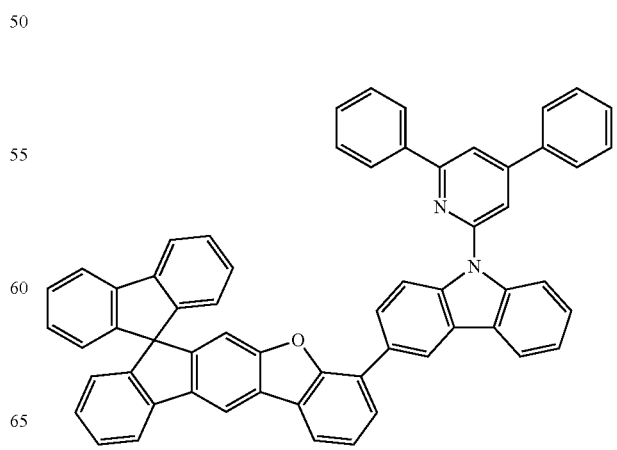

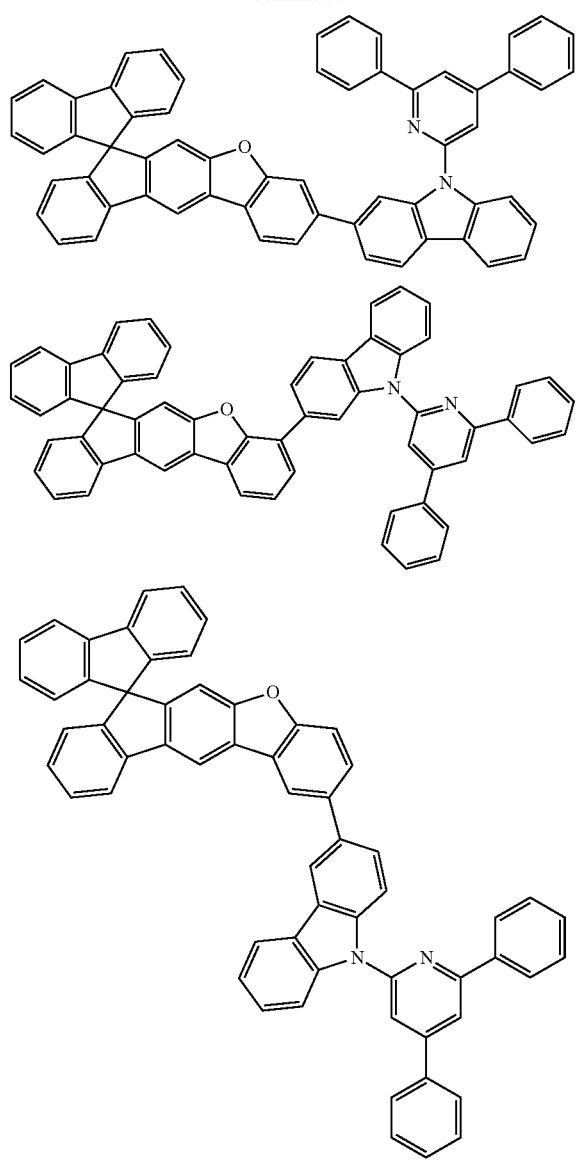
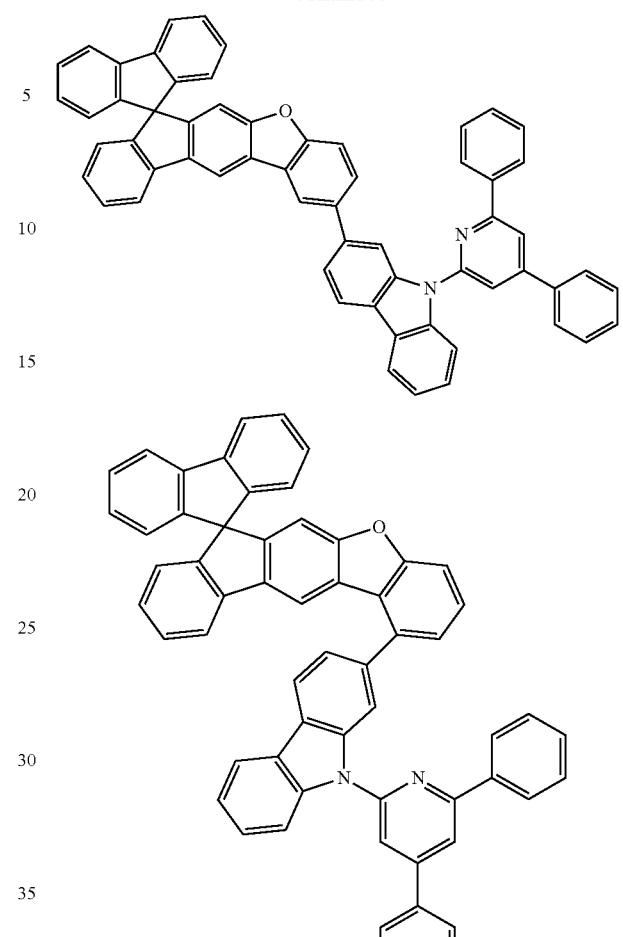
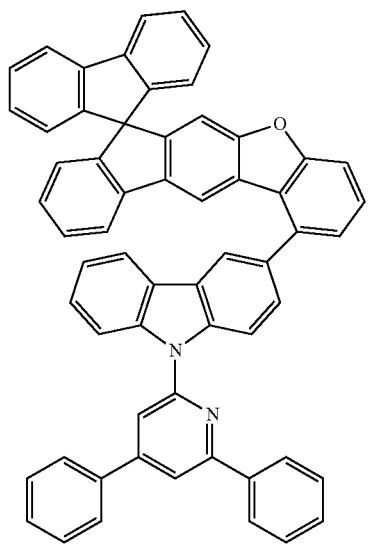
According to an exemplary embodiment of the present specification, a core structure of the hetero-cyclic compound represented by Chemical Formula 1 may be prepared by the following General Formula 1, but the preparation method thereof is not limited thereto.
[General Formula 1]
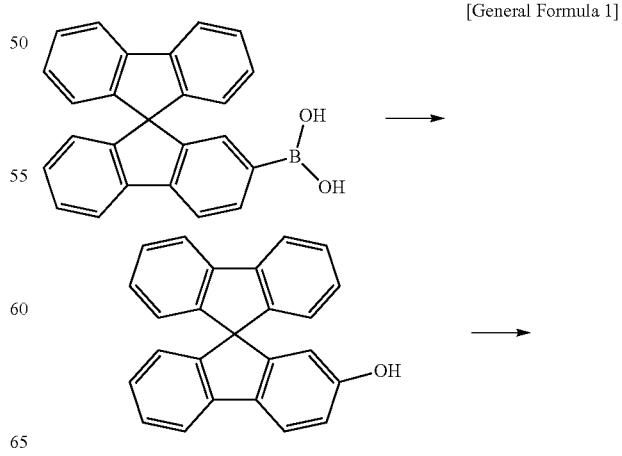

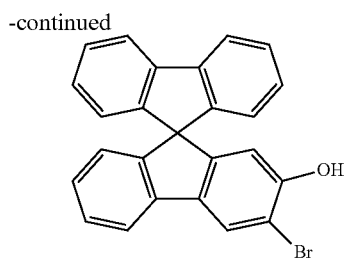

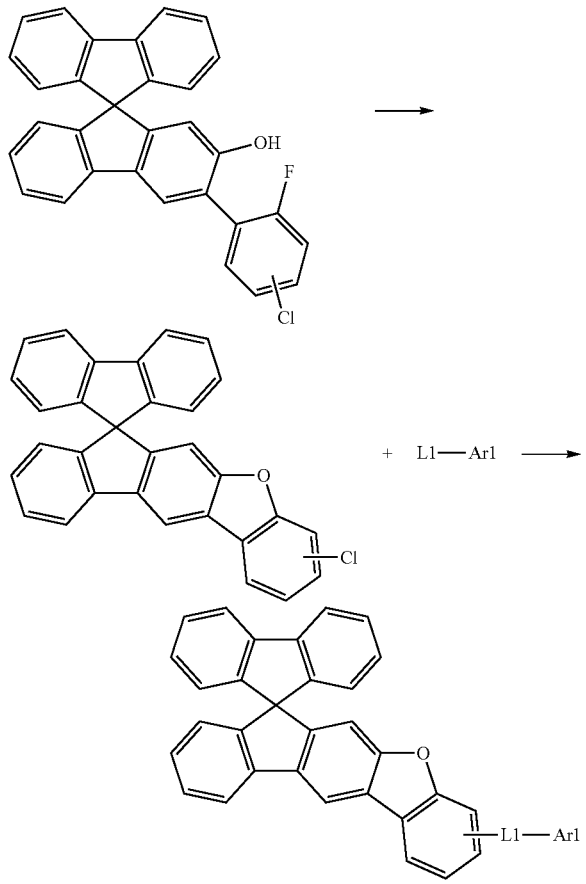

In General Formula 1, the definitions of L1 and Ar1 are the same as those in Chemical Formula 1.

An exemplary embodiment of the present specification provides an organic light emitting device including: a first electrode; a second electrode disposed to face the first electrode; and an organic material layer having one or more layers disposed between the first electrode and the second electrode, in which one or more layers of the organic material layer include the above-described hetero-cyclic compound.

According to an exemplary embodiment of the present specification, the organic material layer of the organic light emitting device of the present specification may be composed of a mono layer structure, but may be composed of a multi-layer structure in which two or more organic material layers are stacked. For example, the organic light emitting device of the present invention may have a structure including a hole injection layer, a hole transporting layer, an electron blocking layer, a light emitting layer, a hole blocking layer, an electron transporting layer, an electron injection layer, and the like as organic material layers. However, the structure of the organic light emitting device is not limited thereto, and may include fewer or more organic layers.

For example, the structure of the organic light emitting device of the present specification may have a structure as illustrated in FIGS. 1 and 2, but is not limited thereto.

FIG. 1 exemplifies the structure of an organic light emitting device 10 in which a first electrode 30, a light emitting layer 40, and a second electrode 50 are sequentially stacked on a substrate 20. FIG. 1 is an exemplified structure of the organic light emitting device according to an exemplary embodiment of the present specification, and may further include other organic material layers.

FIG. 2 exemplifies the structure of an organic light emitting device in which a first electrode 30, a hole injection layer 60, a hole transporting layer 70, a light emitting layer 40, an electron transporting layer 80, an electron injection layer 90, and a second electrode 50 are sequentially stacked on a substrate 20. FIG. 2 is an exemplified structure according to another exemplary embodiment of the present specification, and may further include other organic material layers.

According to an exemplary embodiment of the present specification, the organic material layer includes a hole transporting layer, and the hole transporting layer includes the hetero-cyclic compound represented by Chemical Formula 1.

According to an exemplary embodiment of the present specification, the organic material layer includes an electron blocking layer, and the electron blocking layer includes the hetero-cyclic compound represented by Chemical Formula 1.

According to an exemplary embodiment of the present specification, the organic material layer includes an electron injection layer, and the electron injection layer includes the hetero-cyclic compound represented by Chemical Formula 1.

According to an exemplary embodiment of the present specification, the organic material layer includes an electron transporting layer, and the electron transporting layer includes the hetero-cyclic compound represented by Chemical Formula 1.

According to an exemplary embodiment of the present specification, the organic material layer includes a light emitting layer, and the light emitting layer includes the hetero-cyclic compound represented by Chemical Formula 1.

According to an exemplary embodiment of the present specification, the organic material layer includes a light emitting layer, the light emitting layer is a green light emitting layer, and the green light emitting layer includes the hetero-cyclic compound represented by Chemical Formula 1.

According to an exemplary embodiment of the present specification, the organic material layer includes a light emitting layer, the light emitting layer is a red light emitting layer, and the red light emitting layer includes the hetero-cyclic compound represented by Chemical Formula 1.

According to an exemplary embodiment of the present specification, the organic material layer includes a light emitting layer, the light emitting layer is a blue light emitting layer, and the blue light emitting layer includes the hetero-cyclic compound represented by Chemical Formula 1.

According to an exemplary embodiment of the present specification, the organic material layer includes a light emitting layer, and the light emitting layer includes the hetero-cyclic compound represented by Chemical Formula 1 as a host of the light emitting layer.

In an exemplary embodiment of the present specification, the organic material layer may include the hetero-cyclic compound represented by Chemical Formula 1 as a host, and may include another organic compound, a metal or a metal compound as a dopant.
The dopant may be one or more selected from the following exemplified compounds, but is not limited thereto.
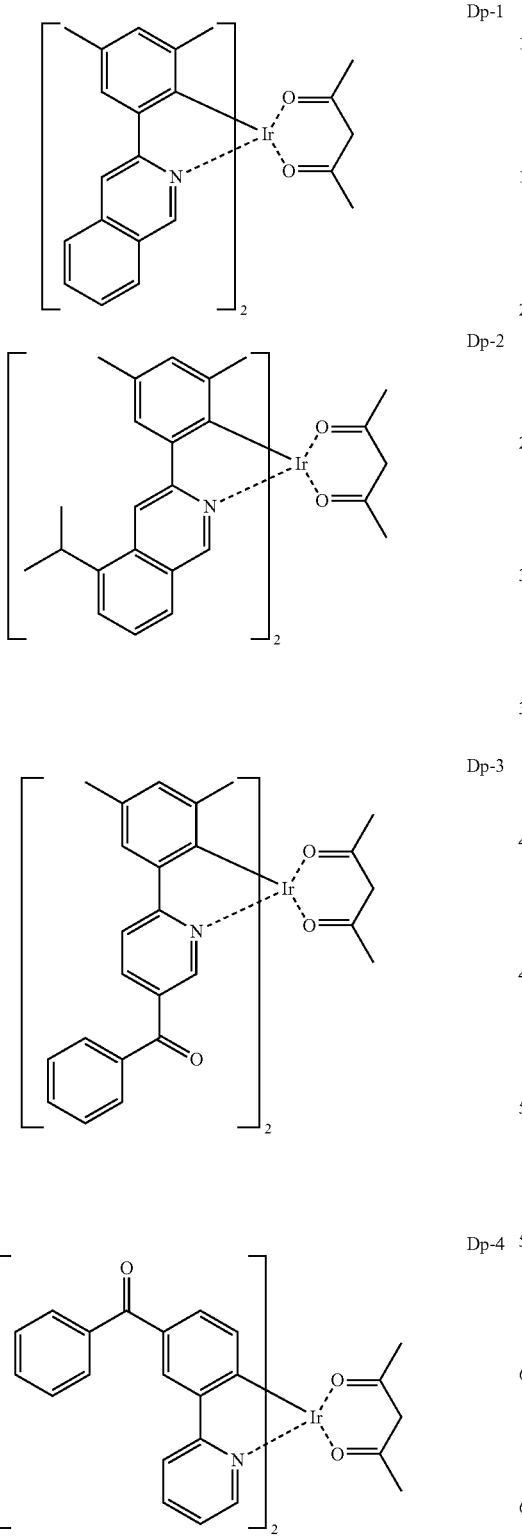
Dp-1
Dp-2
Dp-3
Dp-4
-continued
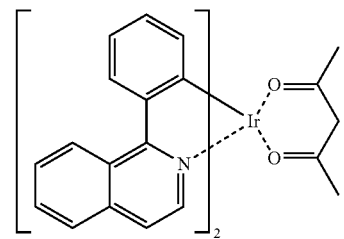
Dp-5
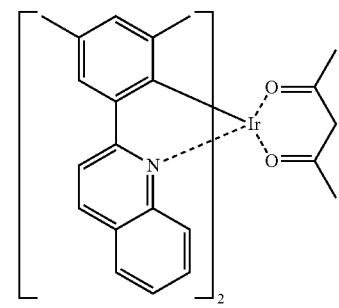
Dp-6
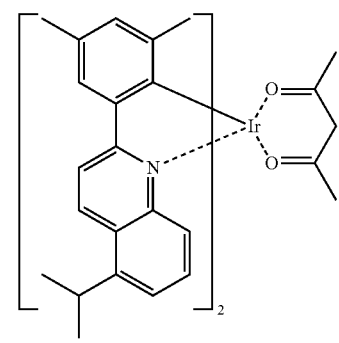
Dp-7
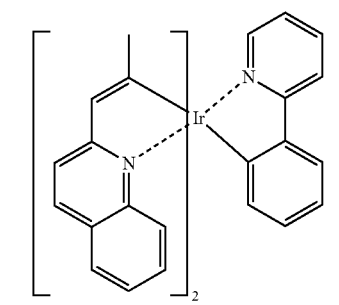
Dp-8
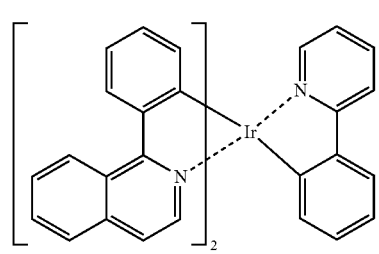
Dp-9

Dp-10
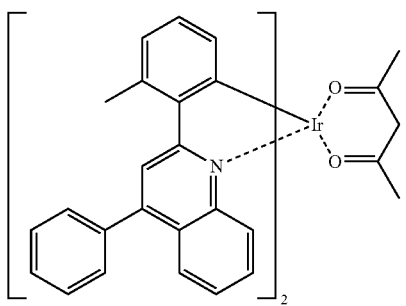
Dp-11
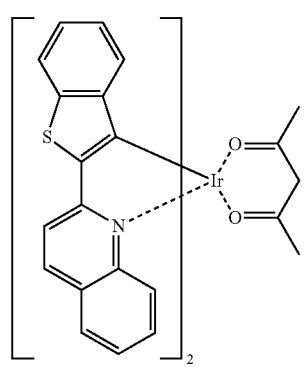
Dp-12
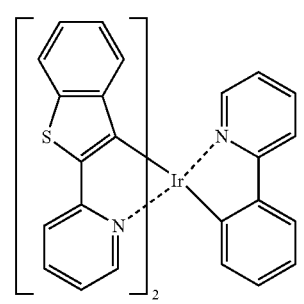
Dp-13
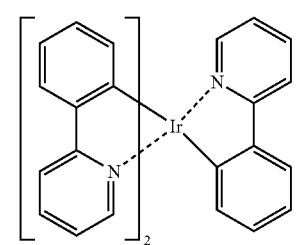
Dp-14
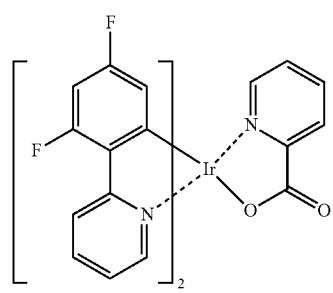
Dp-15
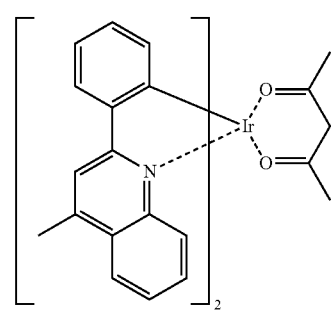
Dp-16
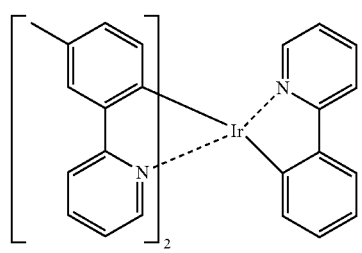
Dp-17
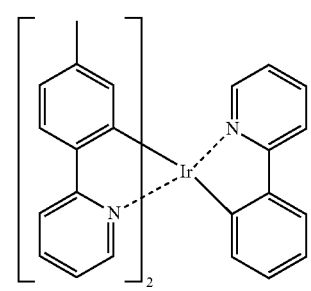
Dp-18
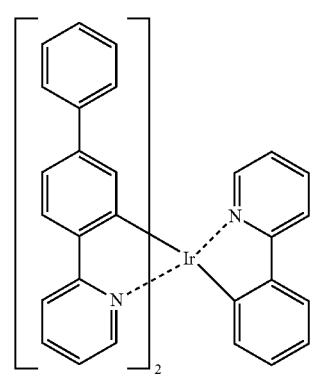
Dp-19
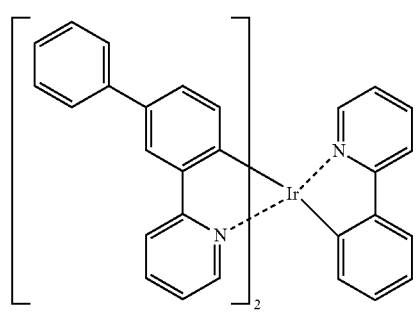

Dp-20 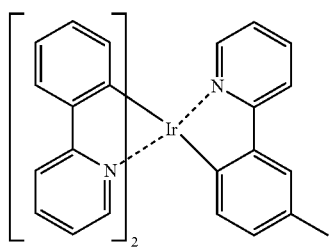

Dp-21 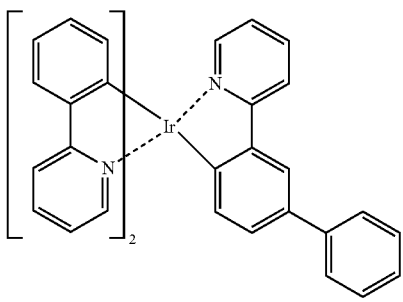

Dp-22 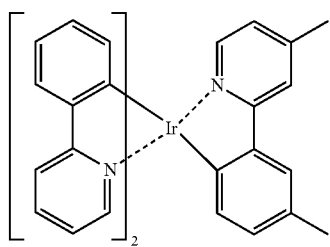

Dp-23 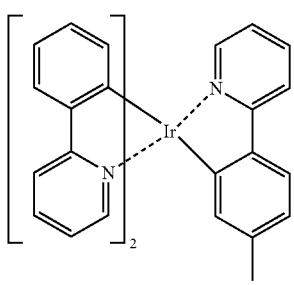

Dp-24 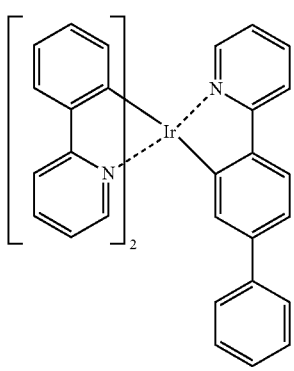

Dp-25 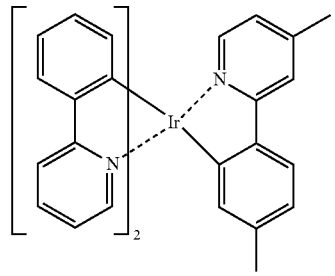

Dp-26 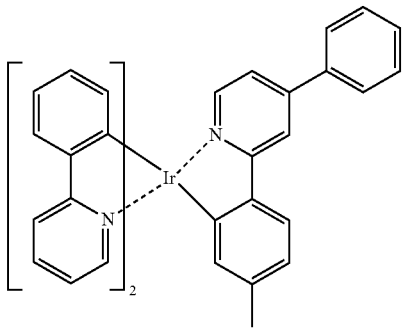

Dp-27 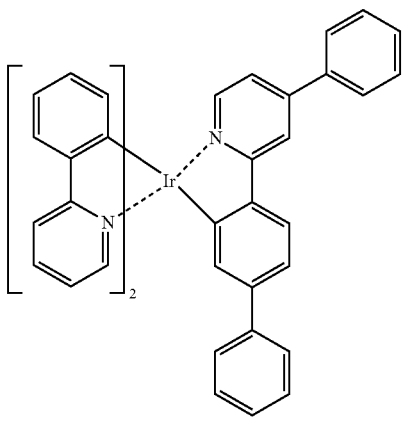

According to an exemplary embodiment of the present specification, the organic material layer may further include one or more layers selected from the group consisting of a hole injection layer, a hole transporting layer, a light emitting layer, an electron transporting layer, and an electron injection layer.

The organic light emitting device of the present specification may be manufactured by the materials and methods known in the art, except that one or more layers of the organic material layer include the hetero-cyclic compound of the present specification, that is, the hetero-cyclic compound represented by Chemical Formula 1.

When the organic light emitting device includes a plurality of organic material layers, the organic material layers may be formed of the same material or different materials.

For example, the organic light emitting device of the present specification may be manufactured by sequentially stacking a first electrode, an organic material layer, and a second electrode on a substrate. In this case, the organic light emitting device may be manufactured by depositing a metal or a metal oxide having conductivity, or an alloy thereof on a substrate to form a first electrode, forming an organic material layer including a hole injection layer, a hole transporting layer, a light emitting layer, and an electron transporting layer thereon, and then depositing a material, which may be used as a second electrode, thereon, by using a physical vapor deposition (PVD) method such as sputtering or e-beam evaporation. In addition to the method described above, an organic light emitting device may be made by sequentially depositing a second electrode material, an organic material layer, and a first electrode material on a substrate. Further, the hetero-cyclic compound represented by Chemical Formula 1 may be formed as an organic material layer by not only a vacuum deposition method, but also a solution application method when an organic light emitting device is manufactured. Here, the solution application method means spin coating, dip coating, doctor blading, inkjet printing, screen printing, a spray method, roll coating, and the like, but is not limited thereto.

According to an exemplary embodiment of the present specification, the first electrode is a positive electrode, and the second electrode is a negative electrode.

According to another exemplary embodiment of the present specification, the first electrode is a negative electrode, and the second electrode is a positive electrode. As the positive electrode material, materials having a high work function are usually preferred so as to facilitate the injection of holes into an organic material layer.

Specific examples of the positive electrode material which may be used in the present invention include: a metal such as vanadium, chromium, copper, zinc, and gold, or an alloy thereof; a metal oxide such as zinc oxide, indium oxide, indium tin oxide (ITO), and indium zinc oxide (IZO); a combination of a metal and an oxide, such as ZnO:Al or $SnO_2$:Sb; a conductive polymer such as poly(3-methylthiophene), poly[3,4-(ethylene-1,2-dioxy)thiophene] (PEDOT), polypyrrole, and polyaniline; and the like, but are not limited thereto.

As the negative electrode material, materials having a low work function are usually preferred so as to facilitate the injection of electrons into an organic material layer. Specific examples of the negative electrode material include: a metal such as magnesium, calcium, sodium, potassium, titanium, indium, yttrium, lithium, gadolinium, aluminum, silver, tin, and lead, or an alloy thereof; a multi-layer structured material, such as LiF/Al or $LiO_2$/Al and Mg/Ag, and the like, but are not limited thereto.

The hole injection layer is a layer which injects holes from an electrode, and a hole injection material is preferably a compound which has a capability of transporting holes and thus has an effect of injecting holes at a positive electrode and an excellent effect of injecting holes for a light emitting layer or a light emitting material, prevents excitons produced from the light emitting layer from moving to an electron injection layer or an electron injection material, and is also excellent in the ability to form a thin film. The highest occupied molecular orbital (HOMO) of the hole injection material is preferably a value between the work function of the positive electrode material and the HOMO of the neighboring organic material layer. Specific examples of the hole injection material include metal porphyrin, oligothiophene, arylamine-based organic materials, hexanitrile hexaazatriphenylene-based organic materials, quinacridone-based organic materials, perylene-based organic materials, anthraquinone, polyaniline-based and polythiophene-based conductive polymers, and the like, but are not limited thereto.

The hole transporting layer is a layer which accepts holes from a hole injection layer and transports the holes to a light emitting layer, and a hole transporting material is suitably a material having high hole mobility which may accept holes from a positive electrode or a hole injection layer and transfer the holes to a light emitting layer. Specific examples thereof include arylamine-based organic materials, conductive polymers, block copolymers having both conjugated portions and non-conjugated portions, and the like, but are not limited thereto.

A light emitting material for the light emitting layer is a material which may emit light in a visible light region by accepting and combining holes and electrons from a hole transporting layer and an electron transporting layer, respectively, and is preferably a material having high quantum efficiency for fluorescence or phosphorescence. Specific examples thereof include: an 8-hydroxy-quinoline aluminum complex ($Alq_3$); carbazole-based compounds; dimerized styryl compounds; BAlq; 10-hydroxybenzoquinoline-metal compounds; benzoxazole-based, benzothiazole-based and benzimidazole-based compounds; poly(p-phenylenevinylene) (PPV)-based polymers; spiro compounds; polyfluorene, lubrene, and the like, but are not limited thereto.

The light emitting layer may include a host material and a dopant material. Examples of the host material include a fused aromatic ring derivative, or a hetero ring-containing compound, and the like. Specifically, examples of the fused aromatic ring derivative include an anthracene derivative, a pyrene derivative, a naphthalene derivative, a pentacene derivative, a phenanthrene compound, a fluoranthene compound, and the like, and examples of the hetero ring-containing compound include a carbazole derivative, a dibenzofuran derivative, a ladder-type furan compound, a pyrimidine derivative, and the like, but the examples thereof are not limited thereto.

Examples of the dopant material include an aromatic amine derivative, a styrylamine compound, a boron complex, a fluoranthene compound, a metal complex, and the like. Specifically, the aromatic amine derivative is a fused aromatic ring derivative having a substituted or unsubstituted arylamino group, and examples thereof include a pyrene, an anthracene, a chrysene, a periflanthene, and the like, which have an arylamino group, and the styrylamine compound is a compound in which a substituted or unsubstituted arylamine is substituted with at least one arylvinyl group, and one or two or more substituents selected from the group consisting of an aryl group, a silyl group, an alkyl group, a cycloalkyl group, and an arylamino group is or are substituted or unsubstituted. Specific examples thereof include styrylamine, styryldiamine, styryltriamine, styryltetramine, and the like, but are not limited thereto. Further, examples of the metal complex include an iridium complex, a platinum complex, and the like, but are not limited thereto.

The electron transporting layer is a layer which accepts electrons from an electron injection layer and transports the electrons to a light emitting layer, and an electron transporting material is suitably a material having high electron mobility which may proficiently accept electrons from a negative electrode and transfer the electrons to a light emitting layer. Specific examples thereof include: Al complexes of 8-hydroxyquinoline; complexes including $Alq_3$; organic radical compounds; hydroxyflavone-metal complexes, and the like, but are not limited thereto. The electron transporting layer may be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and an electron injection material is preferably a compound which has a capability of transporting electrons, has an effect of injecting electrons from a negative electrode and an excellent effect of injecting electrons into a light emitting layer or a light emitting material, prevents excitons produced from the light emitting layer from moving to a hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris(2-methyl-8-hydroxyquinolinato) aluminum, tris(8-hydroxyquinolinato) gallium, bis(10-hydroxybenzo[h]quinolinato) beryllium, bis(10-hydroxybenzo[h]quinolinato) zinc, bis(2-methyl-8-quinolinato) chlorogallium, bis(2-methyl-8-quinolinato)(o-cresolato) gallium, bis(2-methyl-8-quinolinato) (1-naphtholato) aluminum, bis(2-methyl-8-quinolinato)(2-naphtholato) gallium, and the like, but are not limited thereto.

The organic light emitting device according to the present specification may be a top emission type, a bottom emission type, or a dual emission type according to the materials to be used.

According to an exemplary embodiment of the present specification, the hetero-cyclic compound represented by Chemical Formula 1 may be included in an organic solar cell or an organic transistor in addition to the organic light emitting device.

Hereinafter, the present specification will be described in detail with reference to Examples for specifically describing the present specification. However, the Examples according to the present specification may be modified in various forms, and it is not interpreted that the scope of the present specification is limited to the Examples described below in detail. The Examples of the present specification are provided to more completely explain the present specification to a person with ordinary skill in the art.

By the following Reaction Formula 1, Compounds A to H were prepared.

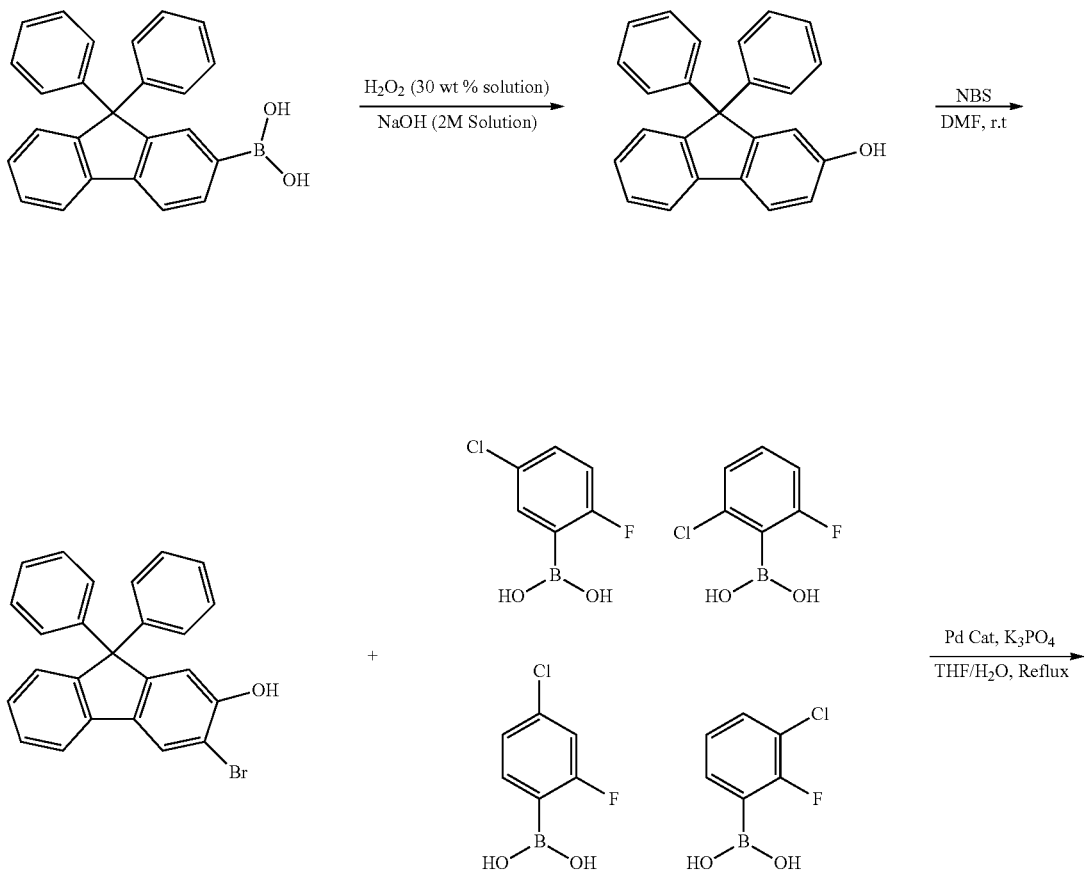

[Reaction Formula 1]

-continued
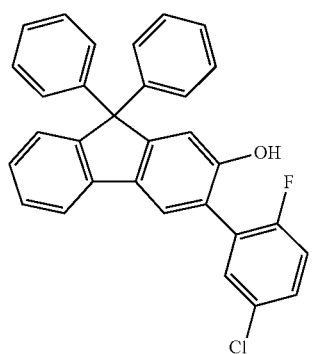
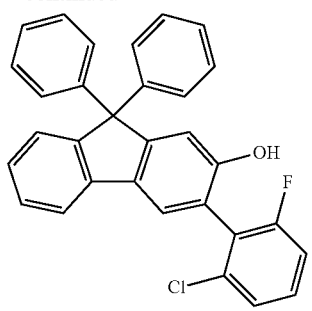
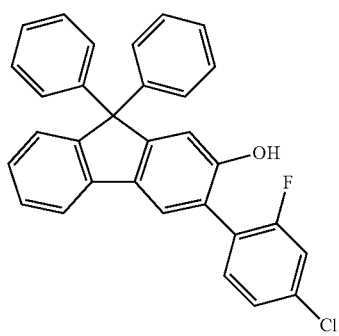
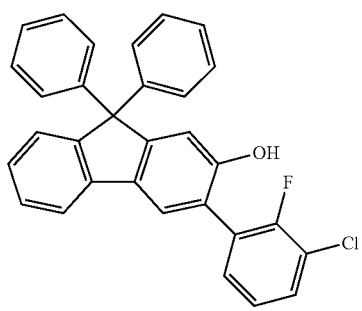
$\xrightarrow{\text{K}_2\text{CO}_3}{\text{NMP, 120° C.}}$
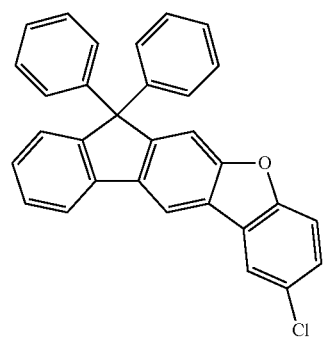
A
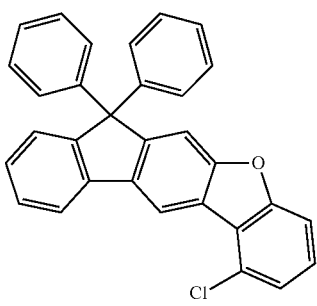
B
+
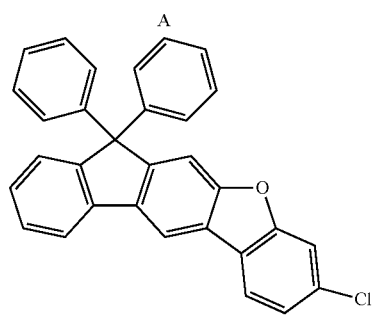
C
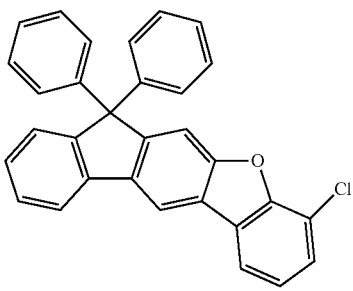
D
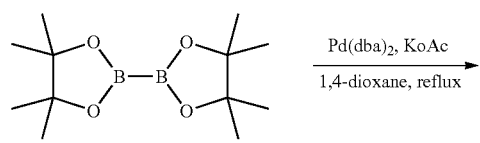
$\xrightarrow{\text{Pd(dba)}_2, \text{KoAc}}{\text{1,4-dioxane, reflux}}$

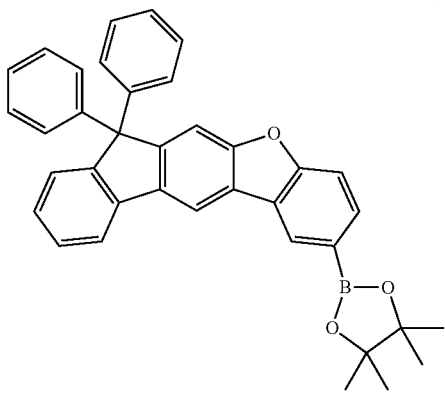

E

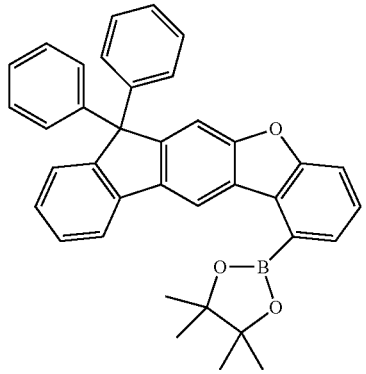

F

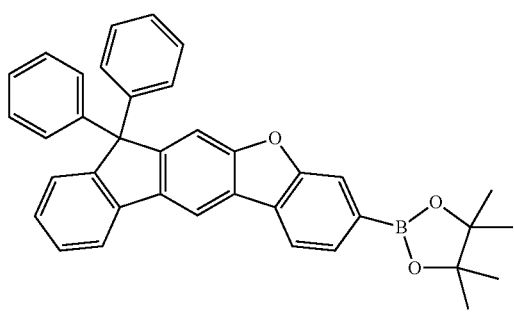

G

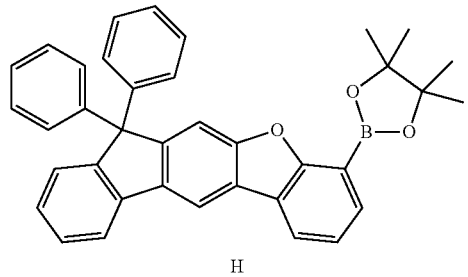

H

<Preparation Example 1> Preparation of Compound 1

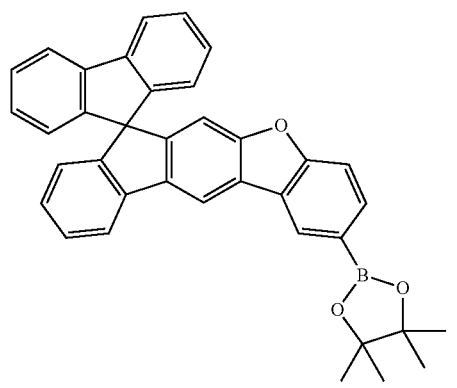

E

+

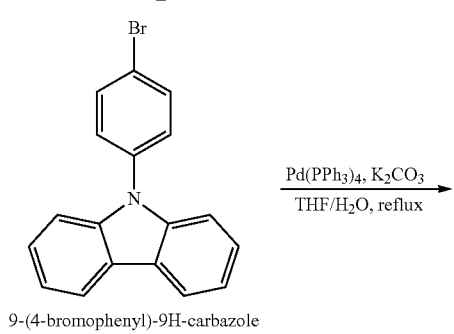

9-(4-bromophenyl)-9H-carbazole

Pd(PPh₃)₄, K₂CO₃
THF/H₂O, reflux
→

-continued

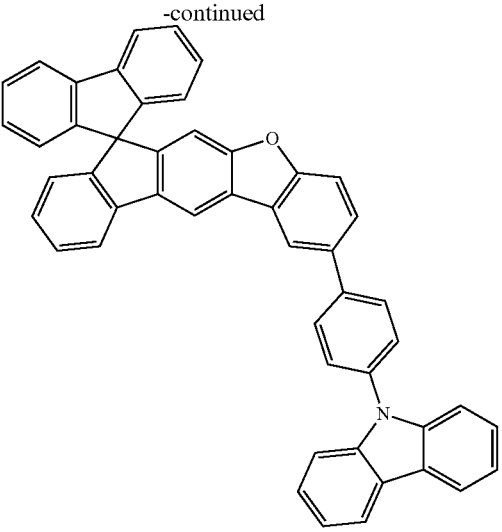

Compound E (18.23 g, 34.27 mmol) and 9-(4-bromophenyl)-9H-carbazole (10.00 g, 31.15 mmol) were completely dissolved in 320 ml of tetrahydrofuran in a 500-ml round bottom flask under a nitrogen atmosphere, and then an aqueous 2 M potassium carbonate solution (160 ml) was added thereto, tetrakis-(triphenylphosphine)palladium (1.08 g, 0.93 mmol) was put thereinto, and then the resulting mixture was heated and stirred for 3 hours. The temperature was lowered to room temperature, the aqueous layer was removed, and the residue was dried over anhydrous magnesium sulfate, and then concentrated under reduced pressure, and recrystallized with 220 ml of ethyl acetate to prepare Compound 1 (17.92 g, yield: 89%).

MS[M+H]$^+$=648

<Preparation Example 2> Preparation of Compound 2

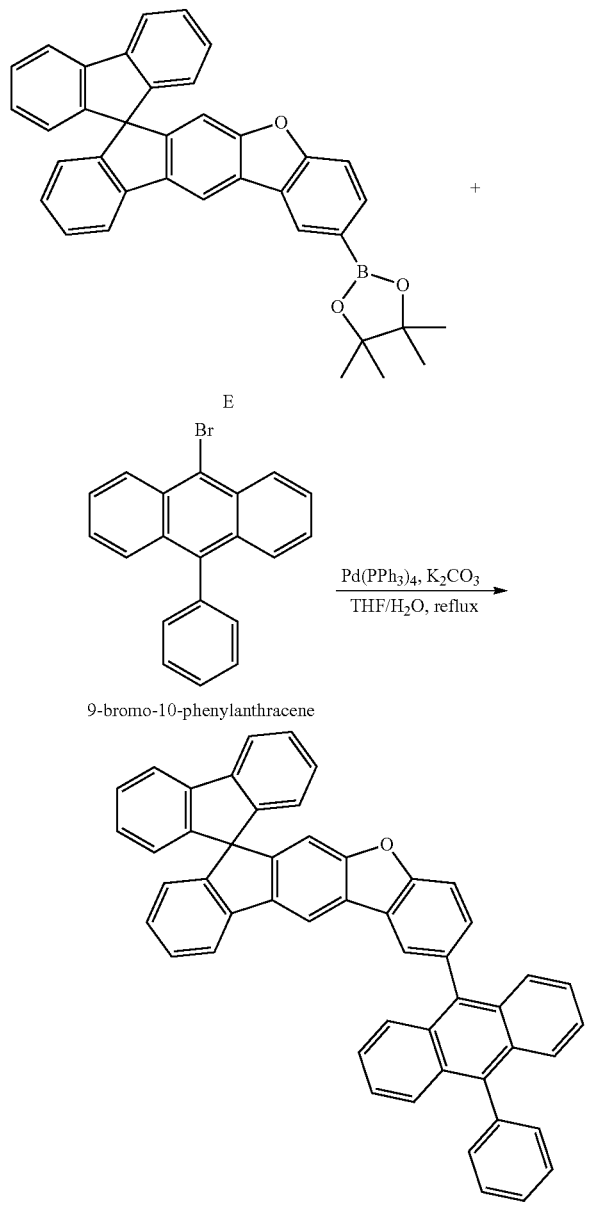

<Preparation Example 3> Preparation of Compound 3

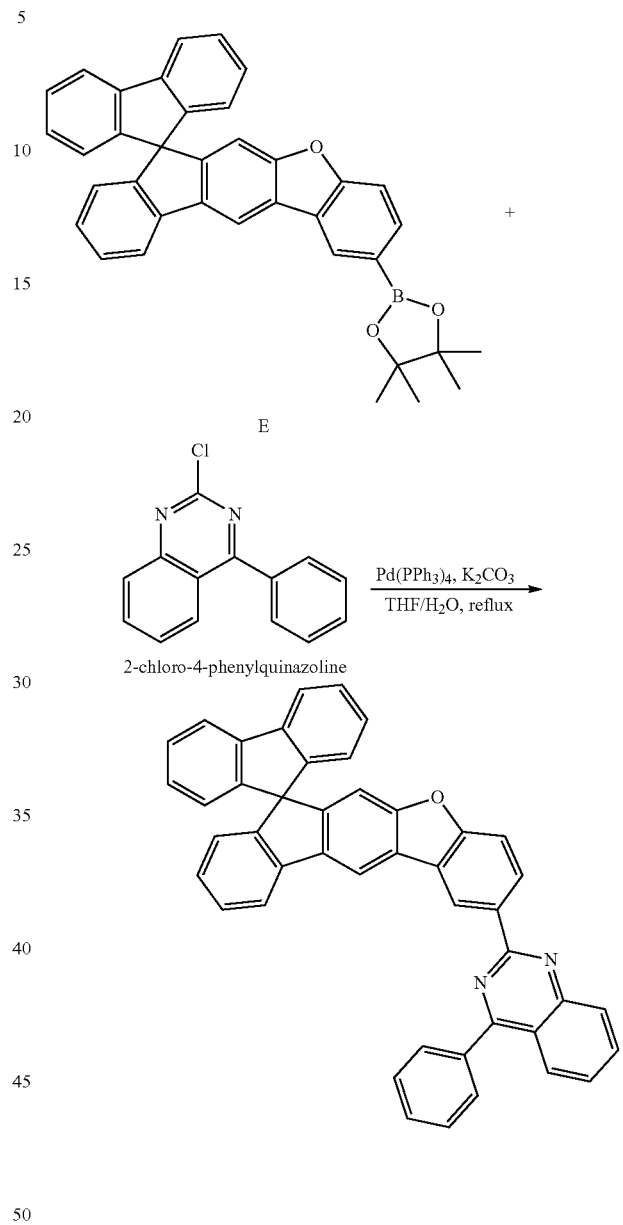

Compound E (17.63 g, 33.13 mmol) and 9-bromo-10-phenylanthracene (10.00 g, 30.12 mmol) were completely dissolved in 280 ml of tetrahydrofuran in a 500-ml round bottom flask under a nitrogen atmosphere, and then an aqueous 2 M potassium carbonate solution (140 ml) was added thereto, tetrakis-(triphenylphosphine)palladium (1.08 g, 0.93 mmol) was put thereinto, and then the resulting mixture was heated and stirred for 6 hours. The temperature was lowered to room temperature, the aqueous layer was removed, and the residue was dried over anhydrous magnesium sulfate, and then concentrated under reduced pressure, and recrystallized with 250 ml of toluene to prepare Compound 2 (13.47 g, yield: 68%).

MS[M+H]$^+$=659

Compound E (12.19 g, 22.92 mmol) and 2-chloro-4-phenylquinazoline (5.0 g, 20.83 mmol) were completely dissolved in 180 ml of tetrahydrofuran in a 500-ml round bottom flask under a nitrogen atmosphere, and then an aqueous 2 M potassium carbonate solution (90 ml) was added thereto, tetrakis-(triphenylphosphine)palladium (0.72 g, 0.63 mmol) was put thereinto, and then the resulting mixture was heated and stirred for 1 hour. The temperature was lowered to room temperature, the aqueous layer was removed, and the residue was dried over anhydrous magnesium sulfate, and then concentrated under reduced pressure, and recrystallized with 210 ml of tetrahydrofuran to prepare Compound 3 (8.95 g, yield: 70%).

MS[M+H]$^+$=611

<Preparation Example 4> Preparation of Compound 4

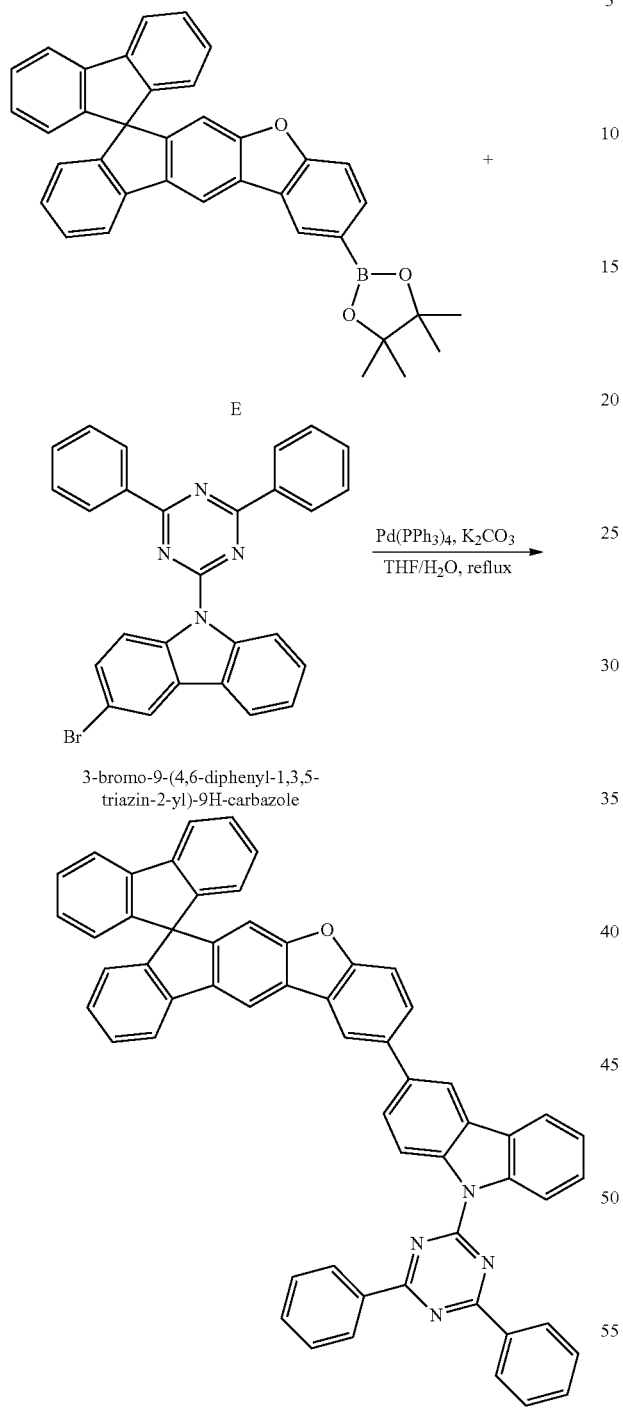

Compound E (12.29 g, 23.11 mmol) and 3-bromo-9-(4,6-diphenyl-1,3,5-triazin-2-yl)-9H-carbazole (10.0 g, 21.01 mmol) were completely dissolved in 320 ml of tetrahydrofuran in a 1,000-ml round bottom flask under a nitrogen atmosphere, and then an aqueous 2 M potassium carbonate solution (160 ml) was added thereto, tetrakis-(triphenylphosphine)palladium (0.73 g, 0.63 mmol) was put thereinto, and then the resulting mixture was heated and stirred for 2 hours. The temperature was lowered to room temperature, the aqueous layer was removed, and the residue was dried over anhydrous magnesium sulfate, and then concentrated under reduced pressure, and recrystallized with 310 ml of tetrahydrofuran to prepare Compound 4 (12.21 g, yield: 72%).

$MS[M+H]^+=803$

<Preparation Example 5> Preparation of Compound 5

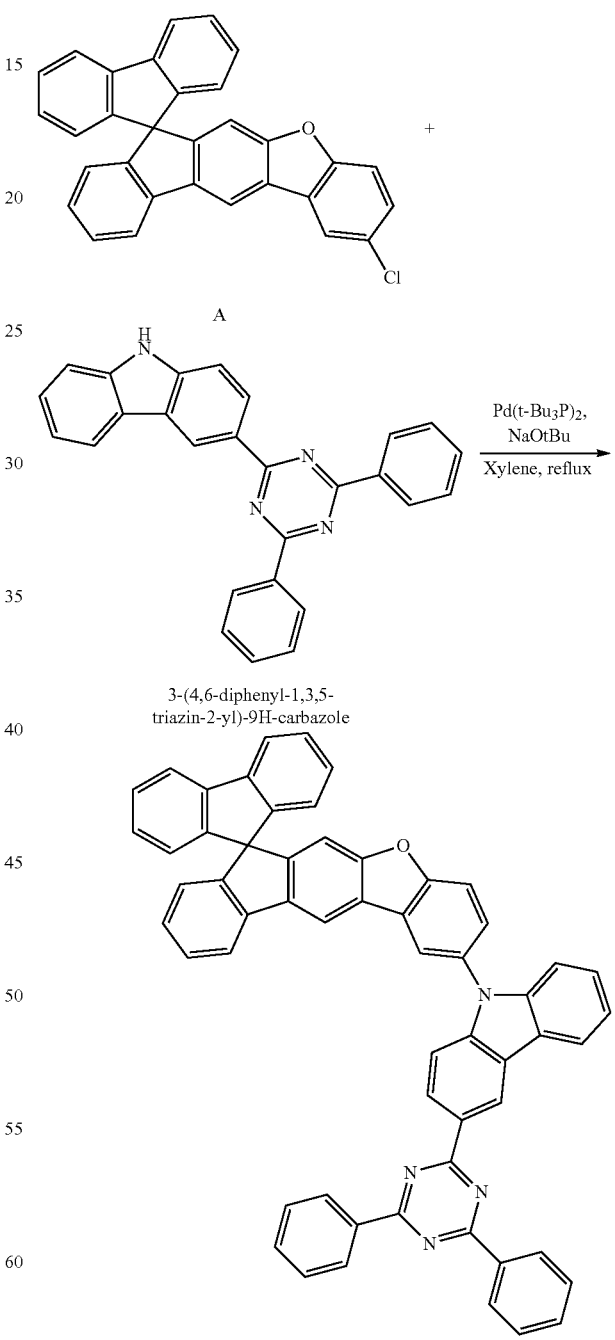

Compound A (10.0 g, 22.73 mmol) and 3-(4,6-diphenyl-1,3,5-triazin-2-yl)-9H-carbazole (9.95 g, 25.00 mmol) were completely dissolved in 180 ml of xylene in a 500 ml-round bottom flask under a nitrogen atmosphere, and then sodium tert-butoxide (2.84 g, 29.55 mol) was added thereto, bis(tri-tert-butylphosphine) palladium(0) (0.12 g, 0.23 mmol) was put thereinto, and then the resulting mixture was heated and stirred for 3 hours. The temperature was lowered to room temperature, the mixture was filtered to remove the base, and then xylene was concentrated under reduced pressure, and the residue was recrystallized with 170 ml of tetrahydrofuran to prepare Compound 5 (13.75 g, yield: 82%).

MS[M+H]$^+$=803

<Preparation Example 6> Preparation of Compound 6

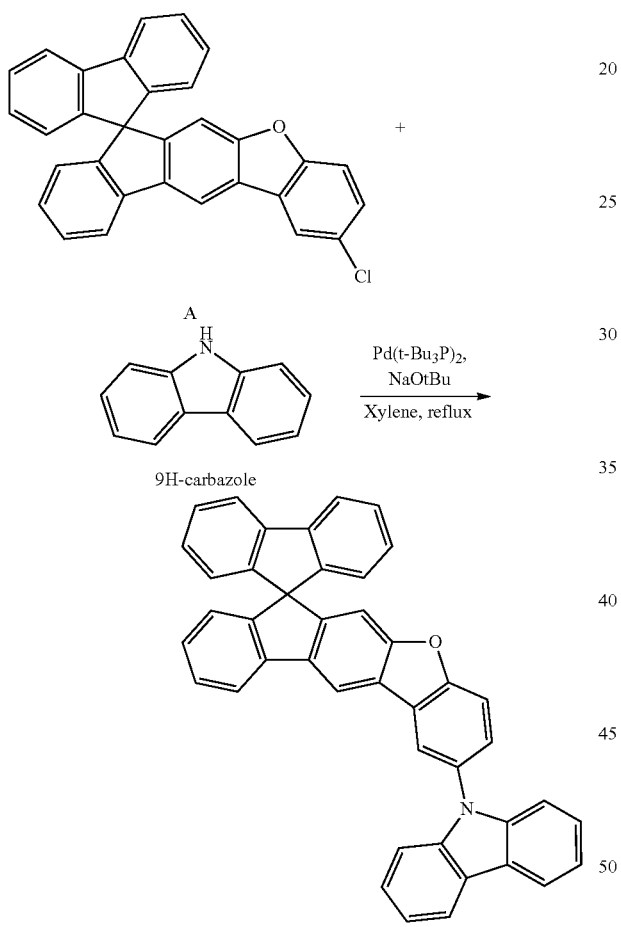

<Preparation Example 7> Preparation of Compound 7

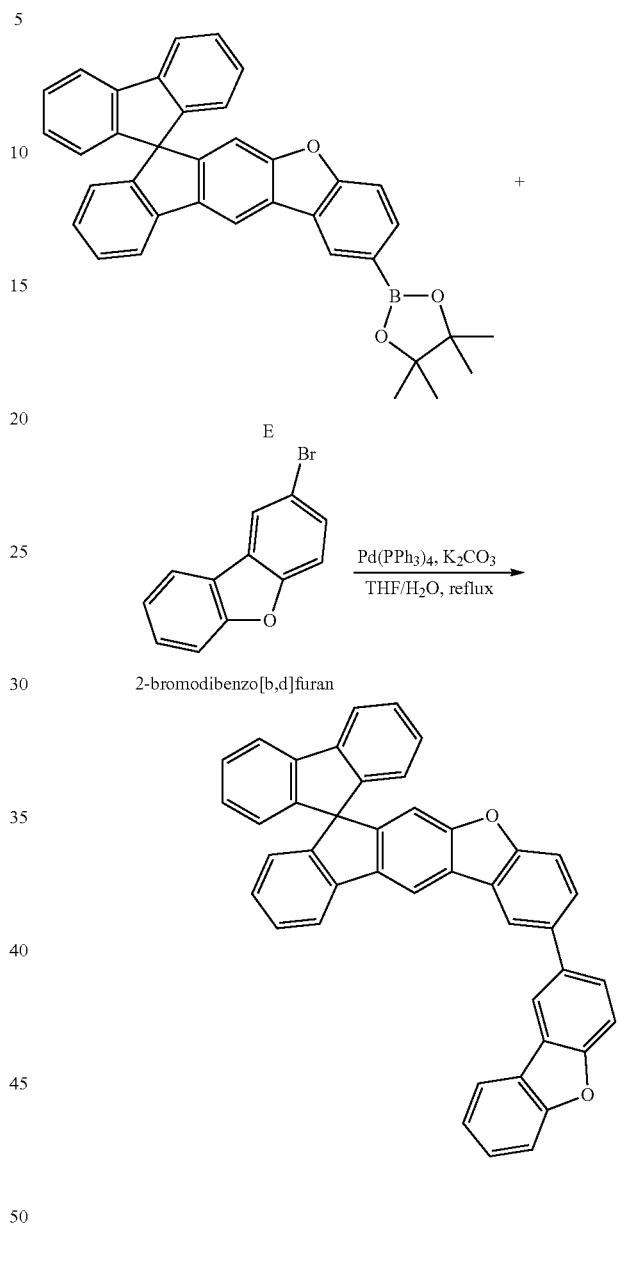

Compound A (10.0 g, 22.73 mmol) and 9H-carbazole (4.18 g, 25.00 mmol) were completely dissolved in 120 ml of xylene in a 500 ml-round bottom flask under a nitrogen atmosphere, and then sodium tert-butoxide (2.84 g, 29.55 mol) was added thereto, bis(tri-tert-butylphosphine) palladium(0) (0.12 g, 0.23 mmol) was put thereinto, and then the resulting mixture was heated and stirred for 5 hours. The temperature was lowered to room temperature, the mixture was filtered to remove the base, and then xylene was concentrated under reduced pressure, and the residue was recrystallized with 120 ml of ethyl acetate to prepare Compound 6 (8.45 g, yield: 70%).

MS[M+H]$^+$=571

Compound E (14.33 g, 26.94 mmol) and 2-bromodibenzo [b,d]furan (6.00 g, 24.49 mmol) were completely dissolved in 220 ml of tetrahydrofuran in a 500-ml round bottom flask under a nitrogen atmosphere, and then an aqueous 2 M potassium carbonate solution (110 ml) was added thereto, tetrakis-(triphenylphosphine)palladium (0.85 g, 0.73 mmol) was put thereinto, and then the resulting mixture was heated and stirred for 5 hours. The temperature was lowered to room temperature, the aqueous layer was removed, and the residue was dried over anhydrous magnesium sulfate, and then concentrated under reduced pressure, and recrystallized with 260 ml of ethyl acetate to prepare Compound 7 (10.21 g, yield: 73%).

MS[M+H]$^+$=573

<Preparation Example 8> Preparation of Compound 8

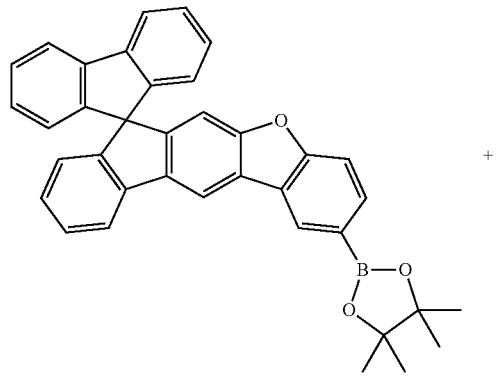

+

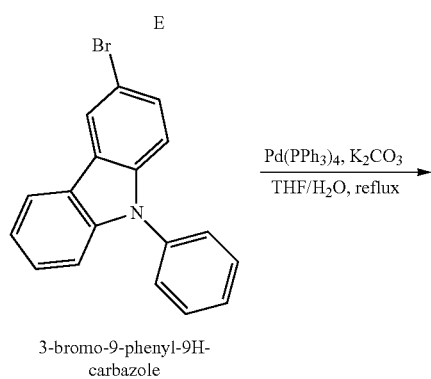

3-bromo-9-phenyl-9H-carbazole

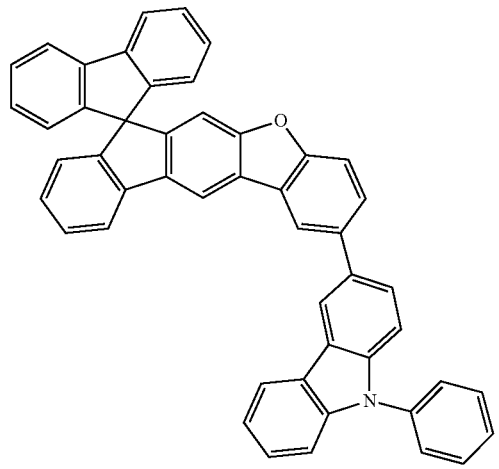

Compound E (14.58 g, 27.41 mmol) and 3-bromo-9-phenyl-9H-carbazole (8.00 g, 24.92 mmol) were completely dissolved in 200 ml of tetrahydrofuran in a 500-ml round bottom flask under a nitrogen atmosphere, and then an aqueous 2 M potassium carbonate solution (100 ml) was added thereto, tetrakis-(triphenylphosphine)palladium (0.86 g, 0.75 mmol) was put thereinto, and then the resulting mixture was heated and stirred for 2 hours. The temperature was lowered to room temperature, the aqueous layer was removed, and the residue was dried over anhydrous magnesium sulfate, and then concentrated under reduced pressure, and recrystallized with 210 ml of ethyl acetate to prepare Compound 8 (13.17 g, yield: 82%).

MS[M+H]$^+$=648

<Preparation Example 9> Preparation of Compound 9

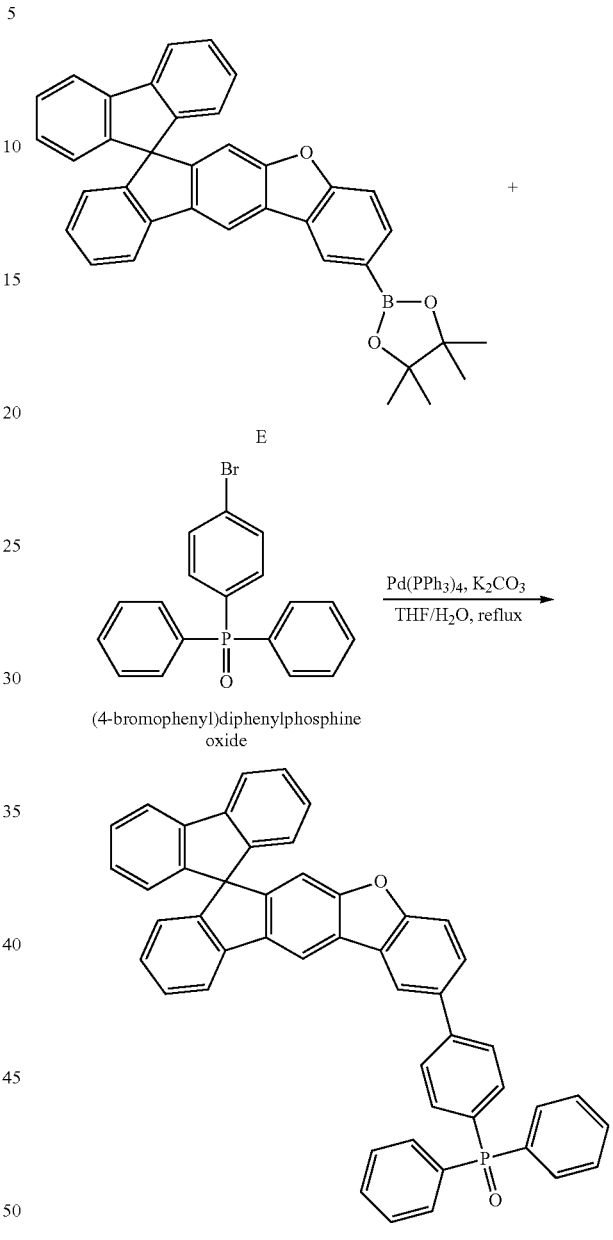

Compound E (16.44 g, 30.90 mmol) and (4-bromophenyl)diphenylphosphine oxide (10.00 g, 28.09 mmol) were completely dissolved in 180 ml of tetrahydrofuran in a 500-ml round bottom flask under a nitrogen atmosphere, and then an aqueous 2 M potassium carbonate solution (90 ml) was added thereto, tetrakis-(triphenylphosphine)palladium (0.97 g, 0.84 mmol) was put thereinto, and then the resulting mixture was heated and stirred for 2 hours. The temperature was lowered to room temperature, the aqueous layer was removed, and the residue was dried over anhydrous magnesium sulfate, and then concentrated under reduced pressure, and recrystallized with 210 ml of ethyl acetate to prepare Compound 9 (16.95 g, yield: 88%).

MS[M+H]$^+$=683

<Preparation Example 10> Preparation of Compound 10

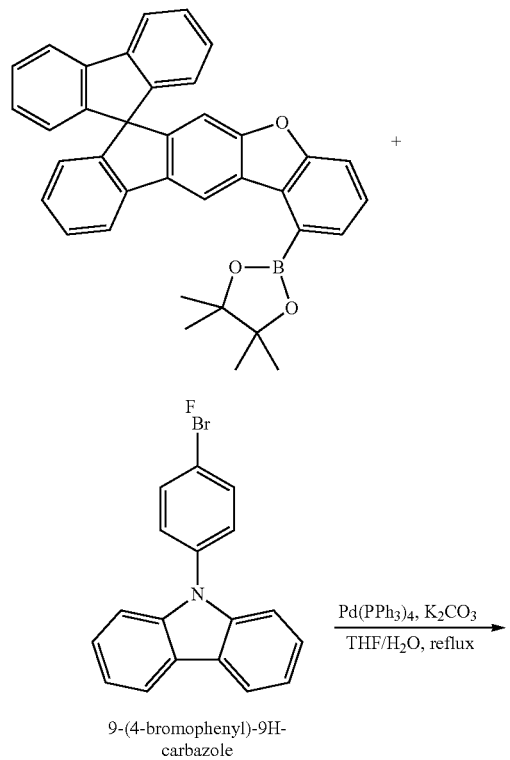

9-(4-bromophenyl)-9H-carbazole

Compound F (18.23 g, 34.27 mmol) and 9-(4-bromophenyl)-9H-carbazole (10.00 g, 31.15 mmol) were completely dissolved in 320 ml of tetrahydrofuran in a 500-ml round bottom flask under a nitrogen atmosphere, and then an aqueous 2 M potassium carbonate solution (160 ml) was added thereto, tetrakis-(triphenylphosphine)palladium (1.08 g, 0.93 mmol) was put thereinto, and then the resulting mixture was heated and stirred for 4 hours. The temperature was lowered to room temperature, the aqueous layer was removed, and the residue was dried over anhydrous magnesium sulfate, and then concentrated under reduced pressure, and recrystallized with 250 ml of ethyl acetate to prepare Compound 10 (16.17 g, yield: 80%).

MS[M+H]$^+$=648

<Preparation Example 11> Preparation of Compound 11

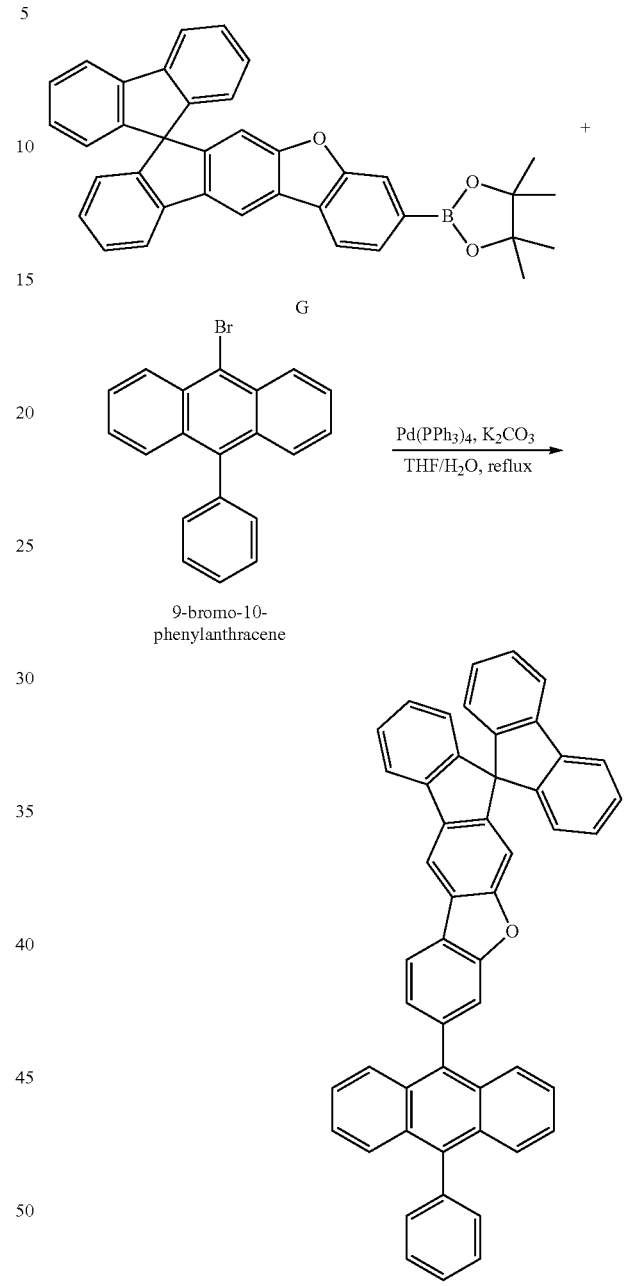

9-bromo-10-phenylanthracene

Compound G (17.63 g, 33.13 mmol) and 9-bromo-10-phenylanthracene (10.00 g, 30.12 mmol) were completely dissolved in 210 ml of tetrahydrofuran in a 500-ml round bottom flask under a nitrogen atmosphere, and then an aqueous 2 M potassium carbonate solution (100 ml) was added thereto, tetrakis-(triphenylphosphine)palladium (1.04 g, 0.91 mmol) was put thereinto, and then the resulting mixture was heated and stirred for 4 hours. The temperature was lowered to room temperature, the aqueous layer was removed, and the residue was dried over anhydrous magnesium sulfate, and then concentrated under reduced pressure, and recrystallized with 220 ml of toluene to prepare Compound 11 (15.07 g, yield: 76%).

MS[M+H]$^+$=659

<Preparation Example 12> Preparation of Compound 12

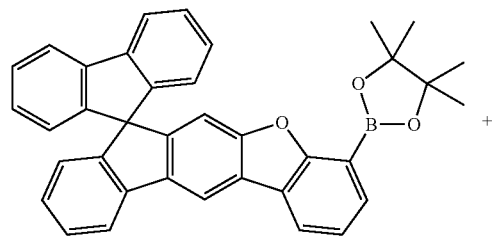

H

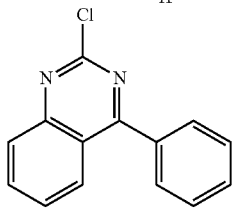

2-chloro-4-phenylquinazoline

Pd(PPh₃)₄, K₂CO₃
THF/H₂O, reflux

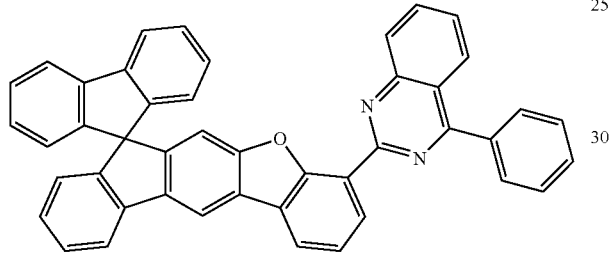

Compound H (12.19 g, 22.92 mmol) and 2-chloro-4-phenylquinazoline (5.0 g, 20.83 mmol) were completely dissolved in 180 ml of tetrahydrofuran in a 500-ml round bottom flask under a nitrogen atmosphere, and then an aqueous 2 M potassium carbonate solution (90 ml) was added thereto, tetrakis-(triphenylphosphine)palladium (0.72 g, 0.63 mmol) was put thereinto, and then the resulting mixture was heated and stirred for 1 hour. The temperature was lowered to room temperature, the aqueous layer was removed, and the residue was dried over anhydrous magnesium sulfate, and then concentrated under reduced pressure, and recrystallized with 210 ml of tetrahydrofuran to prepare Compound 12 (7.89 g, yield: 62%).

MS[M+H]⁺=611

<Preparation Example 13> Preparation of Compound 13

-continued

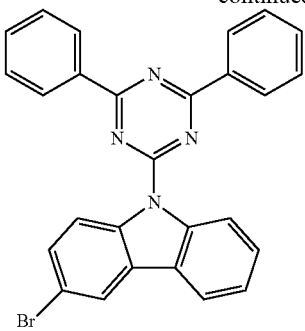

3-bromo-9-(4,6-diphenyl-1,3,5-triazin-2-yl)-9H-carbazole

Pd(PPh₃)₄, K₂CO₃
THF/H₂O, reflux

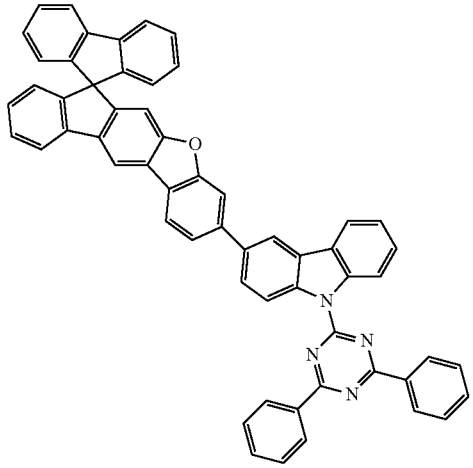

Compound G (12.29 g, 23.11 mmol) and 3-bromo-9-(4,6-diphenyl-1,3,5-triazin-2-yl)-9H-carbazole (10.0 g, 21.01 mmol) were completely dissolved in 320 ml of tetrahydrofuran in a 1,000-ml round bottom flask under a nitrogen atmosphere, and then an aqueous 2 M potassium carbonate solution (160 ml) was added thereto, tetrakis-(triphenylphosphine)palladium (0.73 g, 0.63 mmol) was put thereinto, and then the resulting mixture was heated and stirred for 2 hours. The temperature was lowered to room temperature, the aqueous layer was removed, and the residue was dried over anhydrous magnesium sulfate, and then concentrated under reduced pressure, and recrystallized with 310 ml of tetrahydrofuran to prepare Compound 13 (10.98 g, yield: 64%).

MS[M+H]⁺=803

<Preparation Example 14> Preparation of Compound 14

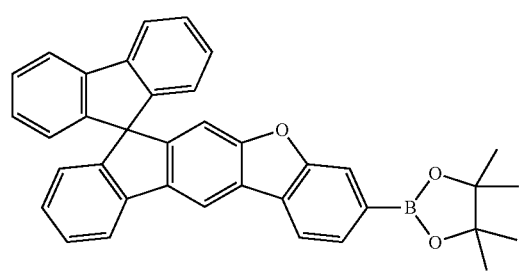

G

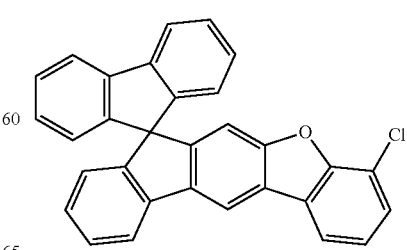

H

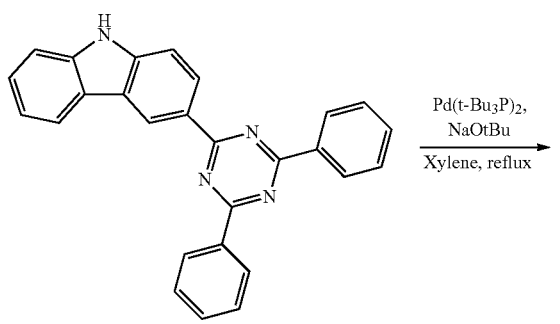

3-(4,6-diphenyl-1,3,5-triazin-2-yl)-9H-carbozole

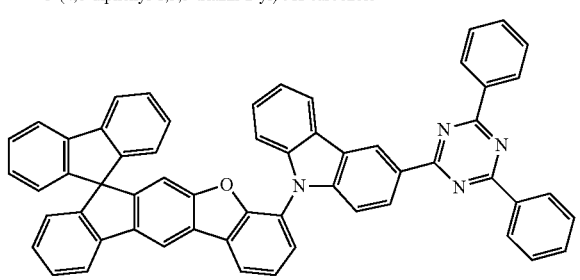

Compound H (10.0 g, 22.73 mmol) and 3-(4,6-diphenyl-1,3,5-triazin-2-yl)-9H-carbazole (9.95 g, 25.00 mmol) were completely dissolved in 180 ml of xylene in a 500 ml-round bottom flask under a nitrogen atmosphere, and then sodium tert-butoxide (2.84 g, 29.55 mol) was added thereto, bis(tri-tert-butylphosphine) palladium(0) (0.12 g, 0.23 mmol) was put thereinto, and then the resulting mixture was heated and stirred for 2 hours. The temperature was lowered to room temperature, the mixture was filtered to remove the base, and then xylene was concentrated under reduced pressure, and the residue was recrystallized with 190 ml of tetrahydrofuran to prepare Compound 14 (12.38 g, yield: 75%).

MS[M+H]$^+$=803

<Preparation Example 15> Preparation of Compound 15

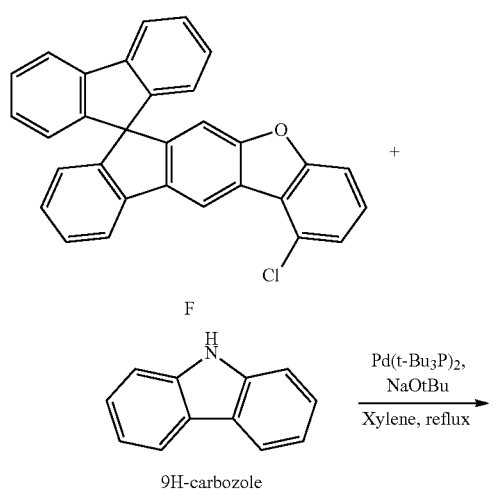

9H-carbozole

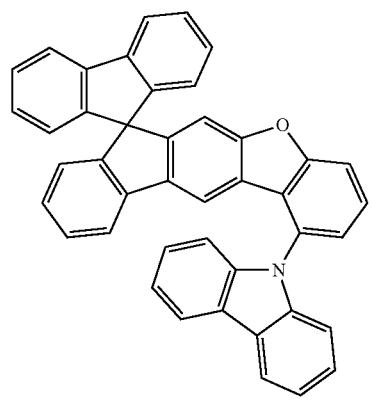

Compound F (10.0 g, 22.73 mmol) and 9H-carbazole (4.18 g, 25.00 mmol) were completely dissolved in 120 ml of xylene in a 500 ml-round bottom flask under a nitrogen atmosphere, and then sodium tert-butoxide (2.84 g, 29.55 mol) was added thereto, bis(tri-tert-butylphosphine) palladium(0) (0.12 g, 0.23 mmol) was put thereinto, and then the resulting mixture was heated and stirred for 3 hours. The temperature was lowered to room temperature, the mixture was filtered to remove the base, and then xylene was concentrated under reduced pressure, and the residue was recrystallized with 160 ml of ethyl acetate to prepare Compound 15 (7.64 g, yield: 62%).

MS[M+H]$^+$=571

<Preparation Example 16> Preparation of Compound 16

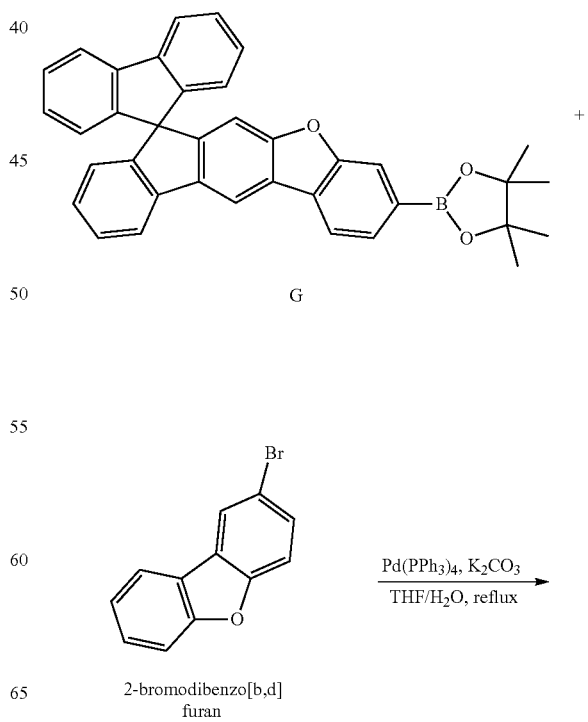

2-bromodibenzo[b,d]furan

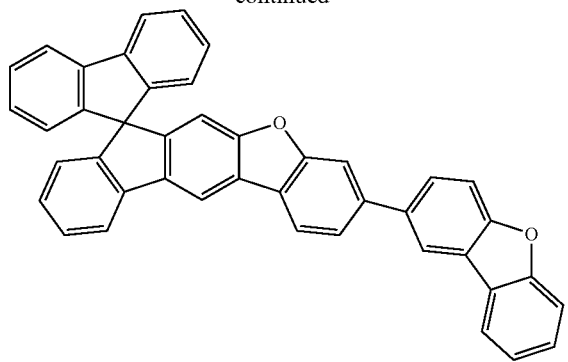

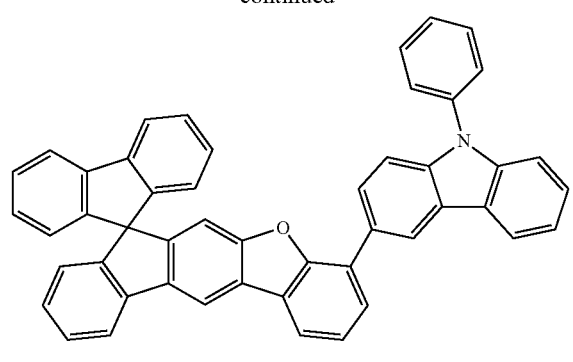

Compound G (14.33 g, 26.94 mmol) and 2-bromodibenzo[b,d]furan (6.00 g, 24.49 mmol) were completely dissolved in 220 ml of tetrahydrofuran in a 500-ml round bottom flask under a nitrogen atmosphere, and then an aqueous 2 M potassium carbonate solution (110 ml) was added thereto, tetrakis-(triphenylphosphine)palladium (0.85 g, 0.73 mmol) was put thereinto, and then the resulting mixture was heated and stirred for 4 hours. The temperature was lowered to room temperature, the aqueous layer was removed, and the residue was dried over anhydrous magnesium sulfate, and then concentrated under reduced pressure, and recrystallized with 210 ml of ethyl acetate to prepare Compound 16 (9.19 g, yield: 67%).

MS[M+H]$^+$=573

<Preparation Example 17> Preparation of Compound 17

Compound H (14.58 g, 27.41 mmol) and 3-bromo-9-phenyl-9H-carbazole (8.00 g, 24.92 mmol) were completely dissolved in 200 ml of tetrahydrofuran in a 500-ml round bottom flask under a nitrogen atmosphere, and then an aqueous 2 M potassium carbonate solution (100 ml) was added thereto, tetrakis-(triphenylphosphine)palladium (0.86 g, 0.75 mmol) was put thereinto, and then the resulting mixture was heated and stirred for 4 hours. The temperature was lowered to room temperature, the aqueous layer was removed, and the residue was dried over anhydrous magnesium sulfate, and then concentrated under reduced pressure, and recrystallized with 180 ml of ethyl acetate to prepare Compound 17 (11.86 g, yield: 73%).

MS[M+H]$^+$=648

<Preparation Example 18> Preparation of Compound 18

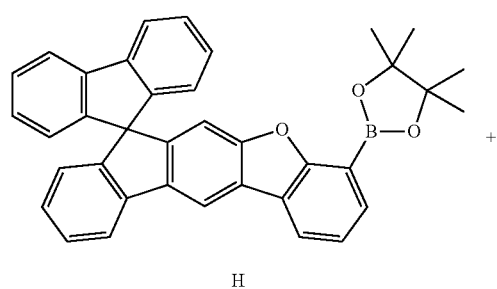

H

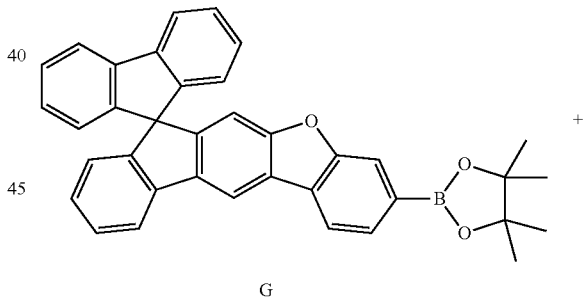

G

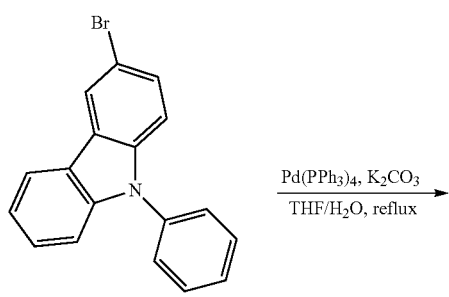

3-bromo-9-phenyl-9H-carbazole

Pd(PPh$_3$)$_4$, K$_2$CO$_3$
THF/H$_2$O, reflux →

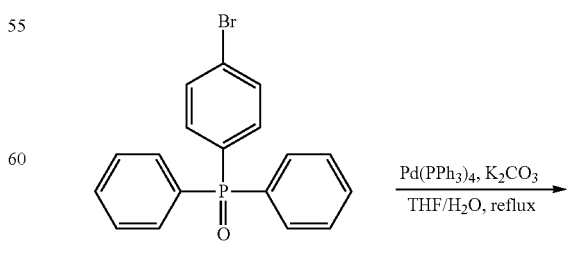

(4-bromophenyl)diphenylphosphine oxide

Pd(PPh$_3$)$_4$, K$_2$CO$_3$
THF/H$_2$O, reflux →

-continued

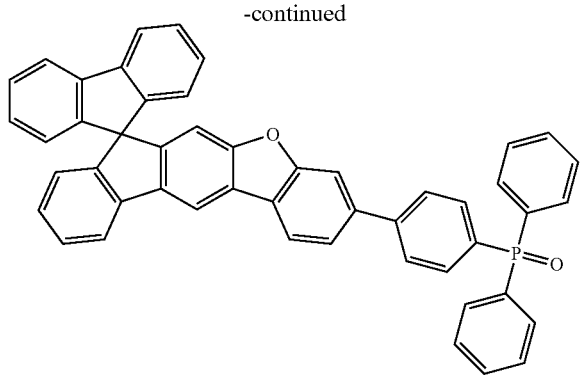

Compound G (16.44 g, 30.90 mmol) and (4-bromophenyl)diphenylphosphine oxide (10.00 g, 28.09 mmol) were completely dissolved in 180 ml of tetrahydrofuran in a 500-ml round bottom flask under a nitrogen atmosphere, and then an aqueous 2 M potassium carbonate solution (90 ml) was added thereto, tetrakis-(triphenylphosphine)palladium (0.97 g, 0.84 mmol) was put thereinto, and then the resulting mixture was heated and stirred for 3 hours. The temperature was lowered to room temperature, the aqueous layer was removed, and the residue was dried over anhydrous magnesium sulfate, and then concentrated under reduced pressure, and recrystallized with 220 ml of ethyl acetate to prepare Compound 18 (15.27 g, yield: 79%).
MS[M+H]$^+$=683

Experimental Example 1-1

A glass substrate on which a thin film of indium tin oxide (ITO) was coated to have a thickness of 1,000 Å was placed into distilled water in which a detergent was dissolved, and washed using ultrasonic waves. In this case, a product manufactured by Fischer Co., was used as the detergent, and distilled water twice filtered using a filter manufactured by Millipore Co., was used as the distilled water. After the ITO was washed for 30 minutes, ultrasonic washing was repeated twice using distilled water for 10 minutes. After the washing using distilled water was completed, ultrasonic washing was conducted using a solvent of isopropyl alcohol, acetone, and methanol, and the resultant product was dried and then transported to a plasma washing machine. Furthermore, the substrate was washed by using an oxygen plasma for 5 minutes, and then was transported to a vacuum deposition machine.

Hexanitrile hexaazatriphenylene (HAT) of the following Chemical Formula was thermally vacuum deposited to have a thickness of 500 Å on the thus prepared ITO transparent electrode, thereby forming a hole injection layer.

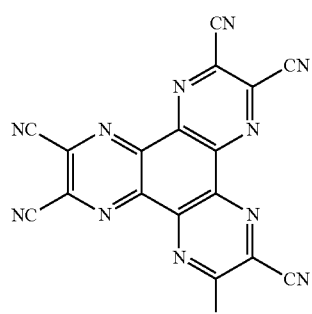

[HAT]

The following compound 4-4'-bis[N-(1-naphthyl)-N-phenylamino]biphenyl (NPB) (300 Å), which is a material for transporting holes, was vacuum deposited on the hole injection layer, thereby forming a hole transporting layer.

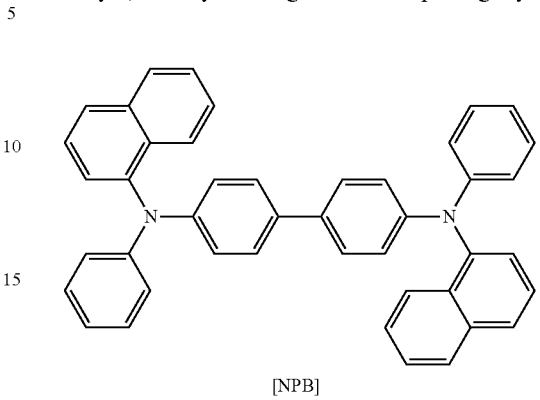

[NPB]

Subsequently, the following Compound 1 was vacuum deposited to have a film thickness of 100 Å on the hole transporting layer, thereby forming an electron blocking layer.

[Compound 1]

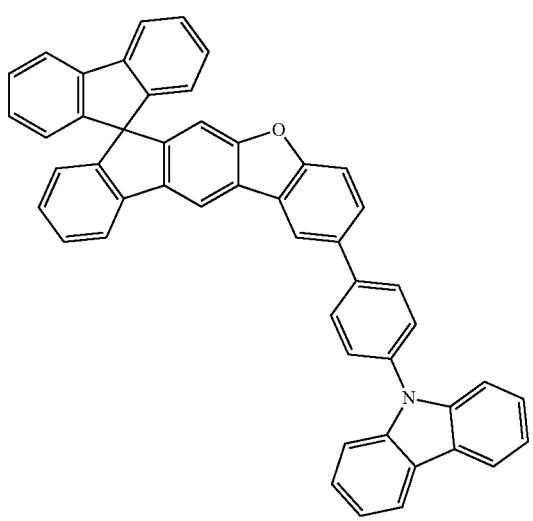

Subsequently, the following BH and BD were vacuum deposited at a weight ratio of 25:1 to have a film thickness of 300 Å on the electron blocking layer, thereby forming a light emitting layer.

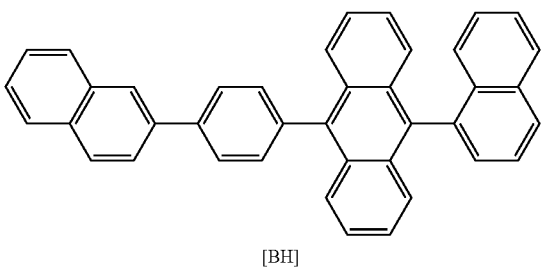

[BH]

-continued

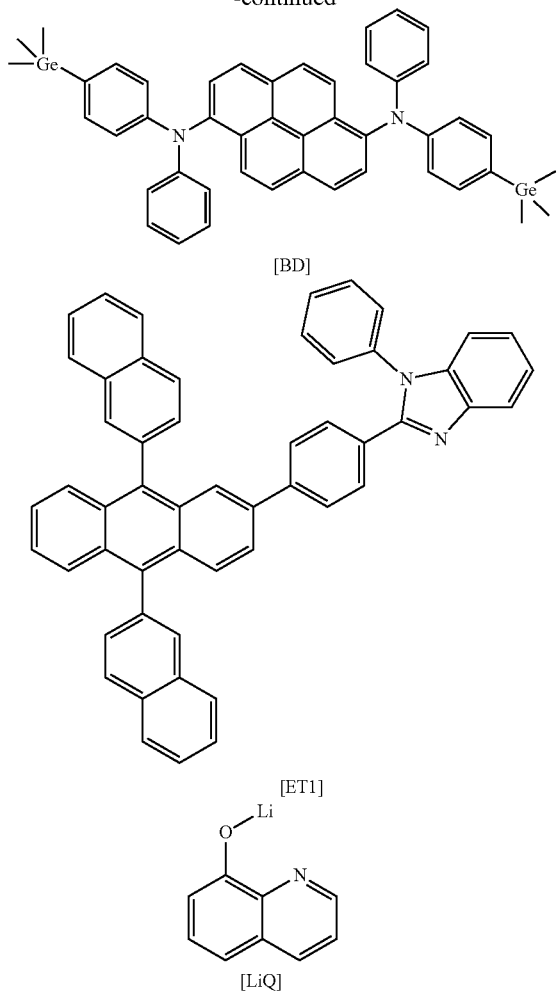

[BD]

[ET1]

[LiQ]

Compound ET1 and Compound LiQ (lithium quinolate) were vacuum deposited at a weight ratio of 1:1 on the light emitting layer, thereby forming an electron injection and transporting layer having a thickness of 300 Å. Lithium fluoride (LiF) and aluminum were subsequently deposited to have a thickness of 12 Å and 2,000 Å, respectively, on the electron injection and transporting layer, thereby forming a negative electrode.

In the aforementioned procedure, the deposition rate of the organic material was maintained at 0.4 to 0.7 Å/sec, the deposition rates of lithium fluoride and aluminum of the negative electrode were maintained at 0.3 Å/sec and at 2 Å/sec, respectively, and the degree of vacuum during the deposition was maintained at $2\times10^{-7}$ to $5\times10^{-6}$ torr, thereby manufacturing an organic light emitting device.

Experimental Example 1-2

An organic light emitting device was manufactured in the same manner as in Experimental Example 1-1, except that Compound 8 was used instead of Compound 1 in Experimental Example 1-1.

Experimental Example 1-3

An organic light emitting device was manufactured in the same manner as in Experimental Example 1-1, except that Compound 10 was used instead of Compound 1 in Experimental Example 1-1.

Experimental Example 1-4

An organic light emitting device was manufactured in the same manner as in Experimental Example 1-1, except that Compound 17 was used instead of Compound 1 in Experimental Example 1-1.

Comparative Example 1-1

An organic light emitting device was manufactured in the same manner as in Experimental Example 1-1, except that a compound of the following EB1 was used instead of Compound 1 in Experimental Example 1-1.

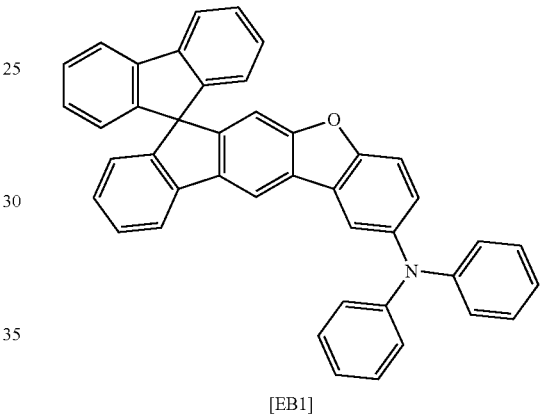

[EB1]

Comparative Example 1-2

An organic light emitting device was manufactured in the same manner as in Experimental Example 1-1, except that a compound of the following EB2 was used instead of Compound 1 in Experimental Example 1-1.

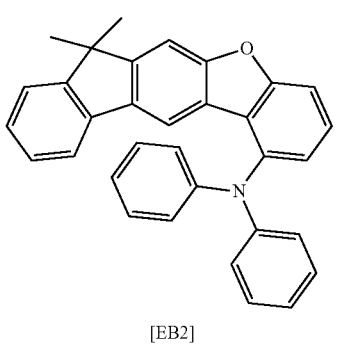 [SMILES: CC1(C)c2ccccc2-c2cc3c(cc21)oc1cccc(N(c2ccccc2)c2ccccc2)c13]

[EB2]

Comparative Example 1-3

An organic light emitting device was manufactured in the same manner as in Experimental Example 1-1, except that a compound of the following EB3 was used instead of Compound 1 in Experimental Example 1-1.

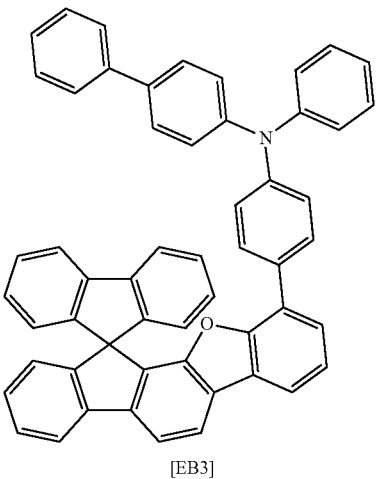 [SMILES: c1ccc(-c2ccc(N(c3ccccc3)c3ccc(-c4cccc5c4oc4c6c(ccc45)-c4ccccc4C64c5ccccc5-c5ccccc54)cc3)cc2)cc1]

[EB3]

Comparative Example 1-4

An organic light emitting device was manufactured in the same manner as in Experimental Example 1-1, except that a compound of the following EB4 was used instead of Compound 1 in Experimental Example 1-1.

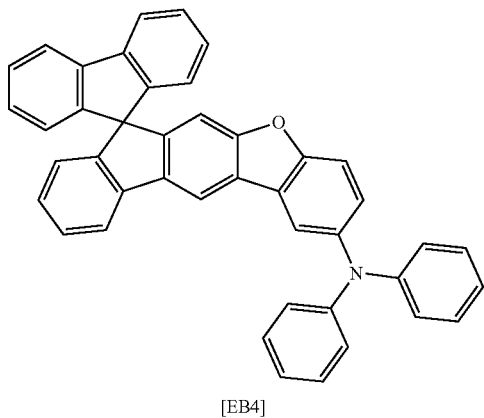 [SMILES: c1ccc(N(c2ccccc2)c2ccc3oc4cc5c(cc4c3c2)-c2ccccc2C52c3ccccc3-c3ccccc32)cc1]

[EB4]

When current was applied to the organic light emitting devices manufactured in Experimental Examples 1-1 to 1-4 and Comparative Examples 1-1 to 1-4, the results of Table 1 were obtained.

TABLE 1

| | Compound (Electron blocking layer) | Voltage (V@10 mA/cm$^2$) | Efficiency (cd/A@10 mA/cm$^2$) | Color coordinate (x, y) |
|---|---|---|---|---|
| Experimental Example 1-1 | Compound 1 | 3.53 | 6.47 | (0.137, 0.126) |
| Experimental Example 1-2 | Compound 8 | 3.67 | 6.32 | (0.136, 0.127) |
| Experimental Example 1-3 | Compound 10 | 3.58 | 6.41 | (0.137, 0.127) |
| Experimental Example 1-4 | Compound 17 | 3.64 | 6.38 | (0.136, 0.127) |

TABLE 1-continued

| | Compound (Electron blocking layer) | Voltage (V@10 mA/cm$^2$) | Efficiency (cd/A@10 mA/cm$^2$) | Color coordinate (x, y) |
|---|---|---|---|---|
| Comparative Example 1-1 | EB1 | 4.13 | 5.94 | (0.136, 0.127) |
| Comparative Example 1-2 | EB2 | 4.34 | 5.78 | (0.136, 0.127) |
| Comparative Example 1-3 | EB3 | 5.23 | 5.13 | (0.132, 0.122) |
| Comparative Example 1-4 | EB4 | 5.32 | 5.08 | (0.130, 0.121) |

The organic light emitting device manufactured by using the hetero-cyclic compound represented by Chemical Formula 1 according to the present specification as the electron blocking layer exhibits excellent characteristics in terms of efficiency, driving voltage, and/or stability of the organic light emitting device.

The organic light emitting devices using the hetero-cyclic compounds in Experimental Examples 1-1 to 1-4, in which L1 or Ar1 of Chemical Formula 1 according to the present specification is substituted with carbazole, as an electron blocking layer exhibit lower voltage and higher efficiency characteristics than the organic light emitting devices using the compounds in Comparative Examples 1-1 to 1-4, in which L1 or Ar1 is substituted with arylamine, in an electron blocking layer.

For the material substituted with arylamine, the barrier at the light emitting layer interface is increased while the HOMO value of the material is decreased, but the compounds of the present invention, which are substituted with carbazole, exhibit low voltage characteristics because the barrier at the light emitting layer interface is decreased while the HOMO values of the compounds is increased, and also exhibit high efficiency characteristics due to the increase in T1 value (carbazole>arylamine).

As in the result in Table 1, it could be confirmed that the hetero-cyclic compound represented by Chemical Formula 1 according to the present specification has an excellent electron blocking capability, and thus can be applied to an organic light emitting device.

Comparative Example 2-1

The compounds prepared in the Preparation Examples were subjected to high-purity sublimation purification by a typically known method, and then a green organic light emitting device was manufactured by the following method.

A glass substrate on which a thin film of indium tin oxide (ITO) was coated to have a thickness of 1,000 Å was placed into distilled water in which a detergent was dissolved, and washed using ultrasonic waves. In this case, a product manufactured by Fischer Co., was used as the detergent, and distilled water twice filtered using a filter manufactured by Millipore Co., was used as the distilled water. After the ITO was washed for 30 minutes, ultrasonic washing was repeated twice using distilled water for 10 minutes. After the washing using distilled water was completed, ultrasonic washing was conducted using a solvent of isopropyl alcohol, acetone, and methanol, and the resultant product was dried and then transported to a plasma washing machine. Furthermore, the substrate was washed by using an oxygen plasma for 5 minutes, and then was transported to a vacuum deposition machine.

An organic light emitting device was manufactured by configuring the light emitting device in the order of m-MT- DATA (60 nm)/TCTA (80 nm)/CBP+10% Ir(ppy)₃ (300 nm)/BCP (10 nm)/Alq₃ (30 nm)/LiF (1 nm)/Al (200 nm) on the thus prepared ITO transparent electrode by using CBP as a host. The structures of m-MTDATA, TCTA, Ir(ppy)₃, CBP, and BCP are as follows.

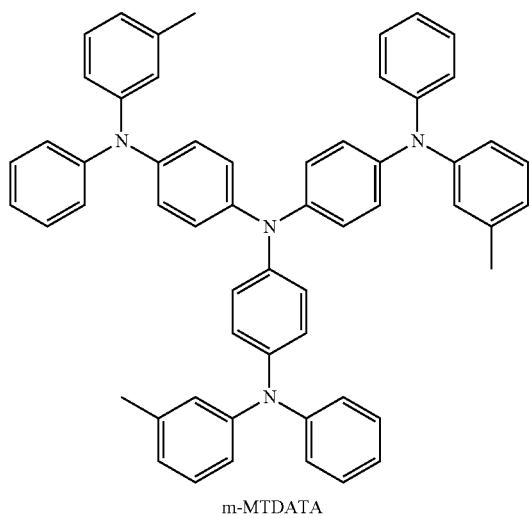
m-MTDATA

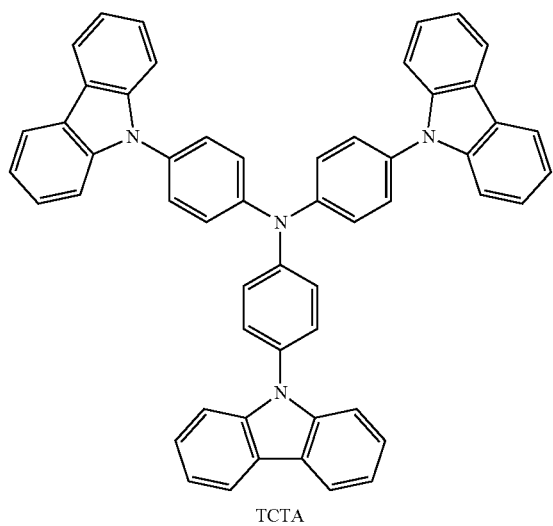
TCTA

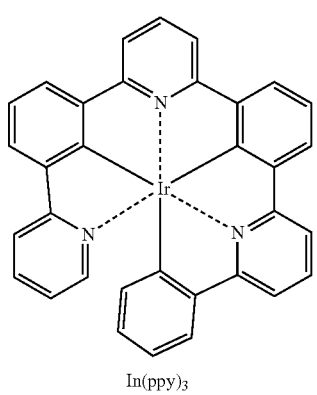
Ir(ppy)₃

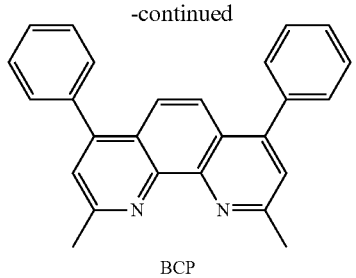
BCP

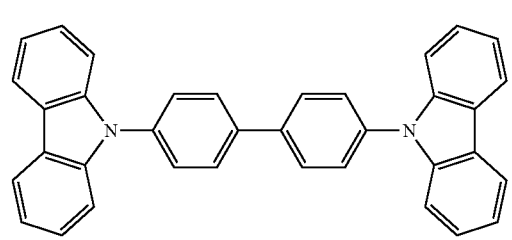
CBP

Experimental Example 2-1

An organic light emitting device was manufactured in the same manner as in Comparative Example 2-1, except that Compound 4 was used instead of Compound CBP in Comparative Example 2-1.

Experimental Example 2-2

An organic light emitting device was manufactured in the same manner as in Comparative Example 2-1, except that Compound 5 was used instead of Compound CBP in Comparative Example 2-1.

Experimental Example 2-3

An organic light emitting device was manufactured in the same manner as in Comparative Example 2-1, except that Compound 13 was used instead of Compound CBP in Comparative Example 2-1.

Experimental Example 2-4

An organic light emitting device was manufactured in the same manner as in Comparative Example 2-1, except that Compound 14 was used instead of Compound CBP in Comparative Example 2-1.

Comparative Example 2-2

An organic light emitting device was manufactured in the same manner as in Comparative Example 2-1, except that a compound of the following GH 1 was used instead of Compound CBP in Comparative Example 2-1.

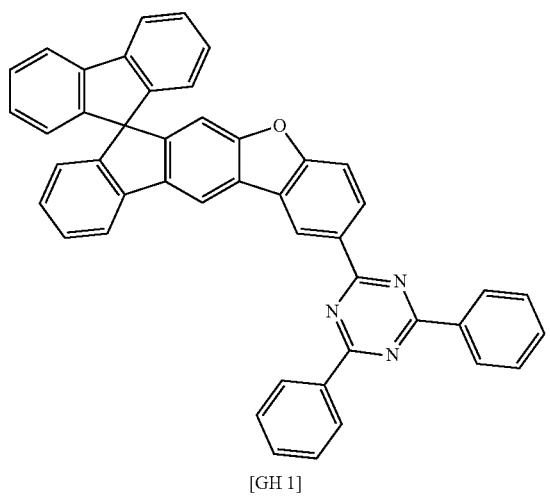 [SMILES: c1ccc(-c2nc(-c3ccccc3)nc(-c3ccc4oc5cc6c(cc5c4c3)-c3ccccc3C63c4ccccc4-c4ccccc43)n2)cc1]

[GH 1]

When current was applied to the organic light emitting devices manufactured in Experimental Examples 2-1 to 2-4 and Comparative Examples 2-1 and 2-2, the results of Table 2 were obtained.

TABLE 2

| | Compound (Host) | Voltage (V@10 mA/cm$^2$) | Efficiency (cd/A@10 mA/cm$^2$) | Light emitting peak (nm) |
|---|---|---|---|---|
| Comparative Example 2-1 | CBP | 7.45 | 38.62 | 516 |
| Experimental Example 2-1 | Compound 4 | 6.82 | 44.73 | 517 |
| Experimental Example 2-2 | Compound 5 | 6.96 | 42.53 | 516 |
| Experimental Example 2-3 | Compound 13 | 6.75 | 45.62 | 517 |
| Experimental Example 2-4 | Compound 14 | 6.88 | 42.82 | 517 |
| Comparative Example 2-2 | GH 1 | 7.06 | 41.25 | 516 |

As seen in Table 2, it could be confirmed that the green organic light emitting devices in Experimental Examples 2-1 to 2-4, in which the hetero-cyclic compound represented by Chemical Formula 1 according to the present specification was used as a host material of a light emitting layer, exhibited better performances in terms of current efficiency and driving voltage than the organic light emitting devices manufactured by using the compounds in Comparative Example 2-1, in which CBP in the related art was used, and Comparative Example 2-2, in which a ring was formed to have a structure similar to the core of Chemical Formula 1, as a host material.

Experimental Examples 3-1 and 3-2

The compounds prepared in the Preparation Examples were subjected to high-purity sublimation purification by a typically known method, and then red organic light emitting devices were manufactured by the following method.

An ITO glass was patterned and then washed, such that the light emitting area of the ITO glass became 2 mm×2 mm. The substrate was mounted into a vacuum chamber, and then the base pressure was allowed to be 1×10$^{-6}$ torr, and then for the organic material, DNTPD (700 Å), α-NPB (300 Å), and Compound 3 or 12 prepared in the Preparation Examples were used as a host (90 wt %) on the ITO, the following (piq)$_2$Ir(acac) (10 wt %) was co-deposited as a dopant, films were formed in the order of Alq$_3$ (350 Å), LiF (5 Å), and Al (1,000 Å), and measurements were made at 0.4 mA. The structures of DNTPD, α-NPB, (piq)$_2$Ir(acac), and Alq$_3$ are as follows.

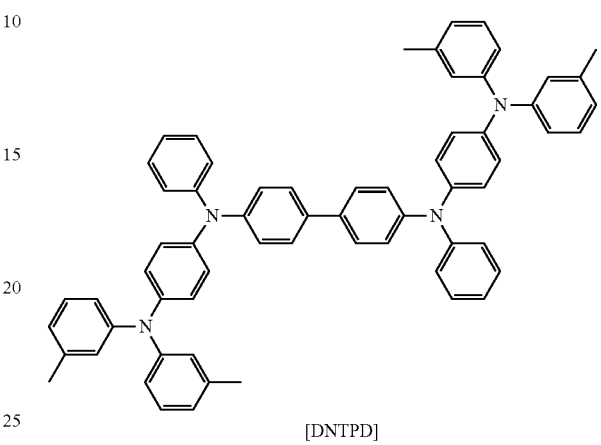

[DNTPD]

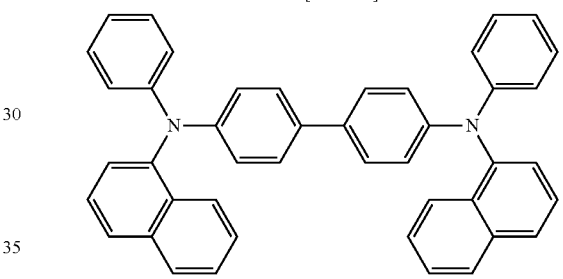

[α-NPB]

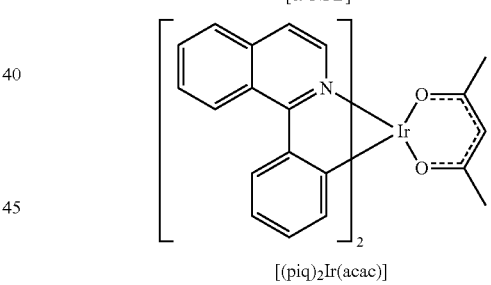

[(piq)$_2$Ir(acac)]

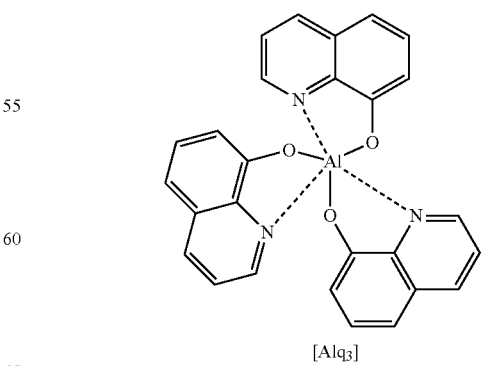

[Alq$_3$]

Comparative Example 3-1

An organic light emitting device was manufactured in the same manner as in Experimental Example 3-1, except that as a host of the light emitting layer, CBP was used instead of Compound 3 in Experimental Example 3-1.

For the organic light emitting devices manufactured by Experimental Examples 3-1 and 3-2 and Comparative Example 3-1, the voltages, current densities, luminances, color coordinates, and service lives were measured, and the results are shown in the following Table 3. T95 means the time taken for the luminance to be reduced to 95% of the initial luminance (5,000 nit).

TABLE 3

| Classification | Host | Dopant | Voltage (V) | Luminance (cd/m$^2$) | CIEx, CIEy | T95 (hr) |
|---|---|---|---|---|---|---|
| Experimental Example 3-1 | Compound 3 | [(piq)2Ir(acac)] | 4.6 | 1860 | 0.673, 0.326 | 395 |
| Experimental Example 3-2 | Compound 12 | [(piq)2Ir(acac)] | 4.9 | 1680 | 0.674, 0.325 | 390 |
| Comparative Example 3-1 | CBP | [(piq)2Ir(acac)] | 7.1 | 1420 | 0.670, 0.331 | 250 |

As seen in Table 3, it could be confirmed that the red organic light emitting devices in Experimental Examples 3-1 and 3-2 in which the hetero-cyclic compound represented by Chemical Formula 1 according to the present specification was used as a host material of the light emitting layer exhibited better performances in terms of current efficiency, driving voltage, and service life than the red organic light emitting device in Comparative Example 3-1 in which CBP in the related art was used.

Experimental Example 4-1

An experiment was performed in the same manner as in Experimental Example 1-1, except that the following compound TCTA was used instead of Compound 1 as the electron blocking layer, and Compound 4 was used instead of ET1 as the electron transporting layer.

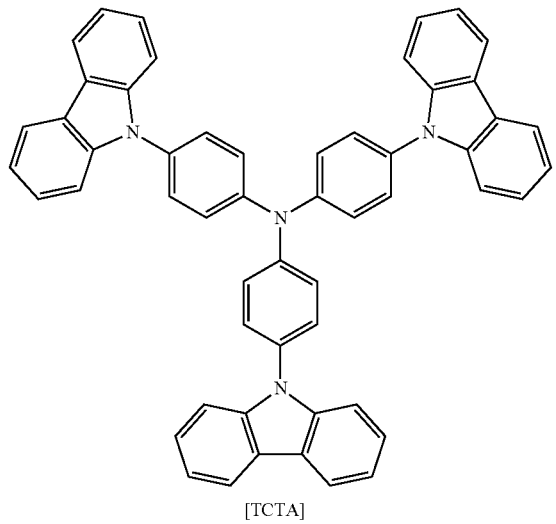 [SMILES: c1ccc2c(c1)c1ccccc1n2-c1ccc(N(c2ccc(-n3c4ccccc4c4ccccc43)cc2)c2ccc(-n3c4ccccc4c4ccccc43)cc2)cc1]

[TCTA]

Experimental Example 4-2

An experiment was performed in the same manner as in Experimental Example 4-1, except that as the electron transporting layer, Compound 5 was used instead of Compound 4.

Experimental Example 4-3

An experiment was performed in the same manner as in Experimental Example 4-1, except that as the electron transporting layer, Compound 9 was used instead of Compound 4.

Experimental Example 4-4

An experiment was performed in the same manner as in Experimental Example 4-1, except that as the electron transporting layer, Compound 13 was used instead of Compound 4.

Experimental Example 4-5

An experiment was performed in the same manner as in Experimental Example 4-1, except that as the electron transporting layer, Compound 14 was used instead of Compound 4.

Experimental Example 4-6

An experiment was performed in the same manner as in Experimental Example 4-1, except that as the electron transporting layer, Compound 18 was used instead of Compound 4.

Comparative Example 4-1

An experiment was performed in the same manner as in Experimental Example 4-1, except that as the electron transporting layer, a compound of the following ET2 was used instead of Compound 4.

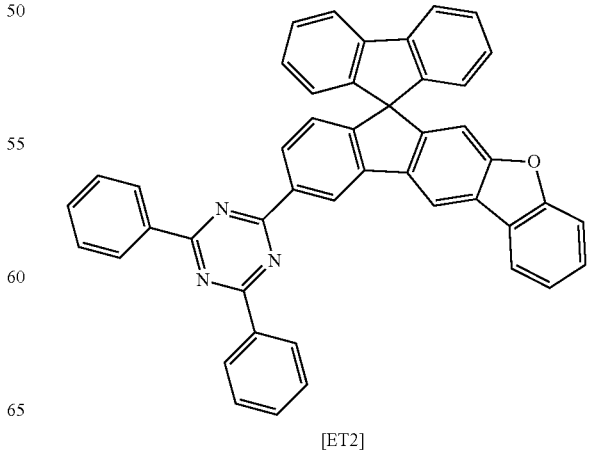

[ET2]

Comparative Example 4-2

An experiment was performed in the same manner as in Experimental Example 4-1, except that as the electron transporting layer, a compound of the following ET3 was used instead of Compound 4.

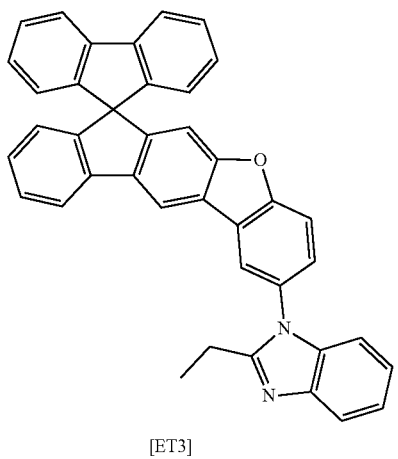 [SMILES: CCc1nc2ccccc2n1-c1ccc2oc3cc4c(cc3c2c1)-c1ccccc1C41c2ccccc2-c2ccccc21]

[ET3]

Comparative Example 4-3

An experiment was performed in the same manner as in Experimental Example 4-1, except that as the electron transporting layer, a compound of the following ET4 was used instead of Compound 4.

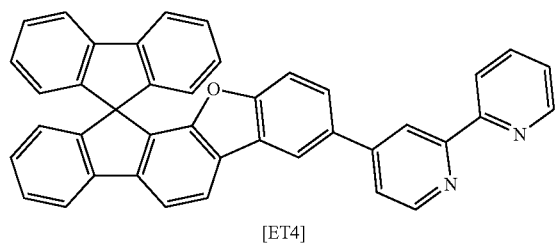 [SMILES: c1ccc(-c2cc(-c3ccc4oc5c6c(ccc5c4c3)-c3ccccc3C63c4ccccc4-c4ccccc43)ccn2)nc1]

[ET4]

For the organic light emitting devices manufactured by Experimental Examples 4-1 to 4-6 and Comparative Examples 4-1 to 4-3, the voltages, efficiencies, and color coordinates were measured, and the results are shown in the following Table 4. T95 means the time taken for the luminance to be reduced to 95% of the initial luminance (5,000 nit).

TABLE 4

| | Compound | Voltage (V@10 mA/cm$^2$) | Efficiency (cd/A@10 mA/cm$^2$) | Color coordinate (x, y) | T95 (hr) |
|---|---|---|---|---|---|
| Experimental Example 4-1 | Compound 4 | 3.78 | 4.91 | (0.138, 0.126) | 320 |
| Experimental Example 4-2 | Compound 5 | 3.55 | 4.95 | (0.139, 0.127) | 315 |
| Experimental Example 4-3 | Compound 9 | 3.66 | 4.85 | (0.138, 0.126) | 380 |
| Experimental Example 4-4 | Compound 13 | 3.65 | 4.82 | (0.138, 0.127) | 305 |
| Experimental Example 4-5 | Compound 14 | 3.69 | 4.65 | (0.137, 0.127) | 320 |
| Experimental Example 4-6 | Compound 18 | 3.75 | 4.64 | (0.138, 0.127) | 330 |
| Comparative Example 4-1 | ET2 | 4.17 | 4.37 | (0.136, 0.128) | 230 |
| Comparative Example 4-2 | ET3 | 4.37 | 4.05 | (0.138, 0.127) | 85 |
| Comparative Example 4-3 | ET4 | 4.52 | 3.52 | (0.132, 0.126) | 155 |

As a result of the experiments, it could be confirmed that the organic light emitting devices in Experimental Examples 4-1 to 4-6 in which the hetero-cyclic compound represented by Chemical Formula 1 according to the present specification was used as the electron transporting layer exhibited better performances in terms of current efficiency and driving voltage than the organic light emitting device in Comparative Example 4-1.

The service life of Experimental Example 4-3 having phosphine oxide as a substituent was measured as the longest. There were obtained the results that the material in Comparative Example 4-1, to which triazine is directly linked, had a high voltage, a benzimidazole group in which an alkyl group is substituted had a service life which led to a sudden death, and the ET4 material in Comparative Example 4-3, in which pyridine is substituted, had a reduced efficiency.

The service life of Experimental Example 4-3 using the compound substituted with phosphine oxide was measured as the longest. There were obtained the results that Comparative Example 4-1 using a compound in which triazine is directly linked to the core of Chemical Formula 1 had a high voltage, the service life of Comparative Example 4-2 using a compound substituted with an alkylbenzimidazole group was sharply decreased, and Comparative Example 4-3 using ET4 being a compound in which pyridine is substituted had a reduced efficiency.

Although the preferred exemplary embodiments (an electron blocking layer, a green light emitting layer, a red light emitting layer, and an electron transporting layer) of the present invention have been described above, the present invention is not limited thereto, and various modifications can be made and carried out within the scope of the claims and the detailed description of the invention, and also fall within the scope of the invention.

The invention claimed is:

1. A hetero-cyclic compound represented by the following Chemical Formula 1:

[Chemical Formula 1]

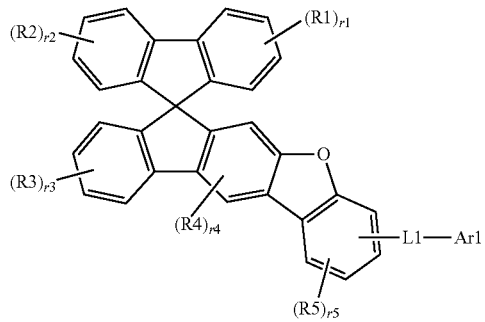

in Chemical Formula 1,

R1 to R5 are the same as or different from each other, and are each independently hydrogen; deuterium; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group, L1 is a direct bond;

Ar1 is a phosphine oxide group which is substituted with an aryl group; an aryl group which is unsubstituted or substituted with an alkyl group or an aryl group; or a tricyclic or tetracyclic heteroaryl group which is unsubstituted or substituted with an aryl group or a heteroaryl group which is unsubstituted or substituted with an aryl group, provided that when Ar1 is a phosphine oxide group which is substituted with an aryl group, L1 is a phenylene group, r1 and r2 are each an integer from 1 to 4, r3 is an integer from 1 to 4, r4 is 1 or 2, r5 is an integer from 1 to 3, and when r1 to r5 are each present in a plural number, a plurality of structures in the parenthesis is the same as or different from each other.

2. The hetero-cyclic compound of claim 1, wherein Chemical Formula 1 is represented by any one of the following Chemical Formula 2:

[Chemical Formula 2]

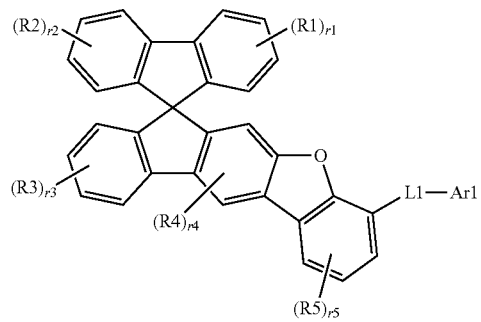

in Chemical Formula 2, the definitions of R1 to R5, r1 to r5, L1, and Ar1 are the same as those in Chemical Formula 1.

3. The hetero-cyclic compound of claim 1, wherein L1 is a direct bond; or a phenylene group.

4. The hetero-cyclic compound of claim 1, wherein Chemical Formula 1 is any one selected from the following compounds:

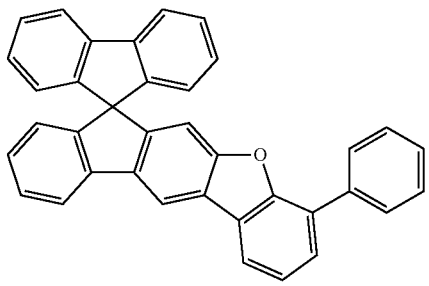

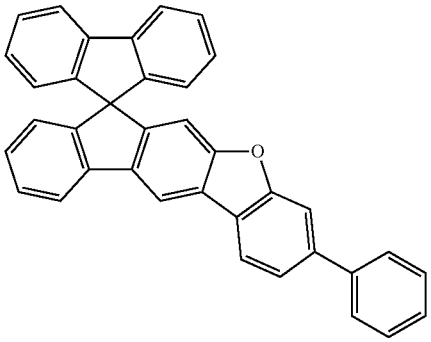

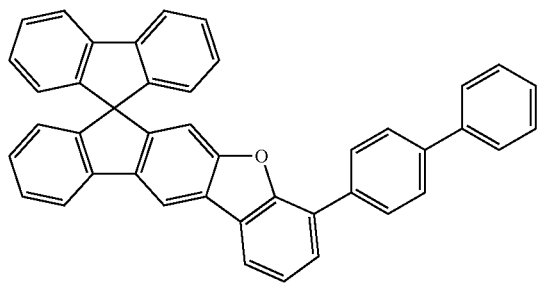

123
-continued
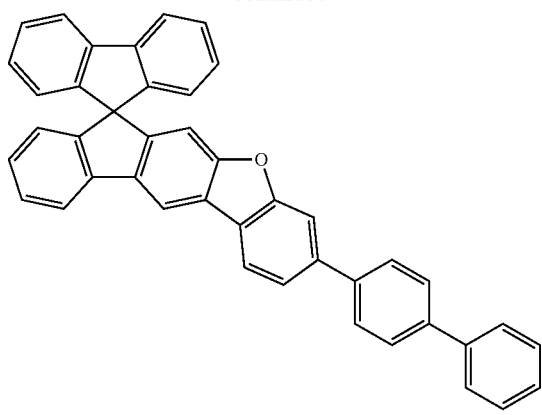
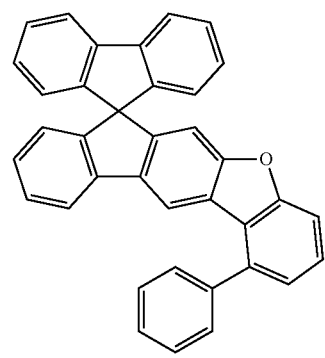
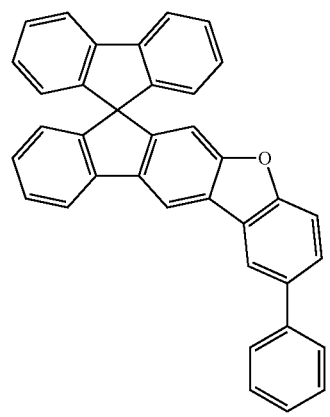
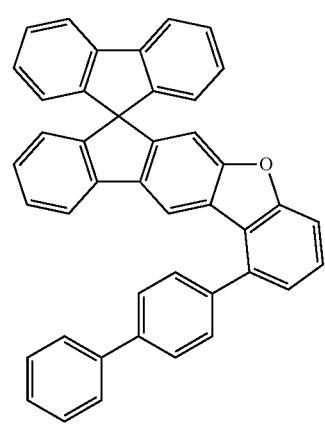
124
-continued
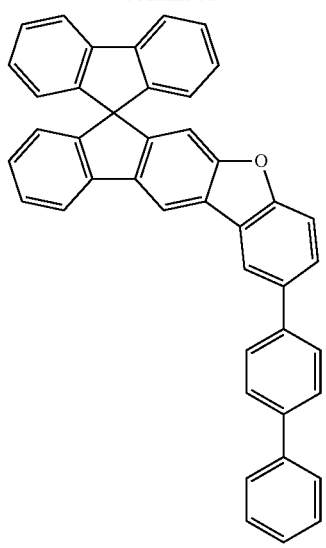
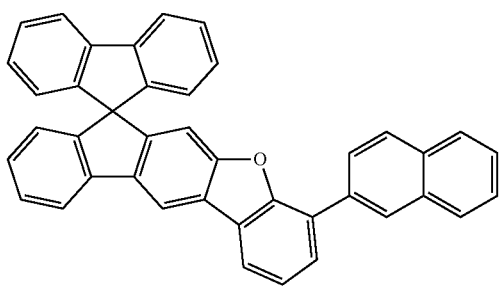
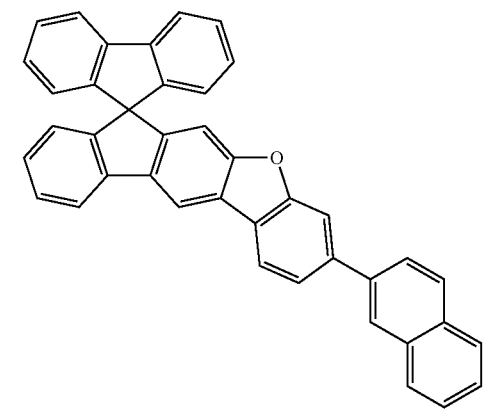
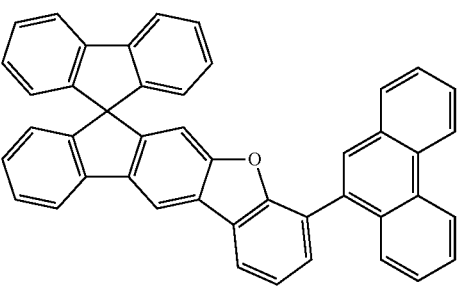

125
-continued
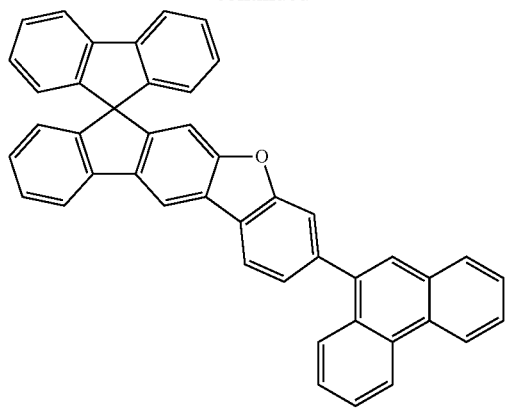
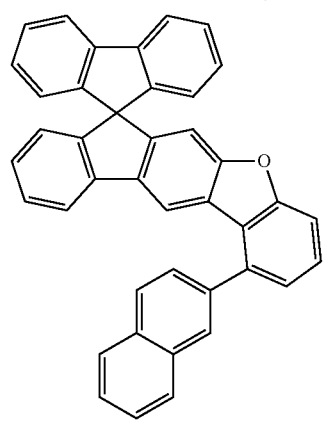
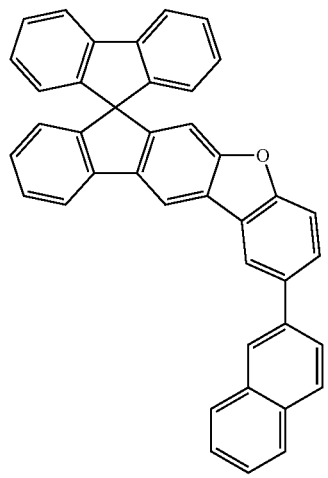
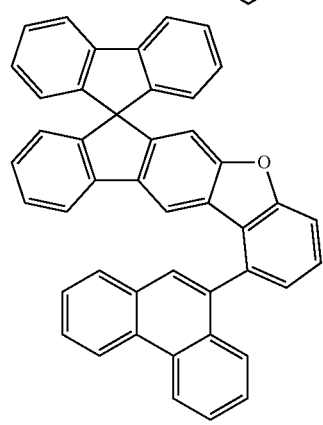
126
-continued
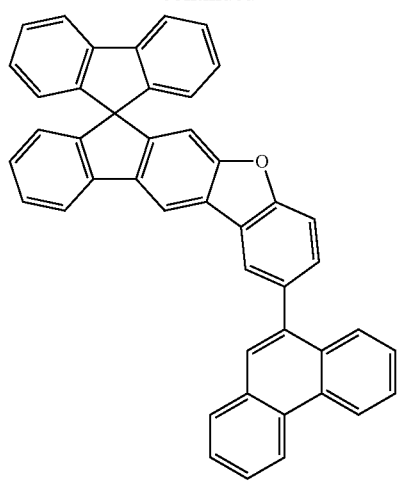
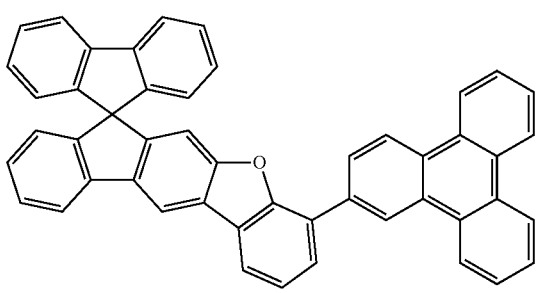
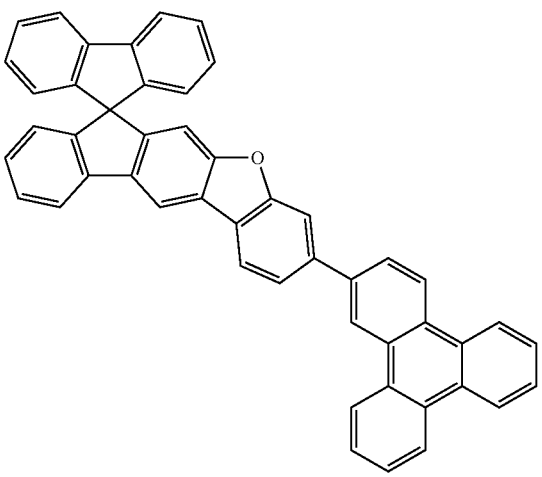
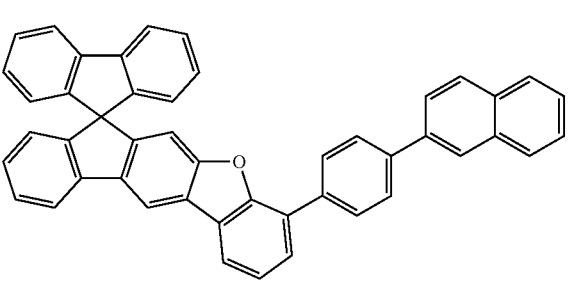

127
-continued
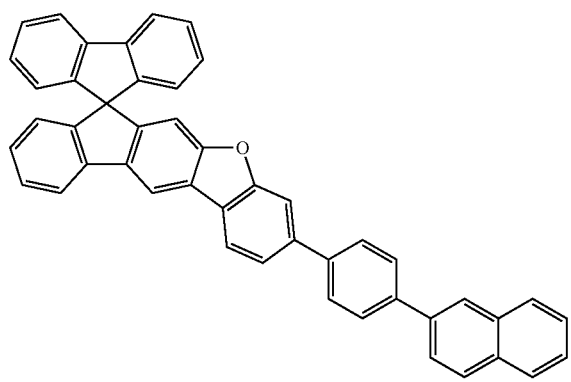
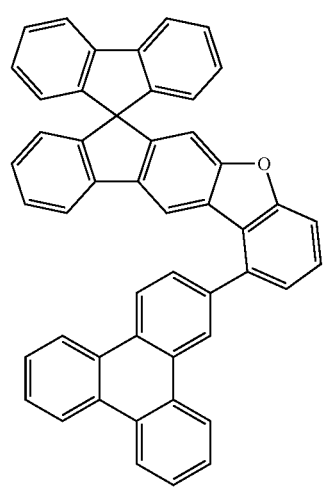
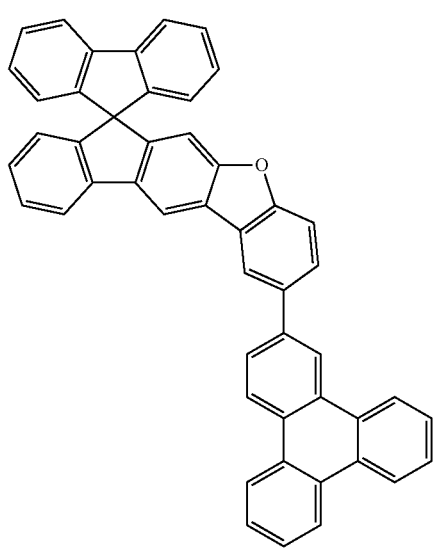
128
-continued
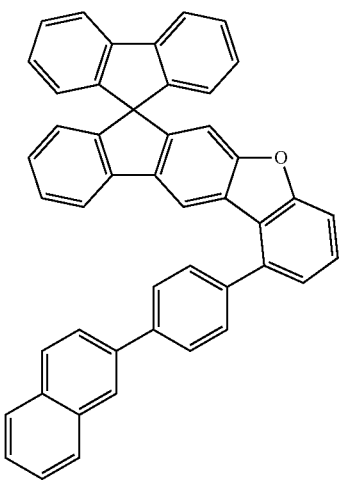
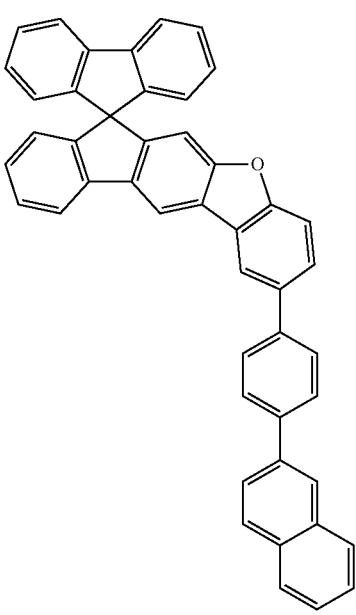
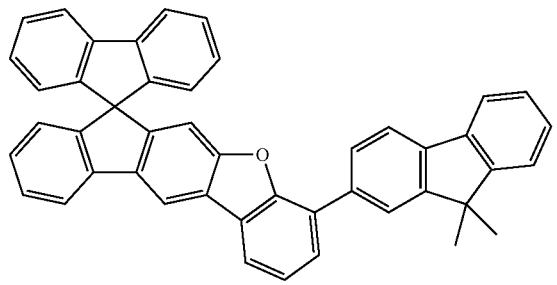

129
-continued
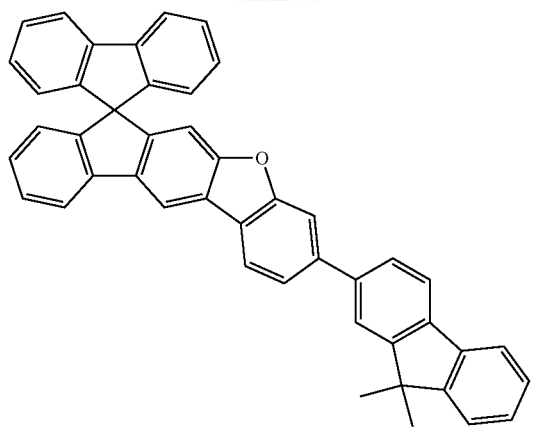
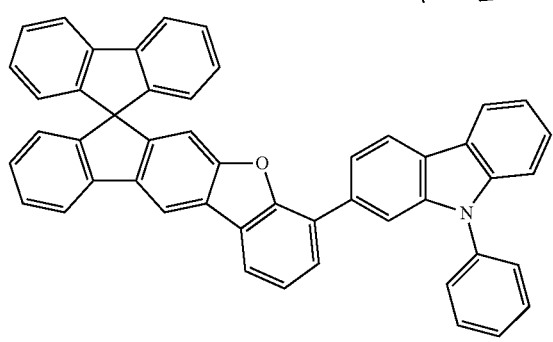
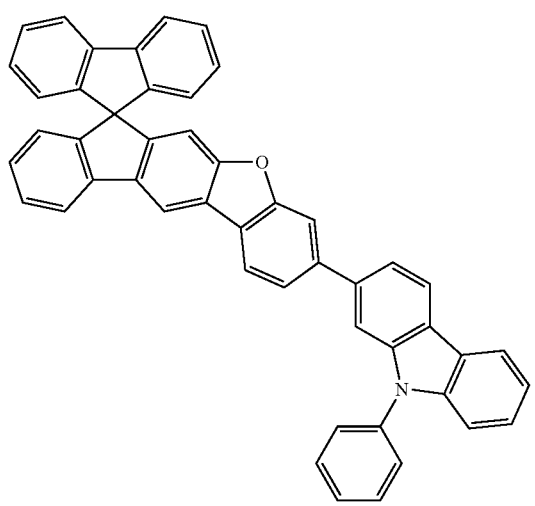
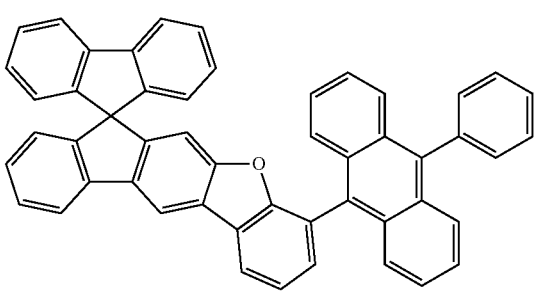
130
-continued
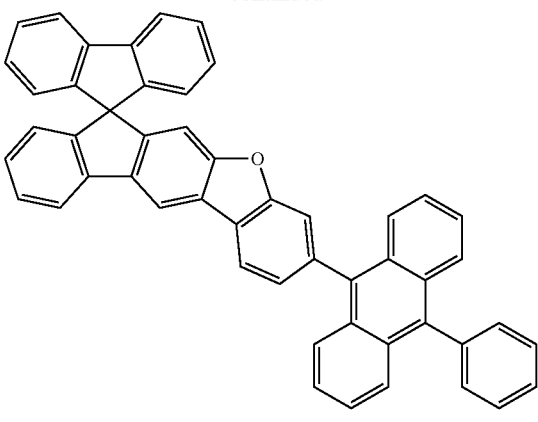
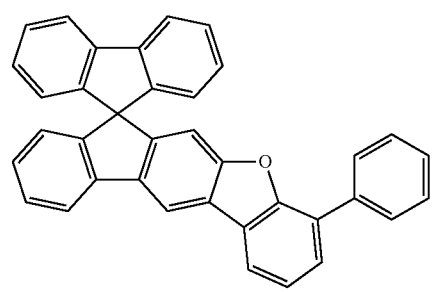
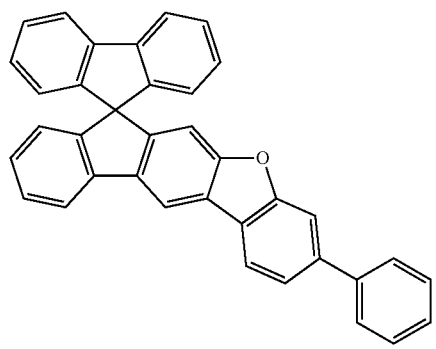
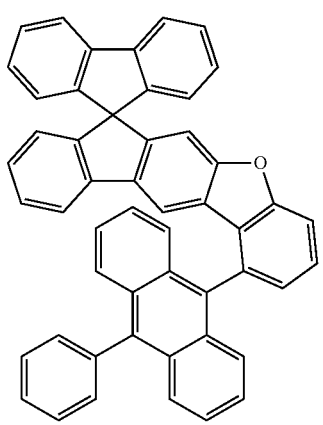

131
-continued
132
-continued
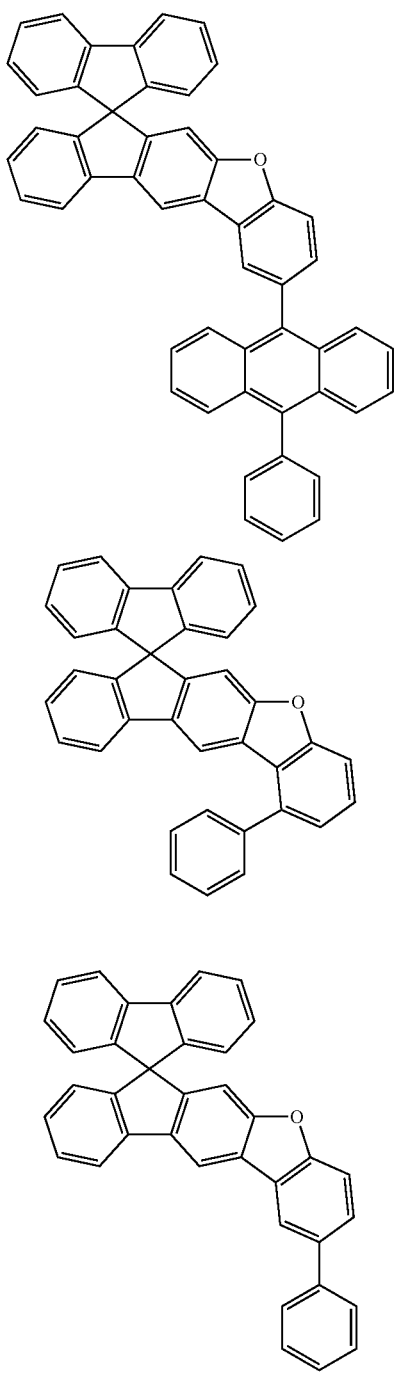
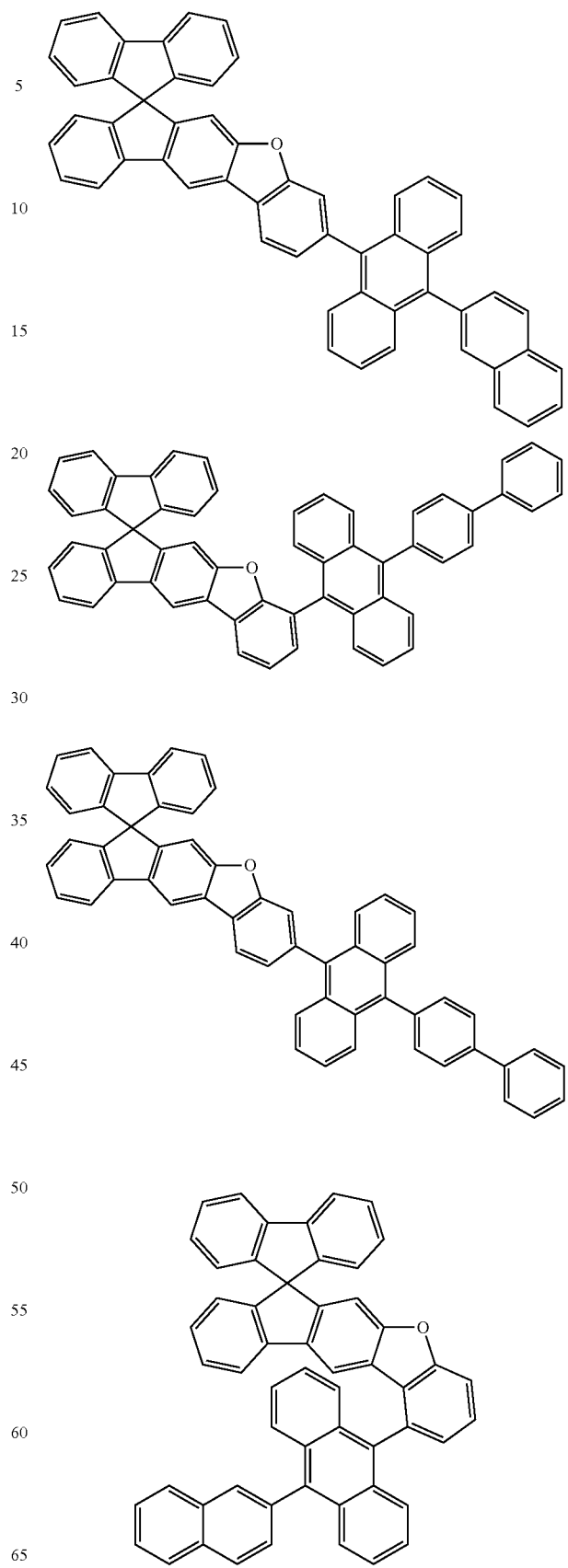

133
-continued
134
-continued
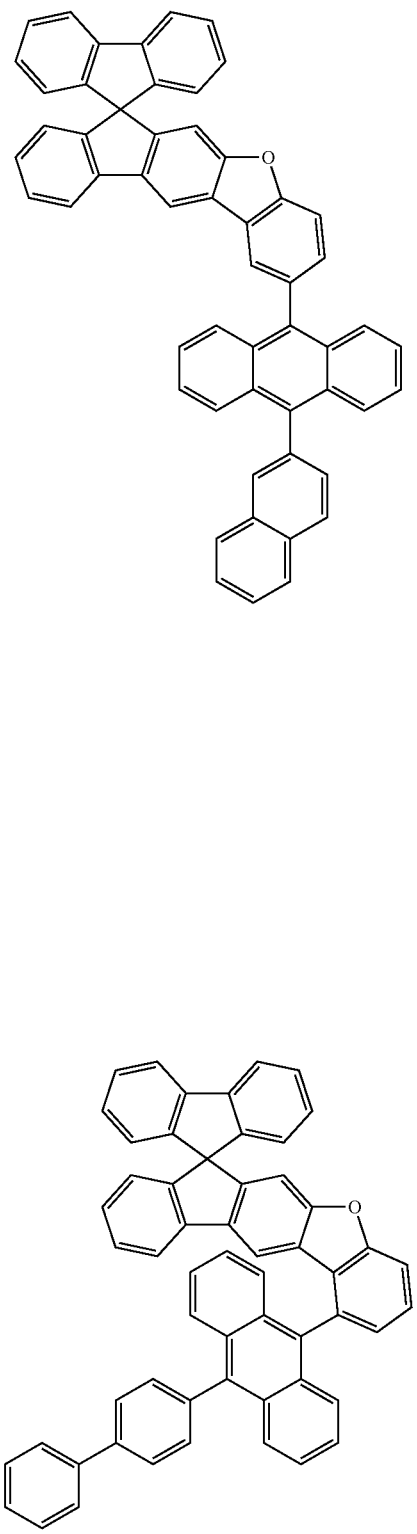
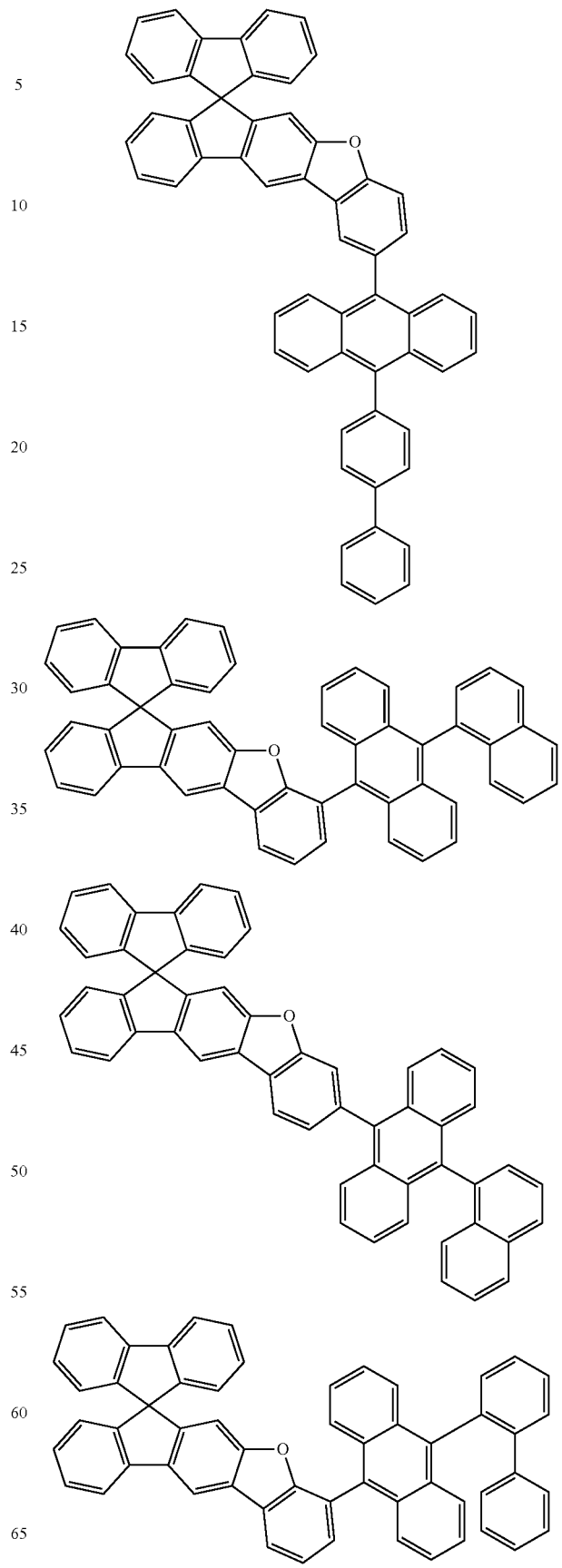

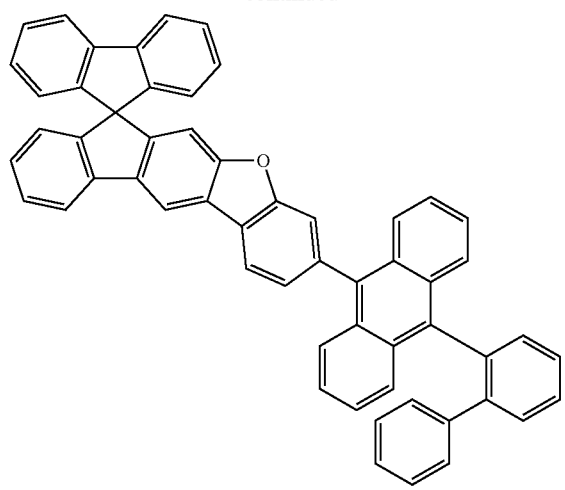
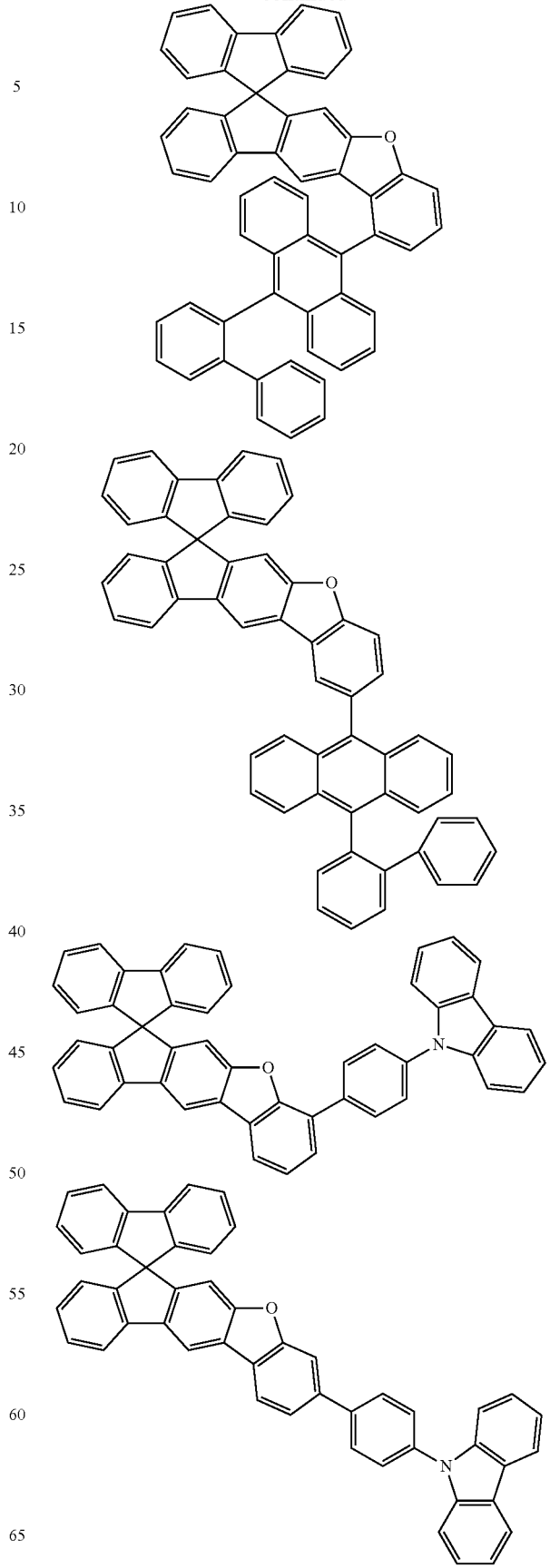

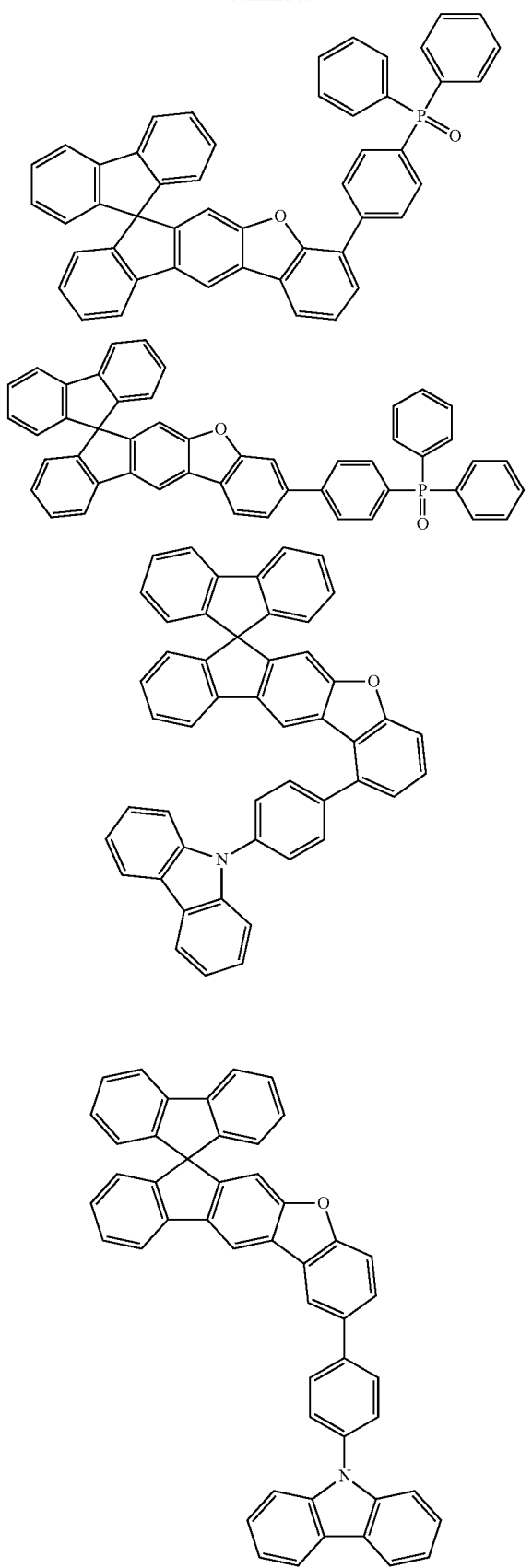
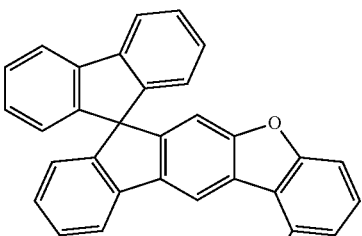
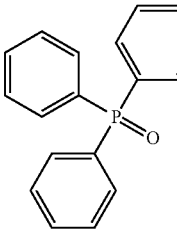
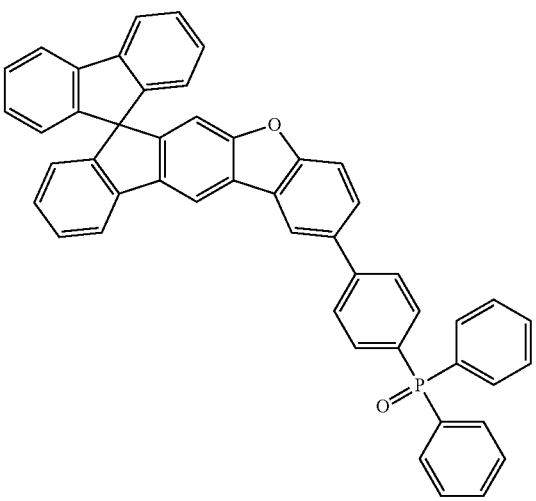
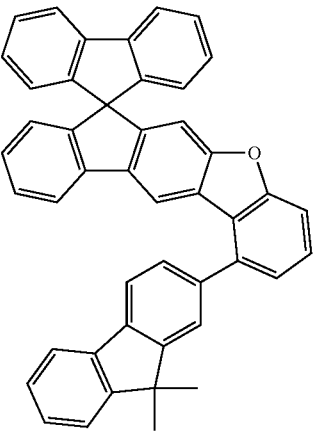

139
-continued
140
-continued
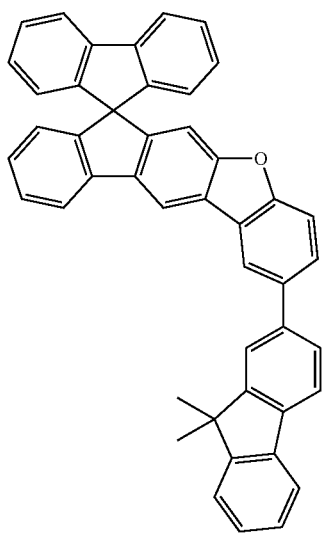
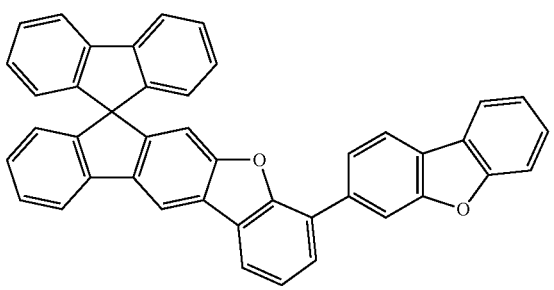
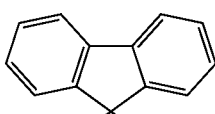
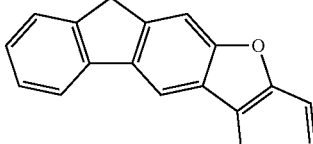
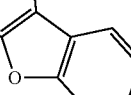
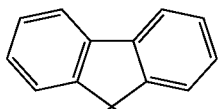
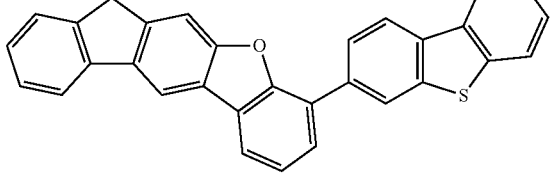
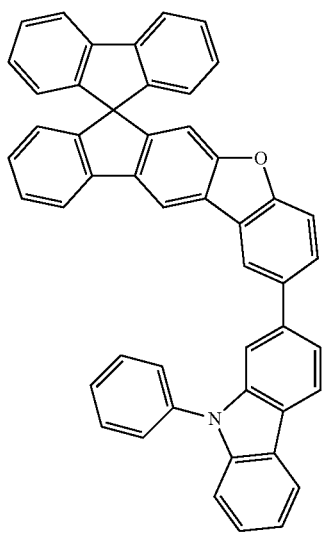
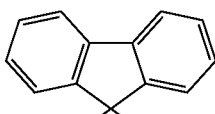
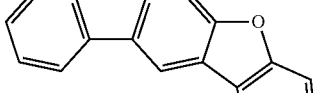
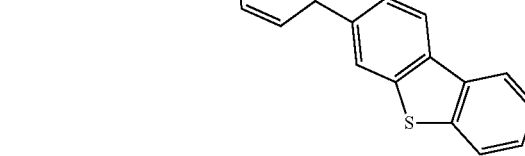

141
-continued
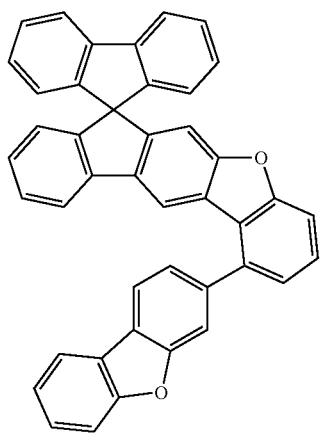
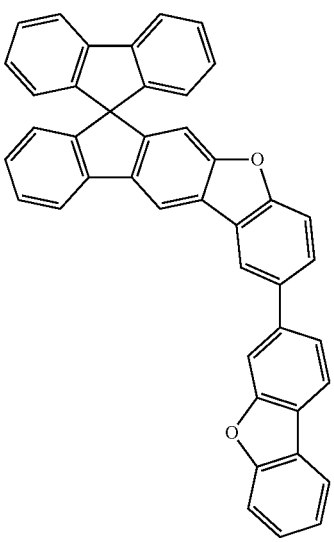
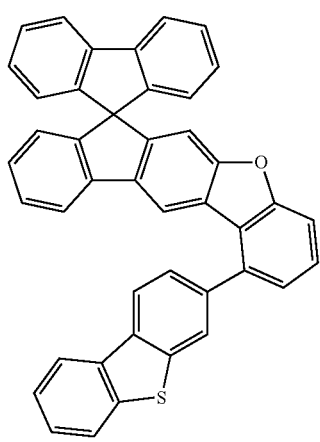
142
-continued
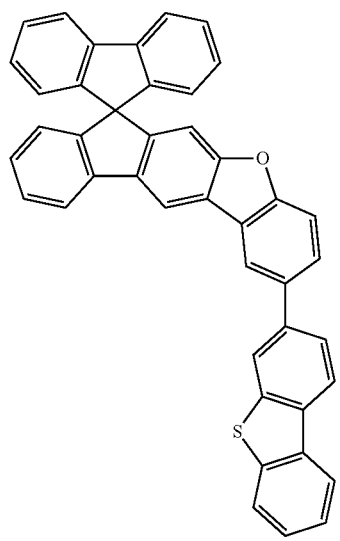
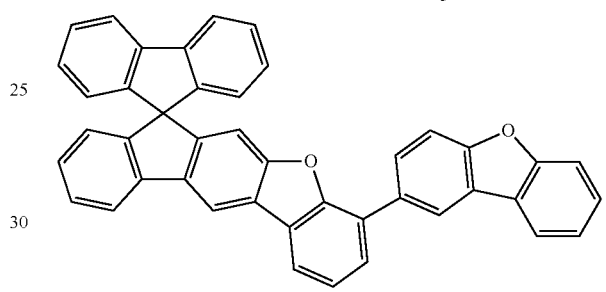
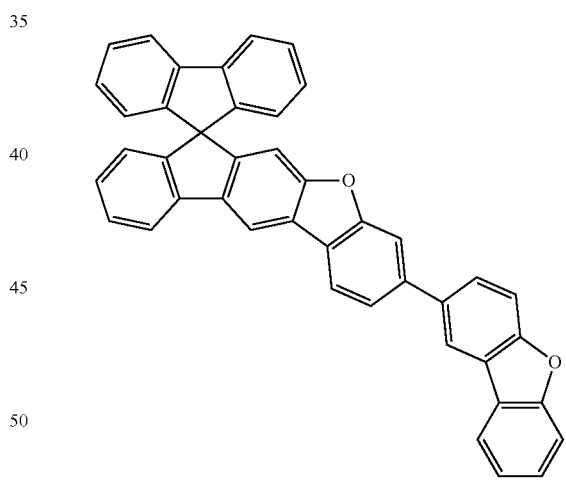
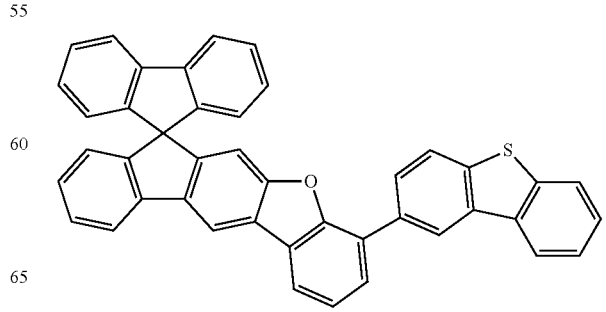

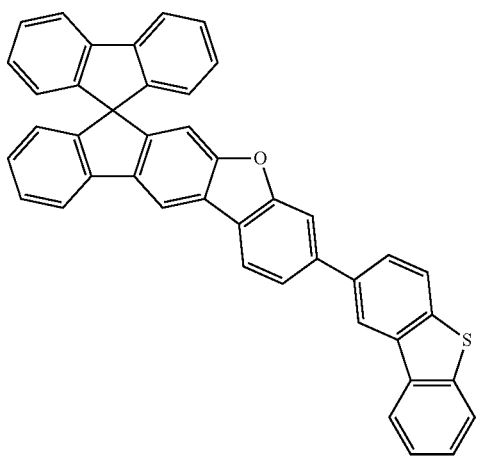
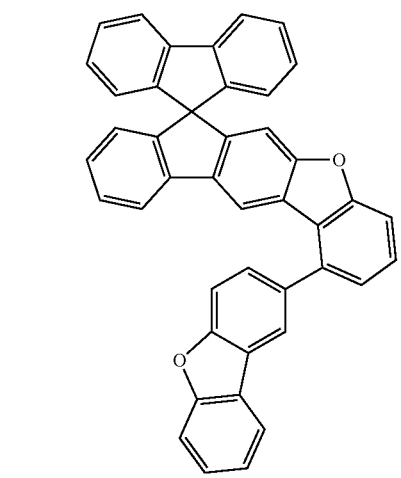
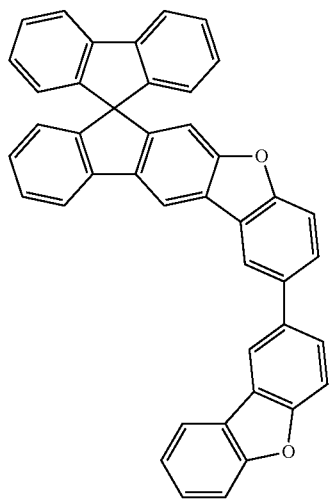
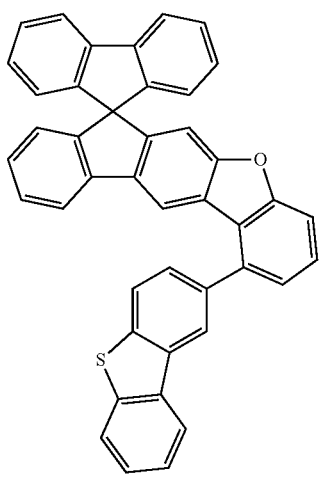
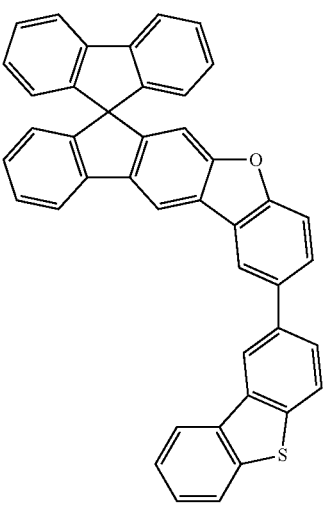
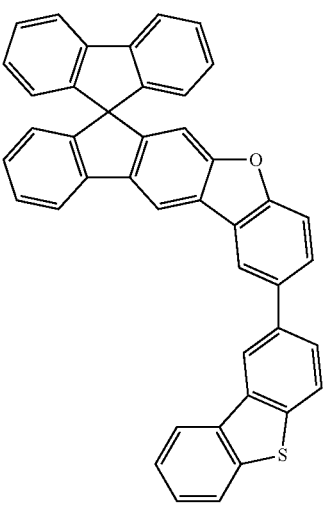
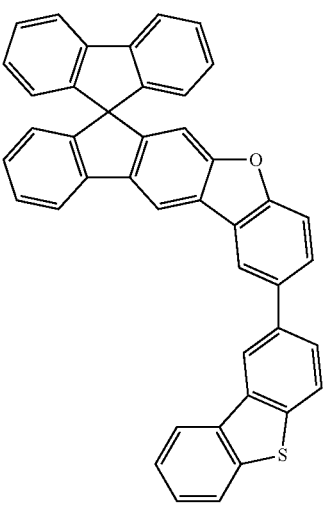

-continued
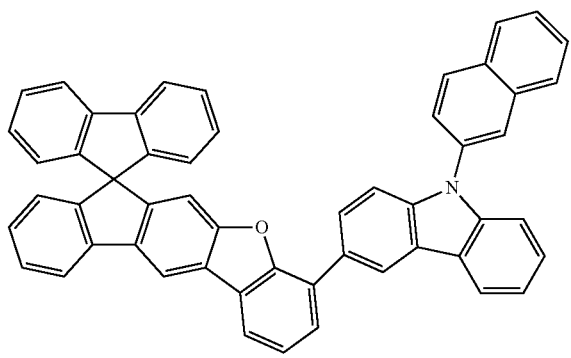
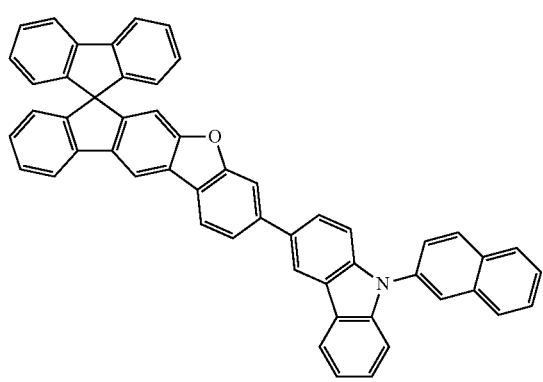
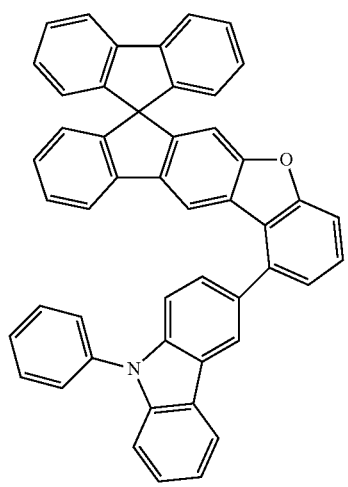
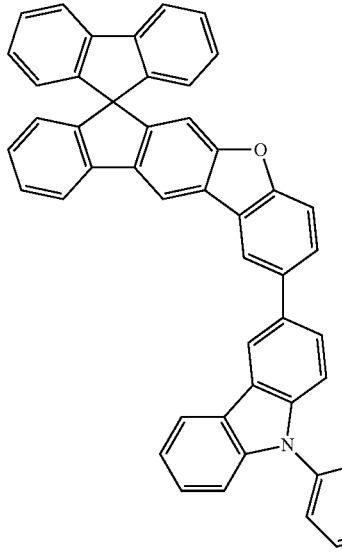
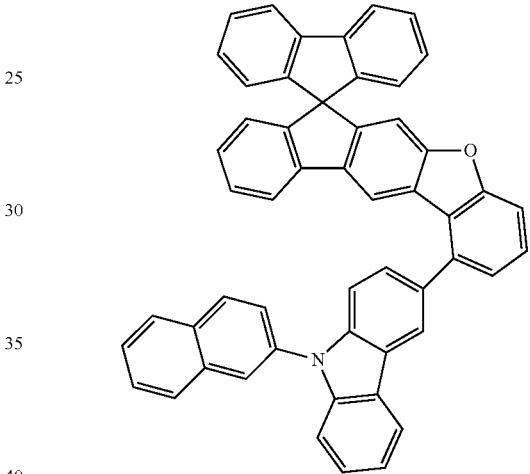
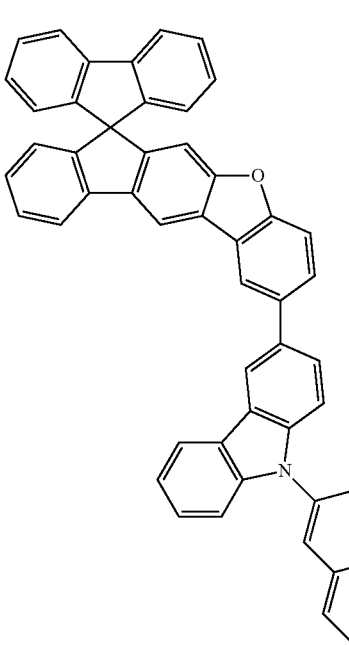

147
-continued
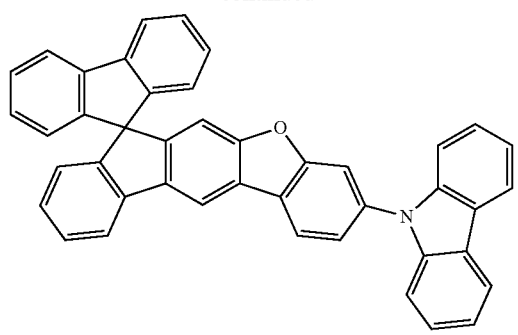
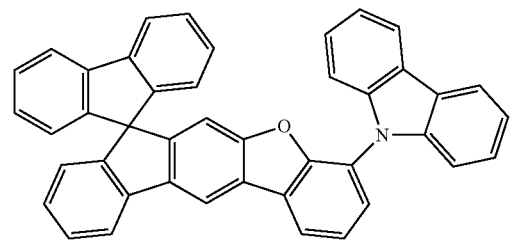
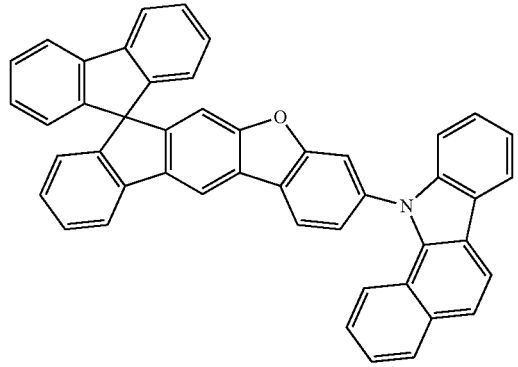
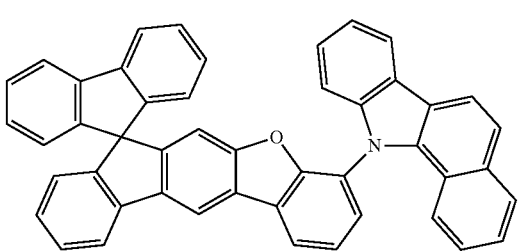
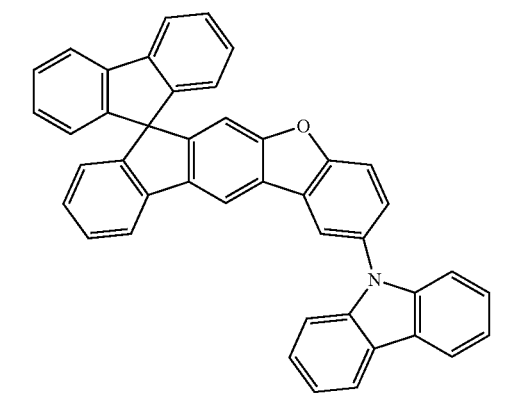
148
-continued
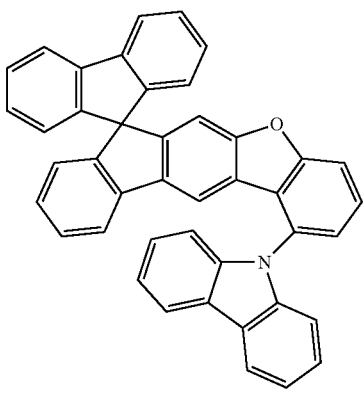
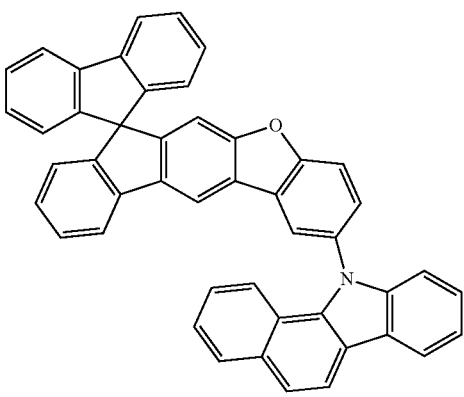
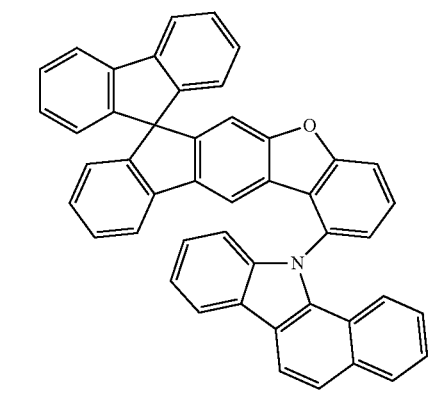
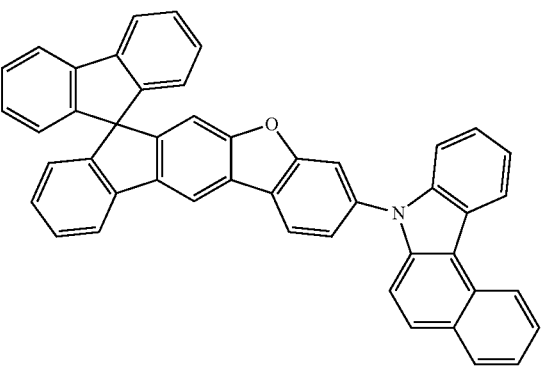

149
-continued
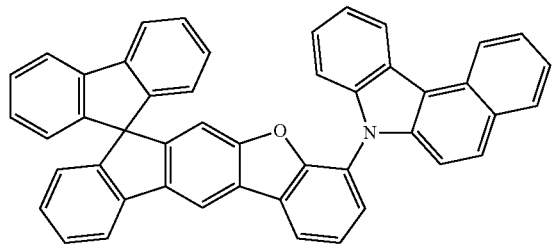
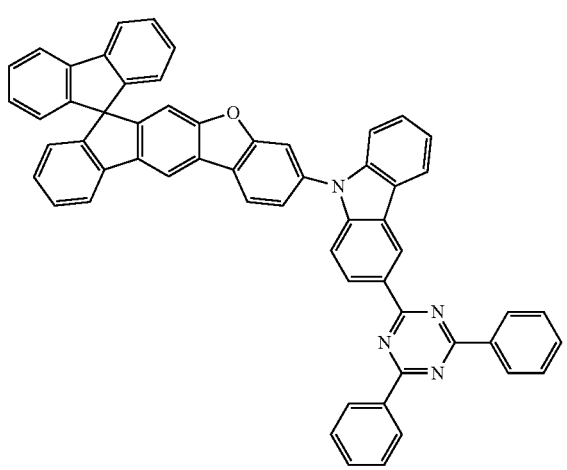
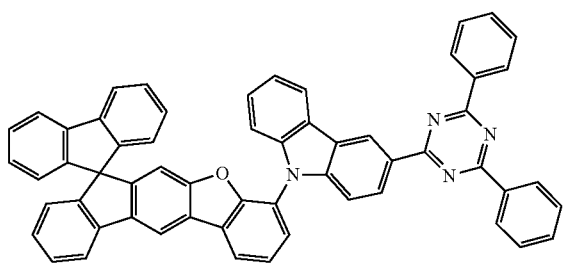
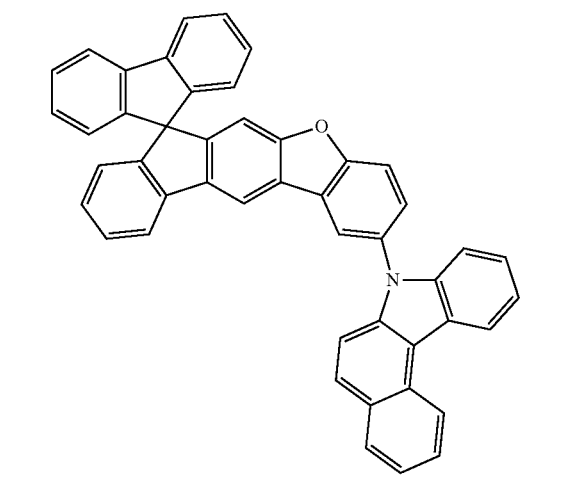
150
-continued
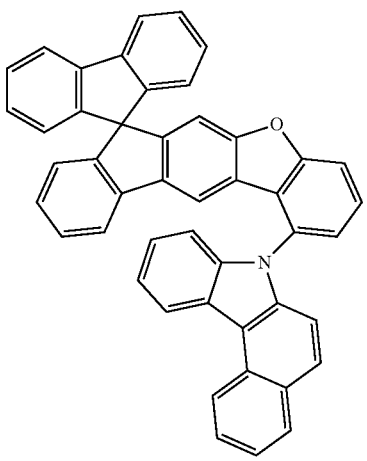
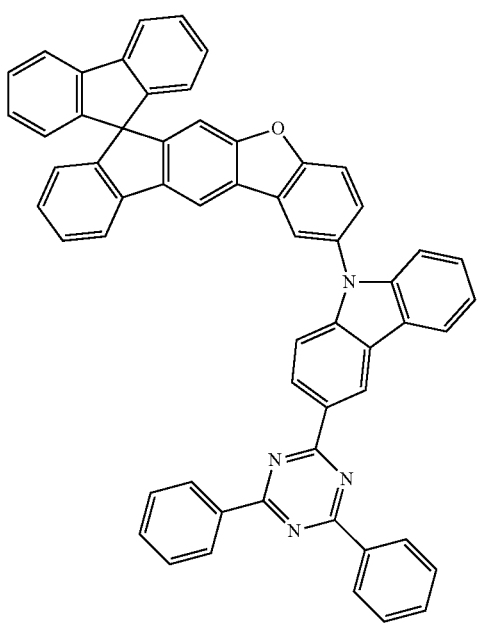
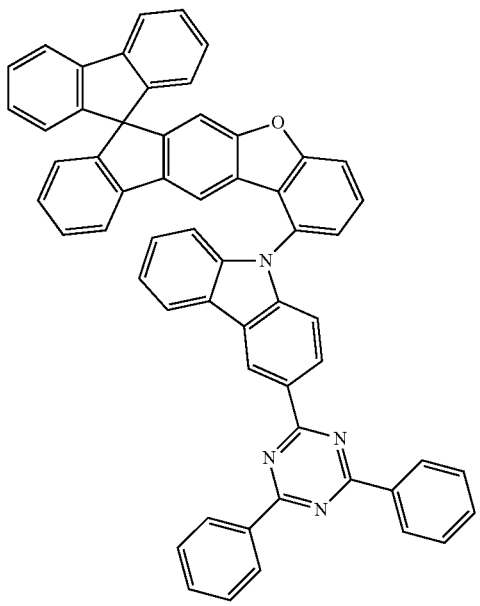

151
-continued
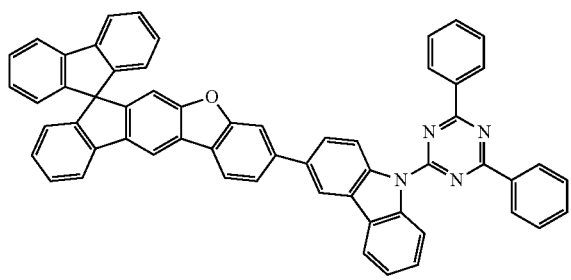
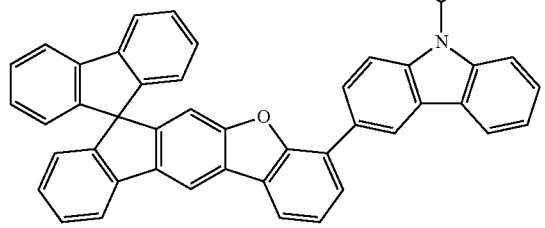
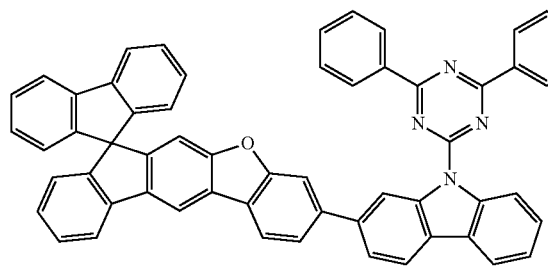
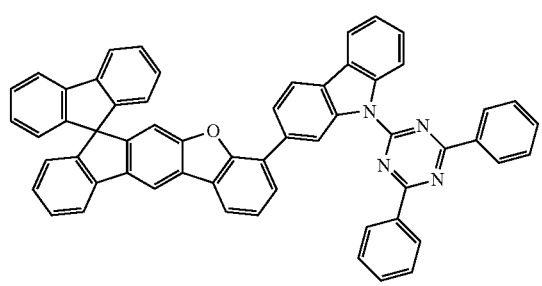
152
-continued
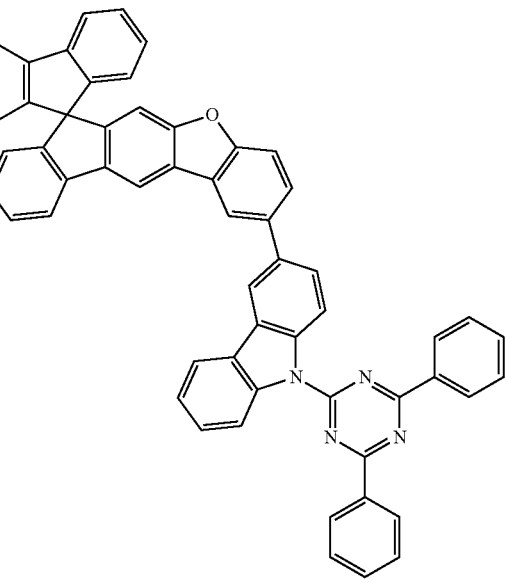
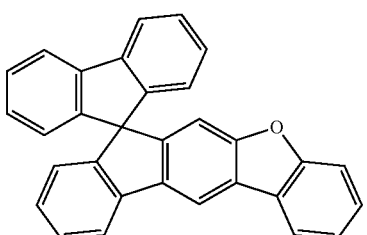
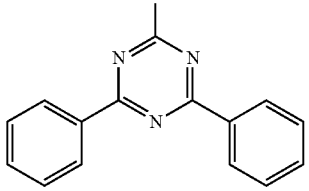
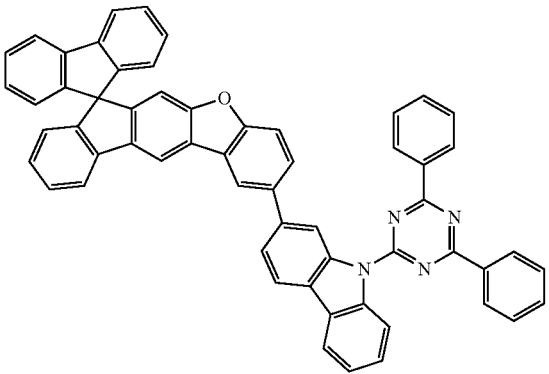

153
-continued
154
-continued
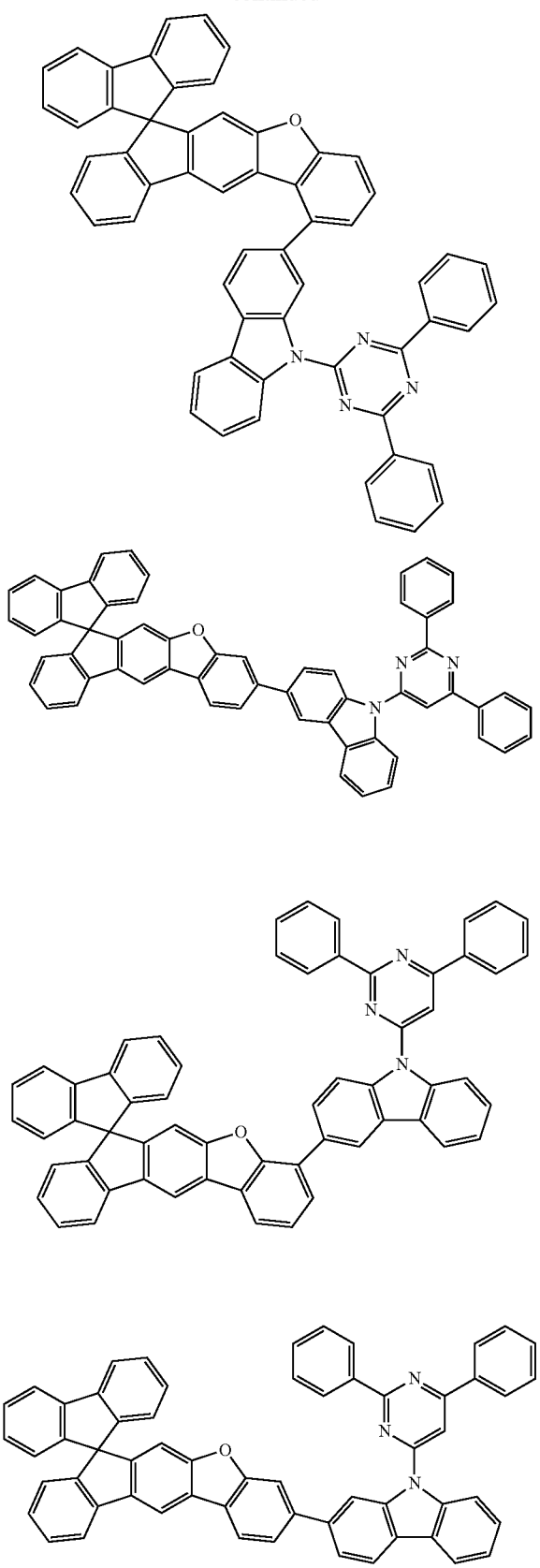
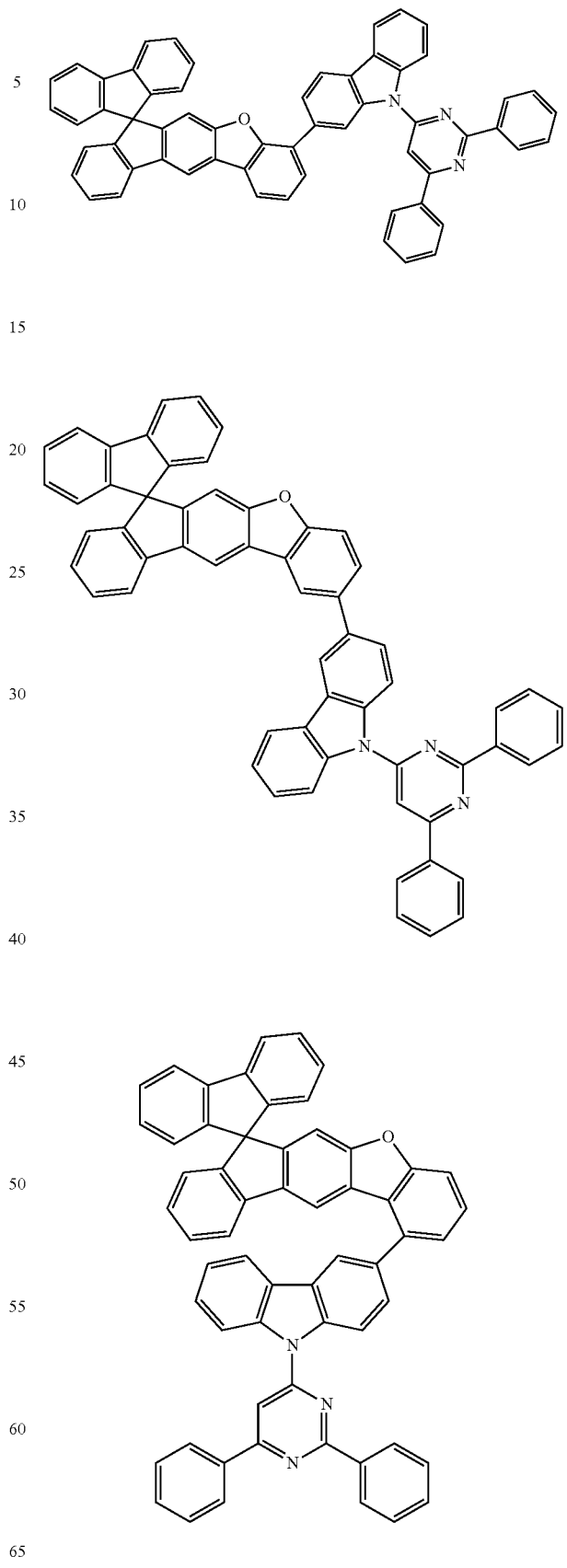

155
-continued
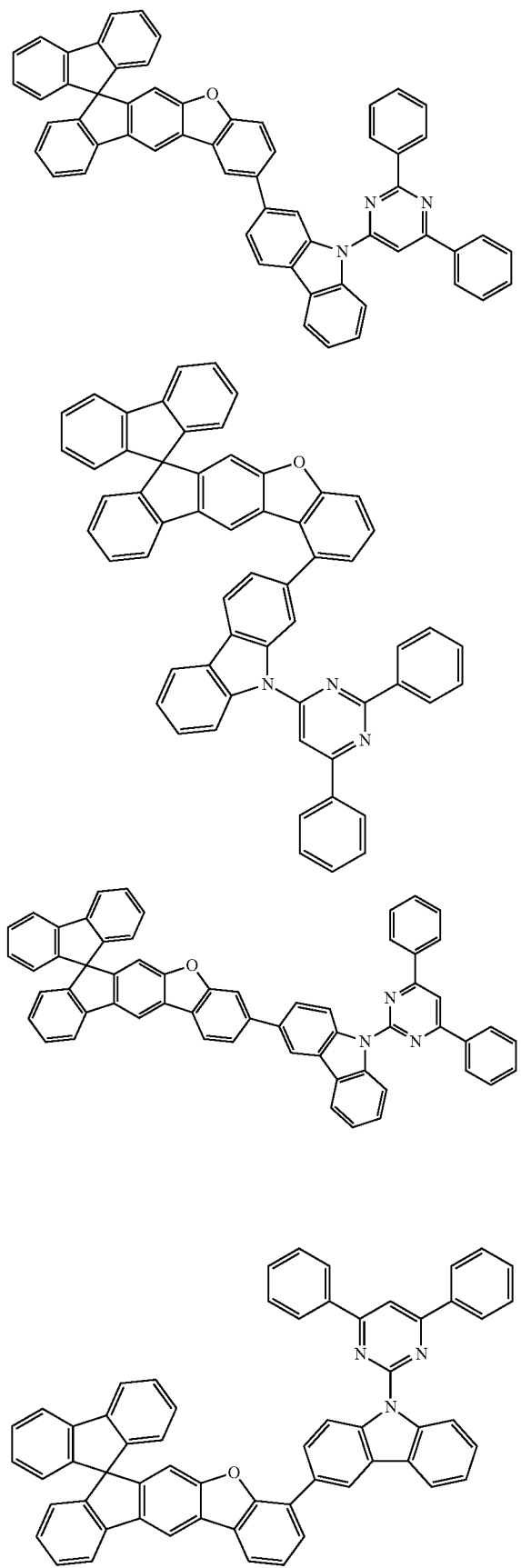
156
-continued
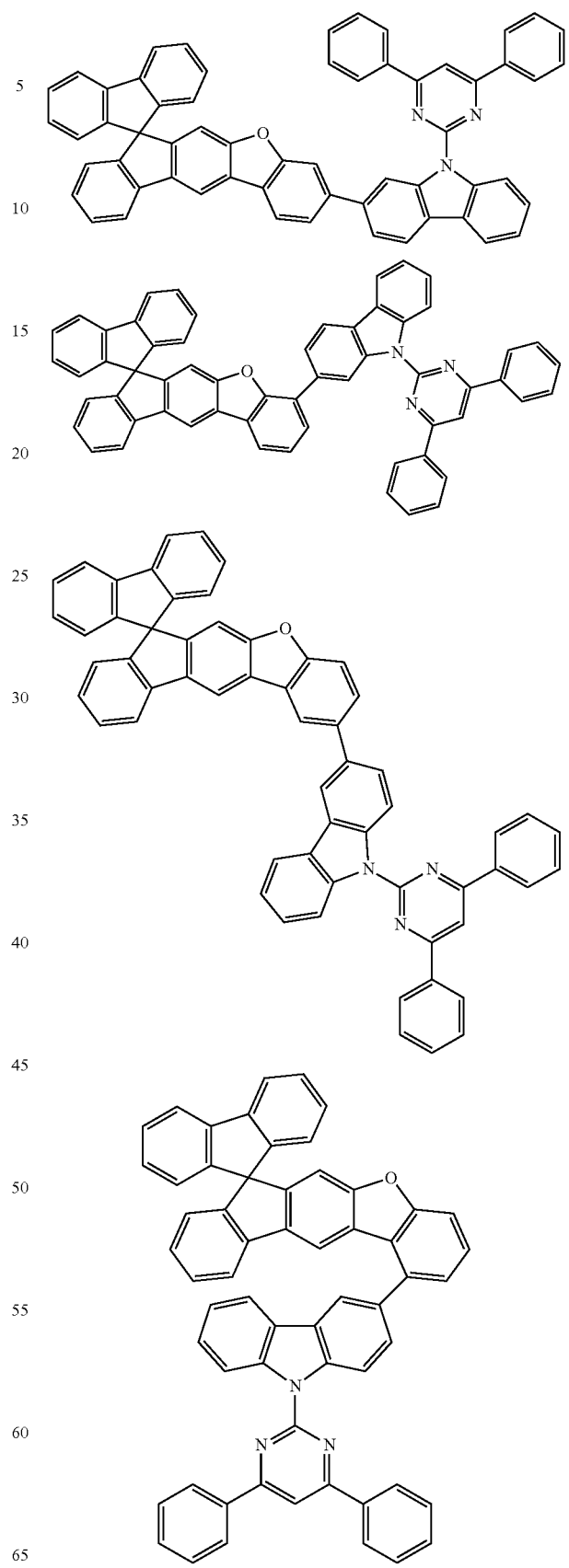

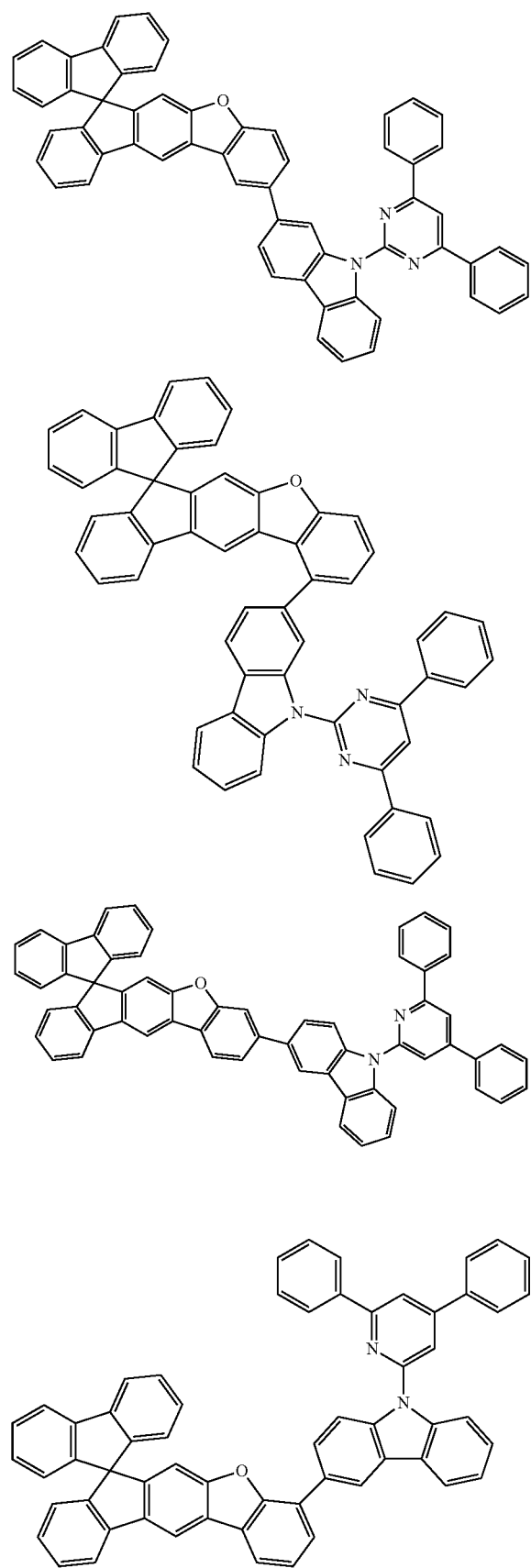
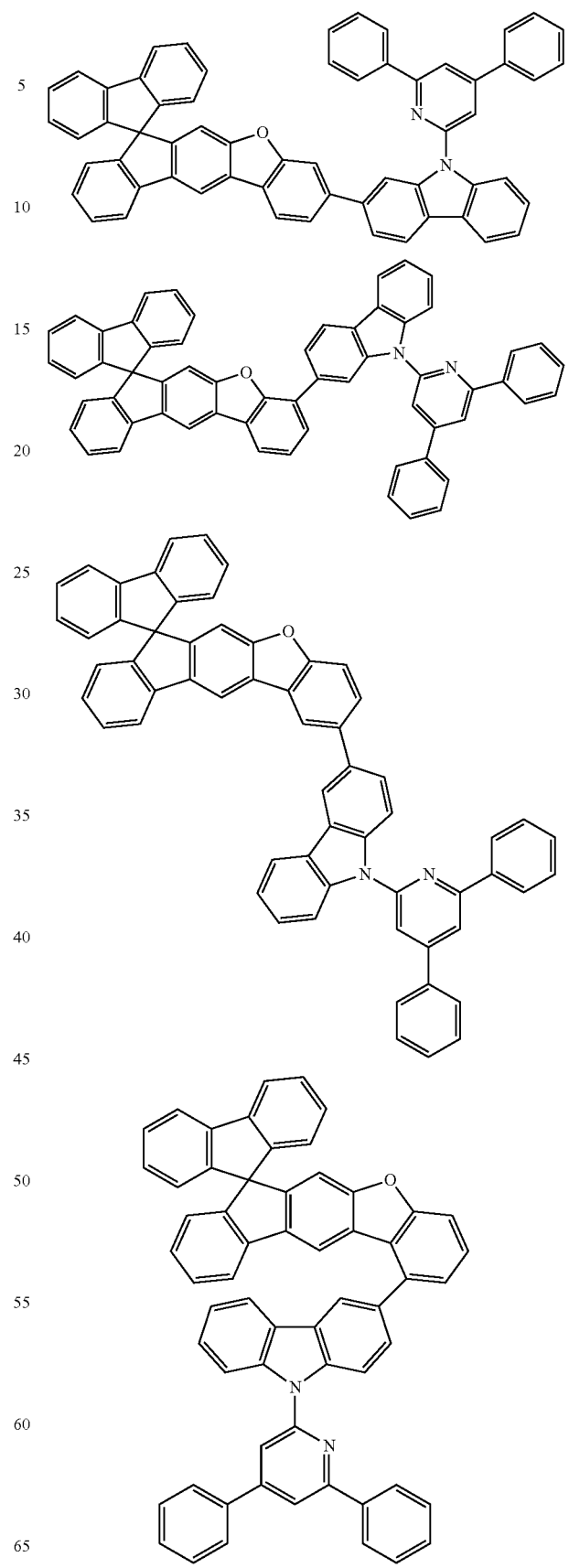

-continued

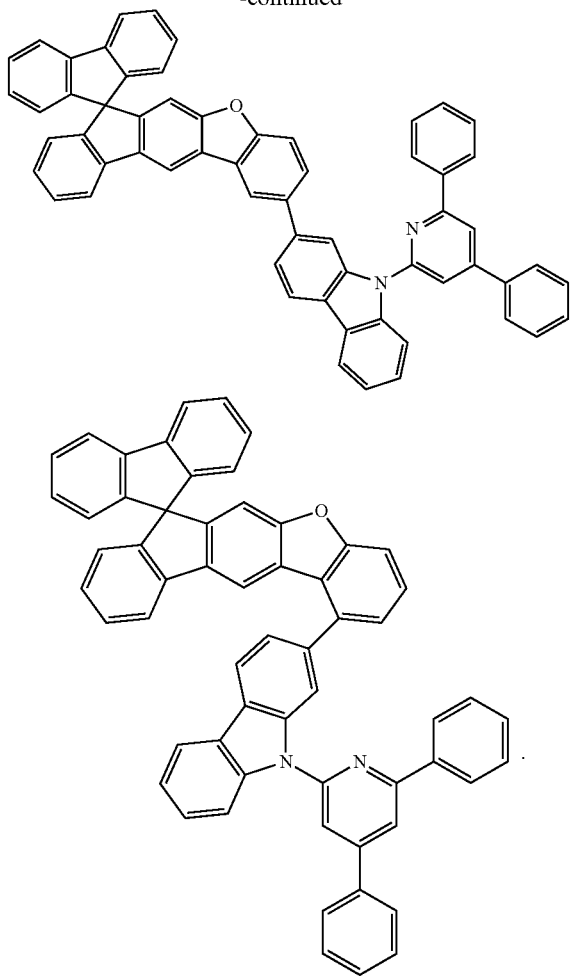

5. An organic light emitting device comprising:
a first electrode;
a second electrode disposed to face the first electrode; and
an organic material layer having one or two or more layers disposed between the first electrode and the second electrode,
wherein the one or more layers of the organic material layer comprise the hetero-cyclic compound of claim 1.

6. The organic light emitting device of claim 5, wherein the organic material layer comprises a hole transporting layer, and the hole transporting layer comprises the hetero-cyclic compound.

7. The organic light emitting device of claim 5, wherein the organic material layer comprises an electron blocking layer, and the electron blocking layer comprises the hetero-cyclic compound.

8. The organic light emitting device of claim 5, wherein the organic material layer comprises a light emitting layer, and the light emitting layer comprises the hetero-cyclic compound.

9. The organic light emitting device of claim 5, wherein the organic material layer comprises a light emitting layer, and the light emitting layer comprises the hetero-cyclic compound as a host of the light emitting layer.

10. The organic light emitting device of claim 5, wherein the organic material layer comprises an electron transporting layer, and the electron transporting layer comprises the hetero-cyclic compound.

11. The hetero-cyclic compound of claim 1, wherein Chemical Formula 1 is represented by any one of the following Chemical Formulae 3 to 5:

[Chemical Formula 3]

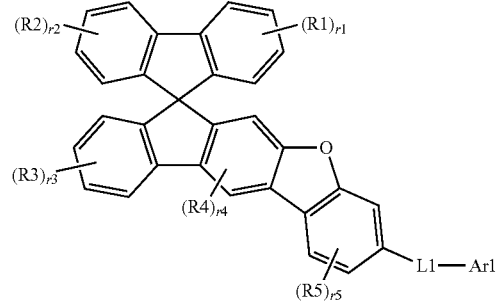

[Chemical Formula 4]

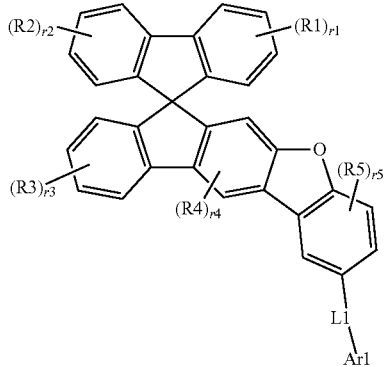

[Chemical Formula 5]

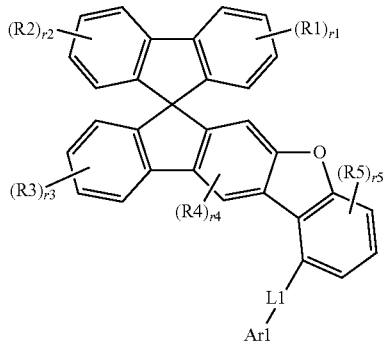

in Chemical Formulae 3 to 5,
the definitions of R1 to R5, r1 to r5, L1, and Ar1 are the same as those in Chemical Formula 1.

* * * * *